United States Patent
Ruppel et al.

(10) Patent No.: US 11,851,445 B2
(45) Date of Patent: Dec. 26, 2023

(54) COMPOUNDS AND USES THEREOF

(71) Applicant: Foghorn Therapeutics Inc., Cambridge, MA (US)

(72) Inventors: Sabine K. Ruppel, Cambridge, MA (US); Zhaoxia Yang, Belmont, MA (US); Jason T. Lowe, East Bridgewater, MA (US); Johannes H. Voigt, Cambridge, MA (US)

(73) Assignee: FOGHORN THERAPEUTICS INC., Cambridge, MA (US)

( * ) Notice: Subject to any disclaimer, the term of this patent is extended or adjusted under 35 U.S.C. 154(b) by 0 days.

(21) Appl. No.: 17/162,608

(22) Filed: Jan. 29, 2021

(65) Prior Publication Data

US 2021/0230190 A1    Jul. 29, 2021

Related U.S. Application Data

(60) Provisional application No. 63/058,121, filed on Jul. 29, 2020, provisional application No. 62/967,524, filed on Jan. 29, 2020.

(51) Int. Cl.
| | |
|---|---|
| *C07D 519/00* | (2006.01) |
| *A61P 35/00* | (2006.01) |
| *A61P 35/02* | (2006.01) |
| *A61K 47/54* | (2017.01) |
| *A61K 47/55* | (2017.01) |
| *C07D 471/10* | (2006.01) |
| *A61K 31/4545* | (2006.01) |
| *A61K 31/12* | (2006.01) |

(52) U.S. Cl.
CPC ............ *C07D 519/00* (2013.01); *A61P 35/00* (2018.01)

(58) Field of Classification Search
CPC ..... C07D 519/00; C07D 471/10; A61P 35/00; A61P 31/12; A61P 35/02; A61K 47/545; A61K 47/55; A61K 31/4545
See application file for complete search history.

(56) References Cited

U.S. PATENT DOCUMENTS

| | | | |
|---|---|---|---|
| 5,858,358 A | 1/1999 | June et al. | |
| 5,883,223 A | 3/1999 | Gray | |
| 6,352,694 B1 | 3/2002 | June et al. | |
| 6,534,055 B1 | 3/2003 | June et al. | |
| 6,692,964 B1 | 2/2004 | June et al. | |
| 6,797,514 B2 | 9/2004 | Berenson et al. | |
| 6,867,041 B2 | 3/2005 | Berenson et al. | |
| 6,887,466 B2 | 5/2005 | June et al. | |
| 6,905,680 B2 | 6/2005 | June et al. | |
| 6,905,681 B1 | 6/2005 | June et al. | |
| 6,905,874 B2 | 6/2005 | Berenson et al. | |
| 7,056,883 B2 | 6/2006 | Ito et al. | |
| 7,067,318 B2 | 6/2006 | June et al. | |
| 7,144,575 B2 | 12/2006 | June et al. | |
| 7,172,869 B2 | 2/2007 | June et al. | |
| 7,175,843 B2 | 2/2007 | June et al. | |
| 7,205,103 B2 | 4/2007 | Emerson | |
| 7,232,566 B2 | 6/2007 | June et al. | |
| 9,271,978 B2 | 3/2016 | Liu et al. | |
| 9,353,051 B2 | 5/2016 | Byrd et al. | |
| 9,410,943 B2 | 8/2016 | Kadoch et al. | |
| 10,105,420 B2 | 10/2018 | Kadoch et al. | |
| 10,464,925 B2 | 11/2019 | Bradner et al. | |
| 10,646,575 B2 | 5/2020 | Phillips et al. | |
| 10,660,968 B2 | 5/2020 | Phillips et al. | |
| 10,725,057 B2 | 7/2020 | Tojo et al. | |
| 10,849,982 B2 | 12/2020 | Phillips et al. | |
| 10,905,768 B1 | 2/2021 | Phillips et al. | |
| 10,976,320 B2 | 4/2021 | Dykhuizen et al. | |
| 11,185,592 B2 | 11/2021 | Phillips et al. | |
| 11,414,416 B1 | 8/2022 | Ruppel et al. | |
| 11,560,381 B1 | 1/2023 | Ruppel et al. | |
| 2005/0079512 A1 | 4/2005 | Emerson et al. | |
| 2006/0121005 A1 | 6/2006 | Berenson et al. | |
| 2011/0053897 A1 | 3/2011 | Che et al. | |
| 2011/0061116 A1 | 3/2011 | Haldar et al. | |
| 2011/0201602 A1 | 8/2011 | Geuns-Meyer et al. | |
| 2016/0058872 A1 | 3/2016 | Crew et al. | |
| 2016/0200721 A1 | 7/2016 | Yukimasa et al. | |
| 2016/0347708 A1 | 12/2016 | Ebright et al. | |
| 2017/0014491 A1 | 1/2017 | Kadoch et al. | |
| 2017/0050968 A1 | 2/2017 | Bennett et al. | |
| 2017/0158709 A1 | 6/2017 | Boloor | |
| 2017/0190686 A1 | 7/2017 | Tojo et al. | |
| 2017/0340605 A1 | 11/2017 | Albrecht et al. | |
| 2018/0044335 A1 | 2/2018 | Martin et al. | |
| 2018/0085465 A1 | 3/2018 | Bradner et al. | |
| 2018/0187614 A1 | 7/2018 | Dudar | |
| 2018/0213422 A1 | 7/2018 | Kazmi et al. | |

(Continued)

FOREIGN PATENT DOCUMENTS

| | | |
|---|---|---|
| CN | 107056772 A | 8/2017 |
| CN | 108690020 A | 10/2018 |

(Continued)

OTHER PUBLICATIONS

Zhu, X., "Targeting BRD9 for cancer treatment: a new strategy." OncoTargets and therapy 13 (2020): 13191-13200.*
Börold, J., "BRD9 is a druggable component of interferon-stimulated gene expression and antiviral activity." EMBO reports 22.10 (2021): e52823:1-18.*
Hu, Z., "Genomic characterization of genes encoding histone acetylation modulator proteins identifies therapeutic targets for cancer treatment." Nature communications 10.1 (2019): 1-17.*
International Search Report and Written Opinion for Intenational Patent Application No. PCT/US21/15813, dated Apr. 6, 2021 (24 pages).
Remillard et al., "Degradation of the BAF Complex Factor BRD9 by Heterobifunctional Ligands," Angew Chem Int Ed Engl. 56(21):5738-5743 (2017) (14 pages).
U.S. Appl. No. 17/425,013, Brucelle et al.

(Continued)

*Primary Examiner* — John M Mauro
(74) *Attorney, Agent, or Firm* — Clark & Elbing LLP

(57) ABSTRACT

The present disclosure features compounds useful for the treatment of BAF complex-related disorders.

6 Claims, 24 Drawing Sheets

(56) References Cited

U.S. PATENT DOCUMENTS

| | | |
|---|---|---|
| 2018/0215766 A1 | 8/2018 | Bair et al. |
| 2018/0215866 A1 | 8/2018 | Zhao et al. |
| 2018/0328913 A1 | 11/2018 | Kadoch et al. |
| 2019/0076539 A1 | 3/2019 | Phillips et al. |
| 2019/0219562 A1 | 7/2019 | Matyskiela et al. |
| 2019/0247509 A1 | 8/2019 | Buckley et al. |
| 2019/0322683 A1 | 10/2019 | Chan et al. |
| 2020/0140456 A1 | 5/2020 | Phillips et al. |
| 2020/0206344 A1 | 7/2020 | Kadoch et al. |
| 2021/0009568 A1 | 1/2021 | Zhou et al. |
| 2021/0198256 A1 | 7/2021 | Nasveschuk et al. |
| 2021/0230190 A1 | 7/2021 | Ruppel et al. |
| 2022/0048906 A1 | 2/2022 | Ruppel et al. |
| 2022/0098190 A1 | 3/2022 | Ruppel et al. |
| 2022/0193205 A1 | 6/2022 | Zhou et al. |
| 2022/0289711 A1 | 9/2022 | Ruppel et al. |
| 2022/0315578 A1* | 10/2022 | Chen .................. C07D 401/14 |
| 2023/0065463 A1 | 3/2023 | Ruppel et al. |
| 2023/0066136 A1 | 3/2023 | Ruppel et al. |
| 2023/0077730 A1 | 3/2023 | Ruppel et al. |

FOREIGN PATENT DOCUMENTS

| | | |
|---|---|---|
| WO | WO-2017/197051 A1 | 11/2017 |
| WO | WO-2017/197056 A1 | 11/2017 |
| WO | WO-2017/223452 A1 | 12/2017 |
| WO | WO-2018/177297 A1 | 10/2018 |
| WO | WO-2019/099868 A2 | 5/2019 |
| WO | WO-2019/152437 A1 | 8/2019 |
| WO | WO-2019/195201 A1 | 10/2019 |
| WO | WO-2019/207538 A1 | 10/2019 |
| WO | WO-2020/051235 A1 | 3/2020 |
| WO | WO-2020/078933 A1 | 4/2020 |
| WO | WO-2020/132561 A1 | 6/2020 |
| WO | WO-2020/160192 A1 | 8/2020 |
| WO | WO-2020/160193 A2 | 8/2020 |
| WO | WO-2020/160198 A1 | 8/2020 |
| WO | WO-2020/239103 A1 | 12/2020 |
| WO | WO-2021/055295 A1 | 3/2021 |
| WO | WO-2021/178920 A1 | 9/2021 |

OTHER PUBLICATIONS

U.S. Appl. No. 17/425,153, Ruppel et al.

U.S. Appl. No. 17/696,656, Ruppel et al.

Brien et al., Targeted degradation of BRD9 reverses oncogenic gene expression in synovial sarcoma,eLIFE. 7:1-26 (2018).

Crawford et al., "Inhibition of bromodomain-containing protein 9 for the prevention of epigenetically-defined drug resistance," Bioorg Med Chem Lett. 27(15):3534-41(2017).

Hay et al., "Design and synthesis of potent and selective inhibitors of BRD7 and BRD9 bromodomains," Medchemcomm. 6:1381-86 (2015).

Hohmann et al., "Sensitivity and engineered resistance of myeloid leukemia cells to BRD9 inhibition," Nat Chem Biol. 12(9): 672-679 (2016) (12 pages).

Kadoch et al., "Mammalian SWI/SNF chromatin remodeling complexes and cancer: Mechanistic insights gained from human genomics," Sci Adv. 1(5):e1500447 (2015) (17 pages).

Kadoch et al., "Proteomic and bioinformatic analysis of mammalian SWI/SNF complexes identifies extensive roles in human malignancy," Nat Genet. 45(6):592-601 (2013) (11 pages).

Kadoch et al., "Reversible Disruption of mSWI/SNF (BAF) Complexes by the SS18-SSX Oncogenic Fusion in Synovial Sarcoma," Cell. 153(1):71-85 (2013).

Martin et al., "Structure-Based Design of an in Vivo Active Selective BRD9 Inhibitor," J Med Chem. 59(10):4462-75 (2016).

McBride et al., "Disruption of mammalian SWI/SNF and polycomb complexes in human sarcomas: mechanisms and therapeutic opportunities," J Pathol. 244(5): 638-649 (2018).

Michael et al., "Abstract PR15: BRD9 defines a novel mammalian SWI/SNF (BAF) complex configuration which supports proliferation in AML.," Clin Cancer Res. 23(24): (2017).

Pan et al., "A major chromatin regulator determines resistance of tumor cells to T cell-mediated killing," Science. 359(6377):770-75 (2018) (11 pages).

Picaud et al., "9H-purine scaffold reveals induced-fit pocket plasticity of the BRD9 bromodomain," J Med Chem. 58(6):2718-36(2015).

Remillard et al., "Degradation of the BAF Complex Factor BRD9 by Heterobifunctional Ligands," Angew Chem Int Ed Engl. 56(21):5738-43 (2017) (7 pages).

Teuscher et al., "A Versatile Method to Determine the Cellular Bioavailability of Small-Molecule Inhibitors," J Med Chem. 60(1): 157-169 (2017).

Theodoulou et al., "Discovery of I-BRD9, a Selective Cell Active Chemical Probe for Bromodomain Containing Protein 9 Inhibition," J Med Chem. 59(4):1425-39 (2015).

Vangamudi et al., "The SMARCA2/4 ATPase Domain Surpasses the Bromodomain as a Drug Target in SWI/SNF-Mutant Cancers: Insights from cDNA Rescue and PFI-3 Inhibitor Studies," Cancer Res. 75(18):3865-78 (2015).

Wang et al., "NMR Fragment Screening Hit Induces Plasticity of BRD7/9 Bromodomains," Chembiochem. 17(15):1456-63 (2016).

Zoppi et al., "Iterative Design and Optimization of Initially Inactive Proteolysis Targeting Chimeras (PROTACs) Identify VZ185 as a Potent, Fast, and Selective von Hippel-Lindau (VHL) Based Dual Degrader Probe of BRD9 and BRD7," J Med Chem. 62(2):699-726 (2019).

U.S. Appl. No. 17/245,379, Sandoval et al.

Baheti et al., "Excipients used in lyophilization of small molecules," J. Excipients and Food Chem. 1(1):41-54 (2010).

Choi et al., "Correlation of computed tomography and positron emission tomography in patients with metastatic gastrointestinal stromal tumor treated at a single institution with imatinib mesylate: proposal of new computed tomography response criteria," J Clin Oncol. 25(13):1753-9 (May 1, 2007).

Extended European Search Report for European Patent Application No. 20749033.5, dated Sep. 29, 2022 (5 pages).

International Preliminary Report on Patentability for International Application No. PCT/US2020/015740, dated Jul. 27, 2021 (6 pages).

International Preliminary Report on Patentability for International Application No. PCT/US2020/044508, dated Feb. 10, 2022 (6 pages).

International Search Report and Written Opinion for International Application No. PCT/US20/44043, dated Nov. 9, 2020 (15 pages).

International Search Report and Written Opinion for International Application No. PCT/US20/44508, dated Jan. 12, 2021 (8 pages).

International Search Report and Written Opinion for International Application No. PCT/US20/15740, dated Jun. 26, 2020 (11 pages).

International Search Report and Written Opinion for International Application No. PCT/US21/15630, dated Apr. 8, 2021 (8 pages).

International Search Report and Written Opinion for International Application No. PCT/US22/36252, dated Nov. 15, 2022 (15 pages).

International Search Report and Written Opinion for International Application No. PCT/US22/38641, dated Nov. 17, 2022 (10 pages).

International Search Report and Written Opinion for International Application No. PCT/US22/38668 dated Jan. 20, 2023 (11 pages).

International Search Report and Written Opinion for PCT/US2022/028511, dated Aug. 1, 2022 (14 pages).

Kotla et al., "Mechanism of action of lenalidomide in hematological malignancies," J Hematol Oncol. 2:36 (Aug. 12, 2009).

Muscal et al., "Plasma and cerebrospinal fluid pharmacokinetics of thalidomide and lenalidomide in nonhuman primates," Available in PMC Jun. 18, 2013. Published in final edited form as: Cancer Chemother Pharmacol. 69(4):943-7 (Apr. 2012) (10 pages).

PubChem CID 68310947, "7-Methyl-4-phenyl-2H-isoquinolin-1-one," created Nov. 30, 2012 (8 pages).

Extended European Search Report for European Patent Application No. 20749034.3, dated Jan. 16, 2023 (9 pages).

International Preliminary Report on Patentability for International Patent Application No. PCT/US2020/015741, dated Jul. 27, 2021 (6 pages).

International Preliminary Report on Patentability for International Patent Application No. PCT/US2020/044043, dated Jan. 31, 2023 (7 pages).

(56) References Cited

OTHER PUBLICATIONS

International Search Report and Written Opinion for International Application No. PCT/US2020/015741, dated Jul. 20, 2020 (16 pages).
Partial Supplementary European Search Report for European Application No. 20749034.3, dated Oct. 11, 2022 (12 pages).
PubChem CID 12097004 "7-Phenyl-5H-furo[3,2-c] pyridin-4-one," created Feb. 7, 2007, retrieved Apr. 28, 2020 (9 pages).

\* cited by examiner

SYO1

HS-SY-II

ASKA

RD

HCT116

Calu6

COMPOUNDS AND USES THEREOF

BACKGROUND

Disorders can be affected by the BAF complex. BRD9 is a component of the BAF complex. The present invention relates to useful compositions and methods for the treatment of BAF complex-related disorders, such as cancer and infection.

SUMMARY

Bromodomain-containing protein 9 (BRD9) is a protein encoded by the BRD9 gene on chromosome 5. BRD9 is a component of the BAF (BRG1- or BRM-associated factors) complex, a SWI/SNF ATPase chromatin remodeling complex, and belongs to family IV of the bromodomain-containing proteins. BRD9 is present in several SWI/SNF ATPase chromatin remodeling complexes and is upregulated in multiple cancer cell lines. Accordingly, agents that reduce the levels and/or activity of BRD9 may provide new methods for the treatment of disease and disorders, such as cancer and infection. The inventors have found that depleting BRD9 in cells results in the depletion of the SS18-SSX fusion protein in those cells. The SS18-SSX fusion protein has been detected in more than 95% of synovial sarcoma tumors and is often the only cytogenetic abnormality in synovial sarcoma. Additionally, evidence suggests that the BAF complex is involved in cellular antiviral activities. Thus, agents that degrade BRD9 (e.g., compounds) are useful in the treatment of disorders (e.g., cancers or infections) related to BAF, BRD9, and/or SS18-SSX.

The present disclosure features compounds and methods useful for treating BAF-related disorders (e.g., cancer or infection).

In an aspect, the invention features a compound having the structure of any one of compounds D1, S-D1, R-D1, and D2 in Table 1, or a pharmaceutically acceptable salt thereof.

In some embodiments, the compound has the structure of compound D1, or a pharmaceutically acceptable salt thereof. In some embodiments, the compound has the structure of compound S-D1, or is a pharmaceutically acceptable salt thereof. In some embodiments, the compound has the structure of compound R-D1, or is a pharmaceutically acceptable salt thereof. In other embodiments, the compound has the structure of compound D2, or a pharmaceutically acceptable salt thereof.

In an aspect, the invention features a compound having the structure of compound D1 in Table 1, or a pharmaceutically acceptable salt thereof.

In an aspect, the invention features a compound having the structure of compound S-D1 in Table 1, or a pharmaceutically acceptable salt thereof.

In an aspect, the invention features a compound having the structure of compound R-D1 in Table 1, or a pharmaceutically acceptable salt thereof.

In another aspect, the invention features a compound having the structure of compound D2 in Table 1, or a pharmaceutically acceptable salt thereof.

TABLE 1

| Compound No. | Structure |
|---|---|
| D1 | (structure) |
| S-D1 | (structure) |

Compounds of the Invention

TABLE 1-continued

Compounds of the Invention

| Compound No. | Structure |
|---|---|
| R-D1 | 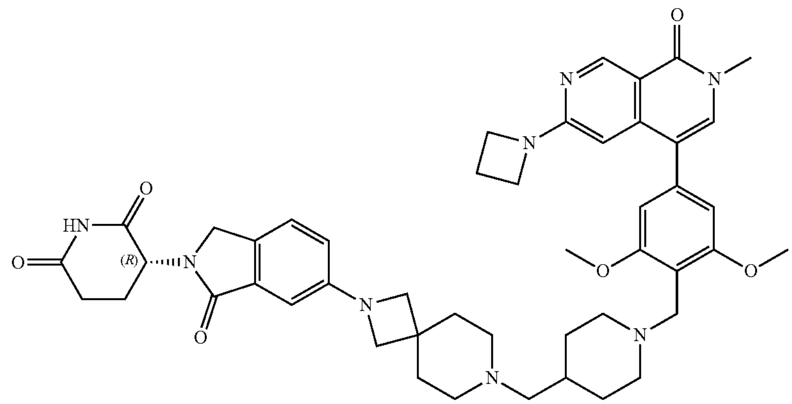 |
| D2 | 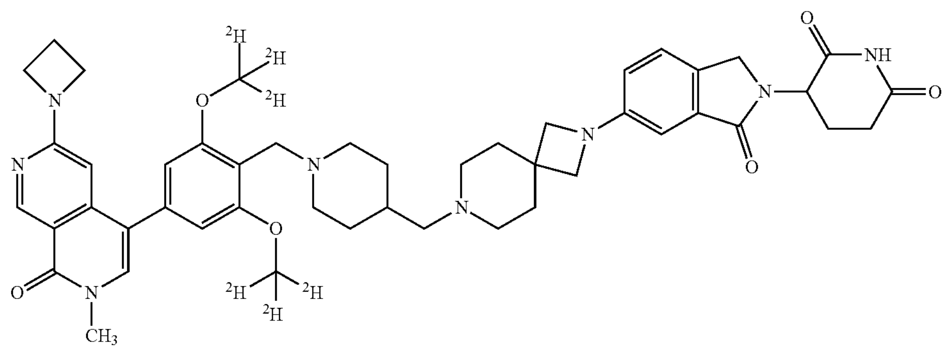 [SMILES: [2H]C([2H])([2H])Oc1cc(-c2cn(C)c(=O)c3cnc(N4CCC4)cc23)cc(OC([2H])([2H])[2H])c1CN1CCC(CN2CCC3(CC2)CN(c2ccc4c(c2)C(=O)N(C2CCC(=O)NC2=O)C4)C3)CC1] |

In another aspect, the disclosure features a pharmaceutical composition including any of the foregoing compounds, or pharmaceutically acceptable salts thereof, and a pharmaceutically acceptable excipient.

In an aspect, the disclosure features a method of inhibiting the level and/or activity of BRD9 in a cell, the method involving contacting the cell with an effective amount of any of the foregoing compounds, or pharmaceutically acceptable salts thereof, or a pharmaceutical composition thereof.

In another aspect, the disclosure features a method of reducing the level and/or activity of BRD9 in a cell, the method involving contacting the cell with an effective amount of any of the foregoing compounds, or pharmaceutically acceptable salts thereof, or a pharmaceutical composition thereof.

In some embodiments, the cell is a cancer cell.

In some embodiments, the cancer is a malignant, rhabdoid tumor, a CD8+ T-cell lymphoma, endometrial carcinoma, ovarian carcinoma, bladder cancer, stomach cancer, pancreatic cancer, esophageal cancer, prostate cancer, renal cell carcinoma, melanoma, colorectal cancer, a sarcoma (e.g., a soft tissue sarcoma, synovial sarcoma, Ewing's sarcoma, osteosarcoma, rhabdomyosarcoma, adult fibrosarcoma, alveolar soft-part sarcoma, angiosarcoma, clear cell sarcoma, desmoplastic small round cell tumor, epithelioid sarcoma, fibromyxoid sarcoma, gastrointestinal stromal tumor, Kaposi sarcoma, liposarcoma, leiomyosarcoma, malignant mesenchymoma malignant peripheral nerve sheath tumors, myxofibrosarcoma, low-grade rhabdomyosarcoma), non-small cell lung cancer (e.g., squamous or adenocarcinoma), stomach cancer, or breast cancer. In some embodiments, the cancer is a malignant, rhabdoid tumor, a CD8+ T-cell lymphoma, endometrial carcinoma, ovarian carcinoma, bladder cancer, stomach cancer, pancreatic cancer, esophageal cancer, prostate cancer, renal cell carcinoma, melanoma, or colorectal cancer. In some embodiments, the cancer is a sarcoma (e.g., synovial sarcoma or Ewing's sarcoma), non-small cell lung cancer (e.g., squamous or adenocarcinoma), stomach cancer, or breast cancer. In some embodiments, the cancer is sarcoma (e.g., synovial sarcoma or Ewing's sarcoma). In some embodiments, the sarcoma is synovial sarcoma.

In an aspect, the disclosure features a method of treating a BAF complex-related disorder in a subject in need thereof, the method involving administering to the subject an effective amount of any of the foregoing compounds, or pharmaceutically acceptable salts thereof, or a pharmaceutical composition thereof. In some embodiments, the BAF complex-related disorder is cancer. In some embodiments, the BAF complex-related disorder is infection.

In another aspect, the disclosure features a method of treating an SS18-SSX fusion protein-related disorder in a subject in need thereof, the method involving administering to the subject an effective amount of any of the foregoing compounds, or pharmaceutically acceptable salts thereof, or a pharmaceutical composition thereof. In some embodiments, the SS18-SSX fusion protein-related disorder is cancer. In some embodiments, the SS18-SSX fusion protein-related disorder is infection. In some embodiments of any of the foregoing methods, the SS18-SSX fusion protein is a SS18-SSX1 fusion protein, a SS18-SSX2 fusion protein, or a SS18-SSX4 fusion protein.

In yet another aspect, the disclosure features a method of treating a BRD9-related disorder in a subject in need thereof, the method involving administering to the subject an effective amount of any of the foregoing compounds, or pharmaceutically acceptable salts thereof, or a pharmaceutical composition thereof. In some embodiments, the BRD9-related disorder is cancer. In some embodiments, the BRD9-related disorder is infection.

In some embodiments, the cancer is squamous cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, glioblastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using the disclosed compounds according to the present invention include, for example, acute granulocytic leukemia, acute lymphocytic leukemia (ALL), acute myelogenous leukemia (AML), adenocarcinoma, adenosarcoma, adrenal cancer, adrenocortical carcinoma, anal cancer, anaplastic astrocytoma, angiosarcoma, appendix cancer, astrocytoma, Basal cell carcinoma, B-Cell lymphoma, bile duct cancer, bladder cancer, bone cancer, bone marrow cancer, bowel cancer, brain cancer, brain stem glioma, breast cancer, triple (estrogen, progesterone and HER-2) negative breast cancer, double negative breast cancer (two of estrogen, progesterone and HER-2 are negative), single negative (one of estrogen, progesterone and HER-2 is negative), estrogen-receptor positive, HER2-negative breast cancer, estrogen receptor-negative breast cancer, estrogen receptor positive breast cancer, metastatic breast cancer, luminal A breast cancer, luminal B breast cancer, Her2-negative breast cancer, HER2-positive or negative breast cancer, progesterone receptor-negative breast cancer, progesterone receptor-positive breast cancer, recurrent breast cancer, carcinoid tumors, cervical cancer, cholangiocarcinoma, chondrosarcoma, chronic lymphocytic leukemia (CLL), chronic myelogenous leukemia (CML), colon cancer, colorectal cancer, craniopharyngioma, cutaneous lymphoma, cutaneous melanoma, diffuse astrocytoma, ductal carcinoma in situ (DCIS), endometrial cancer, ependymoma, epithelioid sarcoma, esophageal cancer, ewing sarcoma, extrahepatic bile duct cancer, eye cancer, fallopian tube cancer, fibrosarcoma, gallbladder cancer, gastric cancer, gastrointestinal cancer, gastrointestinal carcinoid cancer, gastrointestinal stromal tumors (GIST), germ cell tumor glioblastoma multiforme (GBM), glioma, hairy cell leukemia, head and neck cancer, hemangioendothelioma, Hodgkin lymphoma, hypopharyngeal cancer, infiltrating ductal carcinoma (IDC), infiltrating lobular carcinoma (ILC), inflammatory breast cancer (IBC), intestinal Cancer, intrahepatic bile duct cancer, invasive/infiltrating breast cancer, Islet cell cancer, jaw cancer, Kaposi sarcoma, kidney cancer, laryngeal cancer, leiomyosarcoma, leptomeningeal metastases, leukemia, lip cancer, liposarcoma, liver cancer, lobular carcinoma in situ, low-grade astrocytoma, lung cancer, lymph node cancer, lymphoma, male breast cancer, medullary carcinoma, medulloblastoma, melanoma, meningioma, Merkel cell carcinoma, mesenchymal chondrosarcoma, mesenchymous, mesothelioma metastatic breast cancer, metastatic melanoma metastatic squamous neck cancer, mixed gliomas, monodermal teratoma, mouth cancer mucinous carcinoma, mucosal melanoma, multiple myeloma, Mycosis Fungoides, myelodysplastic syndrome, nasal cavity cancer, nasopharyngeal cancer, neck cancer, neuroblastoma, neuroendocrine tumors (NETs), non-Hodgkin's lymphoma, non-small cell lung cancer (NSCLC), oat cell cancer, ocular cancer, ocular melanoma, oligodendroglioma, oral cancer, oral cavity cancer, oropharyngeal cancer, osteogenic sarcoma, osteosarcoma, ovarian cancer, ovarian epithelial cancer ovarian germ cell tumor, ovarian primary peritoneal carcinoma, ovarian sex cord stromal tumor, Paget's disease, pancreatic cancer, papillary carcinoma, paranasal sinus cancer, parathyroid cancer, pelvic cancer, penile cancer, peripheral nerve cancer, peritoneal cancer, pharyngeal cancer, pheochromocytoma, pilocytic astrocytoma, pineal region tumor, pineoblastoma, pituitary gland cancer, primary central nervous system (CNS) lymphoma, prostate cancer, rectal cancer, renal cell carcinoma, renal pelvis cancer, rhabdomyosarcoma, salivary gland cancer, soft tissue sarcoma, bone sarcoma, sarcoma, sinus cancer, skin cancer, small cell lung cancer (SCLC), small intestine cancer, spinal cancer, spinal column cancer, spinal cord cancer, squamous cell carcinoma, stomach cancer, synovial sarcoma, T-cell lymphoma, testicular cancer, throat cancer, thymoma/thymic carcinoma, thyroid cancer, tongue cancer, tonsil cancer, transitional cell cancer, tubal cancer, tubular carcinoma, undiagnosed cancer, ureteral cancer, urethral cancer, uterine adenocarcinoma, uterine cancer, uterine sarcoma, vaginal cancer, vulvar cancer, T-cell lineage acute lymphoblastic leukemia (T-ALL), T-cell lineage lymphoblastic lymphoma (T-LL), peripheral T-cell lymphoma, Adult T-cell leukemia, Pre-B ALL, Pre-B lymphomas, large B-cell lymphoma, Burkitts lymphoma, B-cell ALL, Philadelphia chromosome positive ALL, Philadelphia chromosome positive CML, juvenile myelomonocytic leukemia (JMML), acute promyelocytic leukemia (a subtype of AML), large granular lymphocytic leukemia, Adult T-cell chronic leukemia, diffuse large B cell lymphoma, follicular lymphoma; Mucosa-Associated Lymphatic Tissue lymphoma (MALT), small cell lymphocytic lymphoma, mediastinal large B cell lymphoma, nodal marginal zone B cell lymphoma (NMZL); splenic marginal zone lymphoma (SMZL); intravascular large B-cell lymphoma; primary effusion lymphoma; or lymphomatoid granulomatosis; B-cell prolymphocytic leukemia; splenic lymphoma/leukemia, unclassifiable, splenic diffuse red pulp small B-cell lymphoma; lymphoplasmacytic lymphoma; heavy chain diseases, for example, Alpha heavy chain disease, Gamma heavy chain disease, Mu heavy chain disease, plasma cell myeloma, solitary plasmacytoma of bone; extraosseous plasmacytoma; primary cutaneous follicle center lymphoma, T cell/histocyte rich large B-cell lymphoma, DLBCL associated with chronic inflammation; Epstein-Barr virus (EBV)+ DLBCL of the elderly; primary mediastinal (thymic) large B-cell lymphoma, primary cutaneous DLBCL, leg type, ALK+ large B-cell lymphoma, plasmablastic lymphoma; large B-cell lymphoma arising in HHV8-associated multicentric, Castleman disease; B-cell lymphoma, unclassifiable, with features intermediate between diffuse large B-cell lymphoma, or B-cell lymphoma, unclassifiable, with features intermediate between diffuse large B-cell lymphoma and classical Hodgkin lymphoma.

In some embodiments, the cancer is a malignant, rhabdoid tumor, a CD8+ T-cell lymphoma, endometrial carcinoma, ovarian carcinoma, bladder cancer, stomach cancer, pancreatic cancer, esophageal cancer, prostate cancer, renal cell carcinoma, melanoma, colorectal cancer, a sarcoma (e.g., a soft tissue sarcoma, synovial sarcoma, Ewing's sarcoma, osteosarcoma, rhabdomyosarcoma, adult fibrosarcoma, alveolar soft-part sarcoma, angiosarcoma, clear cell sarcoma, desmoplastic small round cell tumor, epithelioid sarcoma, fibromyxoid sarcoma, gastrointestinal stromal tumor, Kaposi sarcoma, liposarcoma, leiomyosarcoma, malignant mesenchymoma malignant peripheral nerve sheath tumors, myxofibrosarcoma, low-grade rhabdomyosarcoma), non-small cell lung cancer (e.g., squamous or adenocarcinoma), stomach cancer, or breast cancer. In some embodiments, the cancer is a malignant, rhabdoid tumor, a CD8+ T-cell lymphoma, endometrial carcinoma, ovarian carcinoma, bladder cancer, stomach cancer, pancreatic cancer, esophageal cancer, prostate cancer, renal cell carcinoma, melanoma, or colorectal cancer. In some embodiments, the cancer is a sarcoma (e.g., synovial sarcoma or Ewing's sarcoma), non-small cell lung cancer (e.g., squamous or adenocarcinoma), stomach cancer, or breast cancer. In some embodiments, the cancer is sarcoma (e.g., synovial sarcoma or Ewing's sarcoma). In some embodiments, the sarcoma is synovial sarcoma.

In some embodiments, the infection is viral infection (e.g., an infection with a virus of the Retroviridae family such as the lentiviruses (e.g. Human immunodeficiency virus (HIV) and deltaretroviruses (e.g., human T cell leukemia virus I (HTLV-I), human T cell leukemia virus II (HTLV-II)); Hepadnaviridae family (e.g. hepatitis B virus (HBV)); Flaviviridae family (e.g. hepatitis C virus (HCV)); Adenoviridae family (e.g. Human Adenovirus); Herpesviridae family (e.g. Human cytomegalovirus (HCMV), Epstein-Barr virus, herpes simplex virus 1 (HSV-1), herpes simplex virus 2 (HSV-2), human herpesvirus 6 (HHV-6), Herpesvitus K*, CMV, varicella-zoster virus); Papillomaviridae family (e.g. Human Papillomavirus (HPV, HPV E1)); Parvoviridae family (e.g. Parvovirus B19); Polyomaviridae family (e.g. JC virus and BK virus); Paramyxoviridae family (e.g. Measles virus); or Togaviridae family (e.g. Rubella virus)). In some embodiments, the disorder is Coffin Siris, Neurofibromatosis (e.g., NF-1, NF-2, or Schwannomatosis), or Multiple Meningioma. In an aspect, the disclosure features a method of treating a cancer in a subject in need thereof, the method including administering to the subject an effective amount of any of the foregoing compounds, or pharmaceutically acceptable salts thereof, or any of the foregoing pharmaceutical compositions.

In some embodiments, the cancer is squamous cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, glioblastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using the disclosed compounds according to the present invention include, for example, acute granulocytic leukemia, acute lymphocytic leukemia (ALL), acute myelogenous leukemia (AML), adenocarcinoma, adenosarcoma, adrenal cancer, adrenocortical carcinoma, anal cancer, anaplastic astrocytoma, angiosarcoma, appendix cancer, astrocytoma, Basal cell carcinoma, B-Cell lymphoma, bile duct cancer, bladder cancer, bone cancer, bone marrow cancer, bowel cancer, brain cancer, brain stem glioma, breast cancer, triple (estrogen, progesterone and HER-2) negative breast cancer, double negative breast cancer (two of estrogen, progesterone and HER-2 are negative), single negative (one of estrogen, progesterone and HER-2 is negative), estrogen-receptor positive, HER2-negative breast cancer, estrogen receptor-negative breast cancer, estrogen receptor positive breast cancer, metastatic breast cancer, luminal A breast cancer, luminal B breast cancer, Her2-negative breast cancer, HER2-positive or negative breast cancer, progesterone receptor-negative breast cancer, progesterone receptor-positive breast cancer, recurrent breast cancer, carcinoid tumors, cervical cancer, cholangiocarcinoma, chondrosarcoma, chronic lymphocytic leukemia (CLL), chronic myelogenous leukemia (CML), colon cancer, colorectal cancer, craniopharyngioma, cutaneous lymphoma, cutaneous melanoma, diffuse astrocytoma, ductal carcinoma in situ (DCIS), endometrial cancer, ependymoma, epithelioid sarcoma, esophageal cancer, ewing sarcoma, extrahepatic bile duct cancer, eye cancer, fallopian tube cancer, fibrosarcoma, gallbladder cancer, gastric cancer, gastrointestinal cancer, gastrointestinal carcinoid cancer, gastrointestinal stromal tumors (GIST), germ cell tumor glioblastoma multiforme (GBM), glioma, hairy cell leukemia, head and neck cancer, hemangioendothelioma, Hodgkin lymphoma, hypopharyngeal cancer, infiltrating ductal carcinoma (IDC), infiltrating lobular carcinoma (ILC), inflammatory breast cancer (IBC), intestinal Cancer, intrahepatic bile duct cancer, invasive/infiltrating breast cancer, Islet cell cancer, jaw cancer, Kaposi sarcoma, kidney cancer, laryngeal cancer, leiomyosarcoma, leptomeningeal metastases, leukemia, lip cancer, liposarcoma, liver cancer, lobular carcinoma in situ, low-grade astrocytoma, lung cancer, lymph node cancer, lymphoma, male breast cancer, medullary carcinoma, medulloblastoma, melanoma, meningioma, Merkel cell carcinoma, mesenchymal chondrosarcoma, mesenchymous, mesothelioma metastatic breast cancer, metastatic melanoma metastatic squamous neck cancer, mixed gliomas, monodermal teratoma, mouth cancer mucinous carcinoma, mucosal melanoma, multiple myeloma, Mycosis Fungoides, myelodysplastic syndrome, nasal cavity cancer, nasopharyngeal cancer, neck cancer, neuroblastoma, neuroendocrine tumors (NETs), non-Hodgkin's lymphoma, non-small cell lung cancer (NSCLC), oat cell cancer, ocular cancer, ocular melanoma, oligodendroglioma, oral cancer, oral cavity cancer, oropharyngeal cancer, osteogenic sarcoma, osteosarcoma, ovarian cancer, ovarian epithelial cancer ovarian germ cell tumor, ovarian primary peritoneal carcinoma, ovarian sex cord stromal tumor, Paget's disease, pancreatic cancer, papillary carcinoma, paranasal sinus cancer, parathyroid cancer, pelvic cancer, penile cancer, peripheral nerve cancer, peritoneal cancer, pharyngeal cancer, pheochromocytoma, pilocytic astrocytoma, pineal region tumor, pineoblastoma, pituitary gland cancer, primary central nervous system (CNS) lymphoma, prostate cancer, rectal cancer, renal cell carcinoma, renal pelvis cancer, rhabdomyosarcoma, salivary gland cancer, soft tissue sarcoma, bone sarcoma, sarcoma, sinus cancer, skin cancer, small cell lung cancer (SCLC), small intestine cancer, spinal cancer, spinal column cancer, spinal cord cancer, squamous cell carcinoma, stomach cancer, synovial sarcoma, T-cell lymphoma, testicular cancer, throat cancer, thymoma/thymic carcinoma, thyroid cancer, tongue cancer, tonsil cancer, transitional cell cancer, tubal cancer, tubular carcinoma, undiagnosed cancer, ureteral cancer, urethral cancer, uterine adenocarcinoma, uterine cancer, uterine sarcoma, vaginal cancer, vulvar cancer, T-cell lineage acute lymphoblastic leukemia (T-ALL), T-cell lineage lymphoblastic lymphoma (T-LL), peripheral T-cell lymphoma, Adult T-cell leukemia, Pre-B ALL, Pre-B lymphomas, large B-cell lymphoma, Burkitts lymphoma, B-cell ALL, Philadelphia chromosome positive ALL, Philadelphia chromosome positive CML, juvenile myelomonocytic leukemia (JMML), acute promyelocytic leukemia (a subtype of AML), large granular lymphocytic leukemia, Adult T-cell chronic leukemia, diffuse large B cell lymphoma, follicular lymphoma; Mucosa-Associated Lymphatic Tissue lymphoma (MALT), small cell lymphocytic lymphoma, mediastinal large B cell lymphoma, nodal marginal zone B cell lymphoma (NMZL); splenic marginal zone lymphoma (SMZL); intravascular large B-cell lymphoma; primary effusion lymphoma; or lymphomatoid granulomatosis; B-cell prolymphocytic leukemia; splenic lymphoma/leukemia, unclassifiable, splenic diffuse red pulp small B-cell lymphoma; lymphoplasmacytic lymphoma; heavy chain diseases, for example, Alpha heavy chain disease, Gamma heavy chain disease, Mu heavy chain disease, plasma cell myeloma, solitary plasmacytoma of bone; extraosseous plasmacytoma; primary cutaneous follicle center lymphoma, T cell/histocyte rich large B-cell lymphoma, DLBCL associated with chronic inflammation; Epstein-Barr virus (EBV)+ DLBCL of the elderly; primary mediastinal (thymic) large B-cell lymphoma, primary cutaneous DLBCL, leg type, ALK+ large B-cell lymphoma, plasmablastic lymphoma; large B-cell lymphoma arising in HHV8-associated multicentric, Castleman disease; B-cell lymphoma, unclassifiable, with features intermediate between diffuse large B-cell lymphoma, or B-cell lymphoma, unclassifiable, with features intermediate between diffuse large B-cell lymphoma and classical Hodgkin lymphoma.

In some embodiments, the cancer is a malignant, rhabdoid tumor, a CD8+ T-cell lymphoma, endometrial carcinoma, ovarian carcinoma, bladder cancer, stomach cancer, pancreatic cancer, esophageal cancer, prostate cancer, renal cell carcinoma, melanoma, colorectal cancer, a sarcoma (e.g., a soft tissue sarcoma, synovial sarcoma, Ewing's sarcoma, osteosarcoma, rhabdomyosarcoma, adult fibrosarcoma, alveolar soft-part sarcoma, angiosarcoma, clear cell sarcoma, desmoplastic small round cell tumor, epithelioid sarcoma, fibromyxoid sarcoma, gastrointestinal stromal tumor, Kaposi sarcoma, liposarcoma, leiomyosarcoma, malignant mesenchymoma malignant peripheral nerve sheath tumors, myxofibrosarcoma, low-grade rhabdomyosarcoma), non-small cell lung cancer (e.g., squamous or adenocarcinoma), stomach cancer, or breast cancer. In some embodiments, the cancer is a malignant, rhabdoid tumor, a CD8+ T-cell lymphoma, endometrial carcinoma, ovarian carcinoma, bladder cancer, stomach cancer, pancreatic cancer, esophageal cancer, prostate cancer, renal cell carcinoma, melanoma, or colorectal cancer. In some embodiments, the cancer is a sarcoma (e.g., synovial sarcoma or Ewing's sarcoma), non-small cell lung cancer (e.g., squamous or adenocarcinoma), stomach cancer, or breast cancer. In some embodiments, the cancer is sarcoma (e.g., synovial sarcoma or Ewing's sarcoma). In some embodiments, the sarcoma is synovial sarcoma.

In some embodiments of any of the foregoing methods, the cancer is a prostate cancer. In some embodiments of any of the foregoing methods, the cancer is a prostate cancer.

In some embodiments of any of the foregoing methods, the cancer is a BRCA mutated cancer.

In another aspect, the disclosure features a method for treating a viral infection in a subject in need thereof. This method includes administering to the subject an effective amount of any of the foregoing compounds, or pharmaceutically acceptable salts thereof, or any of the foregoing pharmaceutical compositions. In some embodiments, the viral infection is an infection with a virus of the Retroviridae family such as the lentiviruses (e.g. Human immunodeficiency virus (HIV) and deltaretroviruses (e.g., human T cell leukemia virus I (HTLV-I), human T cell leukemia virus II (HTLV-II)); Hepadnaviridae family (e.g. hepatitis B virus (HBV)), Flaviviridae family (e.g. hepatitis C virus (HCV)), Adenoviridae family (e.g. Human Adenovirus), Herpesviridae family (e.g. Human cytomegalovirus (HCMV), Epstein-Barr virus, herpes simplex virus 1 (HSV-1), herpes simplex virus 2 (HSV-2), human herpesvirus 6 (HHV-6), Herpesvitus K*, CMV, varicella-zoster virus), Papillomaviridae family (e.g. Human Papillomavirus (HPV, HPV E1)), Parvoviridae family (e.g. Parvovirus B19), Polyomaviridae family (e.g. JC virus and BK virus), Paramyxoviridae family (e.g. Measles virus), Togaviridae family (e.g. Rubella virus).

In another embodiment of any of the foregoing methods, the method further includes administering to the subject an additional anticancer therapy (e.g., chemotherapeutic or cytotoxic agent or radiotherapy).

In some embodiments, the additional anticancer therapy is a PARP inhibitor (e.g., niraparib, olaparib, rucaparib, talazoparib, veliparib, pamiparib, CK-102, or E7016). In particular embodiments, the additional anticancer therapy is: a chemotherapeutic or cytotoxic agent (e.g., doxorubicin or ifosfamide), a differentiation-inducing agent (e.g., retinoic acid, vitamin D, cytokines), a hormonal agent, an immunological agent, or an anti-angiogenic agent. Chemotherapeutic and cytotoxic agents, but are not limited to, alkylating agents, cytotoxic antibiotics, antimetabolites, vinca alkaloids, etoposides, and others (e.g., paclitaxel, taxol, docetaxel, taxotere, cis-platinum). A list of additional compounds having anticancer activity can be found in L. Brunton, B. Chabner and B. Knollman (eds). Goodman and Gilman's The Pharmacological Basis of Therapeutics, Twelfth Edition, 2011, McGraw Hill Companies, New York, N.Y.

In particular embodiments, the compound of the invention and the additional anticancer therapy and any of the foregoing compounds or pharmaceutical compositions are administered within 28 days of each other (e.g., within 21, 14, 10, 7, 5, 4, 3, 2, or 1 days) or within 24 hours (e.g., 12, 6, 3, 2, or 1 hours; or concomitantly) each in an amount that together are effective to treat the subject.

Chemical Terms

Compounds described herein can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates, or mixtures of diastereoisomeric racemates. The optically active forms can be obtained for example by resolution of the racemates, by asymmetric synthesis or asymmetric chromatography (chromatography with a chiral adsorbent or eluant). That is, certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms and represent the configuration of substituents around one or more chiral carbon atoms. Enantiomers of a compound can be prepared, for example, by separating an enantiomer from a racemate using one or more well-known techniques and methods, such as, for example, chiral chromatography and separation methods based thereon. The appropriate technique and/or method for separating an enantiomer of a compound described herein from a racemic mixture can be readily determined by those of skill in the art. "Racemate" or "racemic mixture" means a compound containing two enantiomers, wherein such mixtures exhibit no optical activity; i.e., they do not rotate the plane of polarized light. "Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration. "R," "S," "S*," "R*," "E," "Z," "cis," and "trans," indicate configurations relative to the core molecule. Certain of the disclosed compounds may exist in atropisomeric forms. Atropisomers are stereoisomers resulting from hindered rotation about single bonds where the steric strain barrier to rotation is high enough to allow for the isolation of the conformers. The compounds described herein may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods. When the stereochemistry of a disclosed compound is named or depicted by structure, the named or depicted stereoisomer is at least 60%, 70%, 80%, 90%, 99%, or 99.9% by weight relative to the other stereoisomers. When a single enantiomer is named or depicted by structure, the depicted or named enantiomer is at least 60%, 70%, 80%, 90%, 99%, or 99.9% by weight optically pure. When a single diastereomer is named or depicted by structure, the depicted or named diastereomer is at least 60%, 70%, 80%, 90%, 99%, or 99.9% by weight pure. Percent optical purity is the ratio of the weight of the enantiomer or over the weight of the enantiomer plus the weight of its optical isomer. Diastereomeric purity by weight is the ratio of the weight of one diastereomer or over the weight of all the diastereomers. When the stereochemistry of a disclosed compound is named or depicted by structure, the named or depicted stereoisomer is at least 60%, 70%, 80%, 90%, 99%, or 99.9% by mole fraction pure relative to the other stereoisomers. When a single enantiomer is named or depicted by structure, the depicted or named enantiomer is at least 60%, 70%, 80%, 90%, 99%, or 99.9% by mole fraction pure. When a single diastereomer is named or depicted by structure, the depicted or named diastereomer is at least 60%, 70%, 80%, 90%, 99%, or 99.9% by mole fraction pure. Percent purity by mole fraction is the ratio of the moles of the enantiomer or over the moles of the enantiomer plus the moles of its optical isomer. Similarly, percent purity by moles fraction is the ratio of the moles of the diastereomer or over the moles of the diastereomer plus the moles of its isomer. When a disclosed compound is named or depicted by structure without indicating the stereochemistry, and the compound has at least one chiral center, it is to be understood that the name or structure encompasses either enantiomer of the compound free from the corresponding optical isomer, a racemic mixture of the compound, or mixtures enriched in one enantiomer relative to its corresponding optical isomer. When a disclosed compound is named or depicted by structure without indicating the stereochemistry and has two or more chiral centers, it is to be understood that the name or structure encompasses a diastereomer free of other diastereomers, a number of diastereomers free from other diastereomeric pairs, mixtures of diastereomers, mixtures of diastereomeric pairs, mixtures of diastereomers in which one diastereomer is enriched relative to the other diastereomer(s), or mixtures of diastereomers in which one or more diastereomer is enriched relative to the other diastereomers. The invention embraces all of these forms.

Compounds of the present disclosure also include all of the isotopes of the atoms occurring in the intermediate or final compounds. "Isotopes" refers to atoms having the same atomic number but different mass numbers resulting from a different number of neutrons in the nuclei. For example, isotopes of hydrogen include tritium and deuterium.

Unless otherwise stated, structures depicted herein are also meant to include compounds that differ only in the presence of one or more isotopically enriched atoms. Exemplary isotopes that can be incorporated into compounds of the present invention include isotopes of hydrogen, carbon, nitrogen, oxygen, phosphorus, sulfur, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Isotopically-labeled compounds (e.g., those labeled with $^{3}H$ and $^{14}C$) can be useful in compound or substrate tissue distribution assays. Tritiated (i.e., $^{3}H$) and carbon-14 (i.e., $^{14}C$)) isotopes can be useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements). In some embodiments, one or more hydrogen atoms are replaced by $^{2}H$ or $^{3}H$, or one or more carbon atoms are replaced by $^{13}C$- or $^{14}C$-enriched carbon. Positron emitting isotopes such as $^{15}O$, $^{13}N$, $^{11}C$, and $^{18}F$ are useful for positron emission tomography (PET) studies to examine substrate receptor occupancy. Preparations of isotopically labelled compounds are known to those of skill in the art. For example, isotopically labeled compounds can generally be prepared by following procedures analogous to those disclosed for compounds of the present invention described herein, by substituting an isotopically labeled reagent for a non-isotopically labeled reagent.

As is known in the art, many chemical entities can adopt a variety of different solid forms such as, for example, amorphous forms or crystalline forms (e.g., polymorphs, hydrates, solvate). In some embodiments, compounds of the present invention may be utilized in any such form, including in any solid form. In some embodiments, compounds described or depicted herein may be provided or utilized in hydrate or solvate form.

Unless otherwise defined, all technical and scientific terms used herein have the same meaning as commonly understood by one of ordinary skill in the art to which this invention belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Definitions

In this application, unless otherwise clear from context, (i) the term "a" may be understood to mean "at least one"; (ii) the term "or" may be understood to mean "and/or"; and (iii) the terms "including" and "including" may be understood to encompass itemized components or steps whether presented by themselves or together with one or more additional components or steps.

As used herein, the terms "about" and "approximately" refer to a value that is within 10% above or below the value being described. For example, the term "about 5 nM" indicates a range of from 4.5 to 5.5 nM.

As used herein, the term "administration" refers to the administration of a composition (e.g., a compound or a preparation that includes a compound as described herein) to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intratumoral, intravenous, intraventricular, mucosal, nasal, oral, rectal, subcutaneous, sublingual, topical, tracheal (including by intratracheal instillation), transdermal, vaginal, and vitreal.

As used herein, the term "adult soft tissue sarcoma" refers to a sarcoma that develops in the soft tissues of the body, typically in adolescent and adult subjects (e.g., subjects who are at least 10 years old, 11 years old, 12 years old, 13 years old, 14 years old, 15 years old, 16 years old, 17 years old, 18 years old, or 19 years old). Non-limiting examples of adult soft tissue sarcoma include, but are not limited to, synovial sarcoma, fibrosarcoma, malignant fibrous histiocytoma, dermatofibrosarcoma, liposarcoma, leiomyosarcoma, hemangiosarcoma, Kaposi's sarcoma, lymphangiosarcoma, malignant peripheral nerve sheath tumor/neurofibrosarcoma, extraskeletal chondrosarcoma, extraskeletal osteosarcoma, extraskeletal myxoid chondrosarcoma, and extraskeletal mesenchymal.

As used herein, the term "BAF complex" refers to the BRG1- or HRBM-associated factors complex in a human cell.

As used herein, the term "BAF complex-related disorder" refers to a disorder that is caused or affected by the level and/or activity of a BAF complex.

As used herein, the terms "GBAF complex" and "GBAF" refer to a SWI/SNF ATPase chromatin remodeling complex in a human cell. GBAF complex subunits may include, but are not limited to, ACTB, ACTL6A, ACTL6B, BICRA, BICRAL, BRD9, SMARCA2, SMARCA4, SMARCC1, SMARCD1, SMARCD2, SMARCD3, and SS18. The term "cancer" refers to a condition caused by the proliferation of malignant neoplastic cells, such as tumors, neoplasms, carcinomas, sarcomas, leukemias, and lymphomas.

As used herein, the term "BRD9" refers to bromodomain-containing protein 9, a component of the BAF (BRG1- or BRM-associated factors) complex, a SWI/SNF ATPase chromatin remodeling complex, and belongs to family IV of the bromodomain-containing proteins. BRD9 is encoded by the BRD9 gene, the nucleic acid sequence of which is set forth in SEQ ID NO: 1. The term "BRD9" also refers to natural variants of the wild-type BRD9 protein, such as proteins having at least 85% sequence identity (e.g., 85%, 86%, 87%, 88%, 89%, 90%, 91%, 92%, 93%, 94%, 95%, 96%, 97%, 98%, 99%, 99.9% identity, or more) to the amino acid sequence of wild-type BRD9, which is set forth in SEQ ID NO: 2.

As used herein, the term "BRD9-related disorder" refers to a disorder that is caused or affected by the level and/or activity of BRD9. The term "cancer" refers to a condition caused by the proliferation of malignant neoplastic cells, such as tumors, neoplasms, carcinomas, sarcomas, leukemias, and lymphomas.

As used herein, a "combination therapy" or "administered in combination" means that two (or more) different agents or treatments are administered to a subject as part of a defined treatment regimen for a particular disease or condition. The treatment regimen defines the doses and periodicity of administration of each agent such that the effects of the separate agents on the subject overlap. In some embodiments, the delivery of the two or more agents is simultaneous or concurrent and the agents may be co-formulated. In some embodiments, the two or more agents are not co-formulated and are administered in a sequential manner as part of a prescribed regimen. In some embodiments, administration of two or more agents or treatments in combination is such that the reduction in a symptom, or other parameter related to the disorder is greater than what would be observed with one agent or treatment delivered alone or in the absence of the other. The effect of the two treatments can be partially additive, wholly additive, or greater than additive (e.g., synergistic). Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination may be administered by intravenous injection while a second therapeutic agent of the combination may be administered orally.

A "compound of the present invention" and similar terms as used herein, whether explicitly noted or not, refers to compounds useful for treating BAF-related disorders (e.g., cancer or infection) described herein, including, e.g., compound D1, compound S-D1, compound R-D1, or compound D2, as well as salts (e.g., pharmaceutically acceptable salts), solvates, hydrates, stereoisomers (including atropisomers), and tautomers thereof. Those skilled in the art will appreciate that certain compounds described herein can exist in one or more different isomeric (e.g., stereoisomers, geometric isomers, atropisomers, and tautomers) or isotopic (e.g., in which one or more atoms has been substituted with a different isotope of the atom, such as hydrogen substituted for deuterium) forms. Unless otherwise indicated or clear from context, a depicted structure can be understood to represent any such isomeric or isotopic form, individually or in combination. Compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms. In some embodiments, one or more compounds depicted herein may exist in different tautomeric forms. As will be clear from context, unless explicitly excluded, references to such compounds encompass all such tautomeric forms. In some embodiments, tautomeric forms result from the swapping of a single bond with an adjacent double bond and the concomitant migration of a proton. In certain embodiments, a tautomeric form may be a prototropic tautomer, which is an isomeric protonation states having the same empirical formula and total charge as a reference form. Examples of moieties with prototropic tautomeric forms are ketone-enol pairs, amide-imidic acid pairs, lactam-lactim pairs, amide-imidic acid pairs, enamine-imine pairs, and annular forms where a proton can occupy two or more positions of a heterocyclic system, such as, 1H- and 3H-imidazole, 1H-, 2H- and 4H-1,2,4-triazole, 1H- and 2H-isoindole, and 1H- and 2H-pyrazole. In some embodiments, tautomeric forms can be in equilibrium or sterically locked into one form by appropriate substitution. In certain embodiments, tautomeric forms result from acetal interconversion.

As used herein, the term "degrader" refers to a small molecule compound including a degradation moiety, wherein the compound interacts with a protein (e.g., BRD9) in a way which results in degradation of the protein, e.g., binding of the compound results in at least 5% reduction of the level of the protein, e.g., in a cell or subject.

As used herein, the term "degradation moiety" refers to a moiety whose binding results in degradation of a protein, e.g., BRD9. In one example, the moiety binds to a protease or a ubiquitin ligase that metabolizes the protein, e.g., BRD9.

By "determining the level of a protein" is meant the detection of a protein, or an mRNA encoding the protein, by methods known in the art either directly or indirectly. "Directly determining" means performing a process (e.g., performing an assay or test on a sample or "analyzing a sample" as that term is defined herein) to obtain the physical entity or value. "Indirectly determining" refers to receiving the physical entity or value from another party or source (e.g., a third-party laboratory that directly acquired the physical entity or value). Methods to measure protein level generally include, but are not limited to, western blotting, immunoblotting, enzyme-linked immunosorbent assay (ELISA), radioimmunoassay (RIA), immunoprecipitation, immunofluorescence, surface plasmon resonance, chemiluminescence, fluorescent polarization, phosphorescence, immunohistochemical analysis, matrix-assisted laser desorption/ionization time-of-flight (MALDI-TOF) mass spectrometry, liquid chromatography (LC)-mass spectrometry, microcytometry, microscopy, fluorescence activated cell sorting (FACS), and flow cytometry, as well as assays based on a property of a protein including, but not limited to, enzymatic activity or interaction with other protein partners. Methods to measure mRNA levels are known in the art.

As used herein, the terms "effective amount," "therapeutically effective amount," and "a "sufficient amount" of an agent that reduces the level and/or activity of BRD9 (e.g., in a cell or a subject) described herein refer to a quantity sufficient to, when administered to the subject, including a human, effect beneficial or desired results, including clinical results, and, as such, an "effective amount" or synonym thereto depends on the context in which it is being applied. For example, in the context of treating cancer, it is an amount of the agent that reduces the level and/or activity of BRD9 sufficient to achieve a treatment response as compared to the response obtained without administration of the agent that reduces the level and/or activity of BRD9. The amount of a given agent that reduces the level and/or activity of BRD9 described herein that will correspond to such an amount will vary depending upon various factors, such as the given agent, the pharmaceutical formulation, the route of administration, the type of disease or disorder, the identity of the subject (e.g., age, sex, and/or weight) or host being treated, and the like, but can nevertheless be routinely determined by one of skill in the art. Also, as used herein, a "therapeutically effective amount" of an agent that reduces the level and/or activity of BRD9 of the present disclosure is an amount which results in a beneficial or desired result in a subject as compared to a control. As defined herein, a therapeutically effective amount of an agent that reduces the level and/or activity of BRD9 of the present disclosure may be readily determined by one of ordinary skill by routine methods known in the art. Dosage regimen may be adjusted to provide the optimum therapeutic response.

As used herein, the term "inhibitor" refers to any agent which reduces the level and/or activity of a protein (e.g., BRD9). Non-limiting examples of inhibitors include small molecule inhibitors, degraders, antibodies, enzymes, or polynucleotides (e.g., siRNA).

By "level" is meant a level of a protein, or mRNA encoding the protein, as compared to a reference. The reference can be any useful reference, as defined herein. By a "decreased level" or an "increased level" of a protein is meant a decrease or increase in protein level, as compared to a reference (e.g., a decrease or an increase by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 300%, about 400%, about 500%, or more; a decrease or an increase of more than about 10%, about 15%, about 20%, about 50%, about 75%, about 100%, or about 200%, as compared to a reference; a decrease or an increase by less than about 0.01-fold, about 0.02-fold, about 0.1-fold, about 0.3-fold, about 0.5-fold, about 0.8-fold, or less; or an increase by more than about 1.2-fold, about 1.4-fold, about 1.5-fold, about 1.8-fold, about 2.0-fold, about 3.0-fold, about 3.5-fold, about 4.5-fold, about 5.0-fold, about 10-fold, about 15-fold, about 20-fold, about 30-fold, about 40-fold, about 50-fold, about 100-fold, about 1000-fold, or more). A level of a protein may be expressed in mass/vol (e.g., g/dL, mg/mL, µg/mL, ng/mL) or percentage relative to total protein or mRNA in a sample.

By "modulating the activity of a BAF complex," is meant altering the level of an activity related to a BAF complex (e.g., GBAF), or a related downstream effect. The activity level of a BAF complex may be measured using any method known in the art, e.g., the methods described in Kadoch et al, Cell 153:71-85 (2013), the methods of which are herein incorporated by reference.

"Percent (%) sequence identity" with respect to a reference polynucleotide or polypeptide sequence is defined as the percentage of nucleic acids or amino acids in a candidate sequence that are identical to the nucleic acids or amino acids in the reference polynucleotide or polypeptide sequence, after aligning the sequences and introducing gaps, if necessary, to achieve the maximum percent sequence identity. Alignment for purposes of determining percent nucleic acid or amino acid sequence identity can be achieved in various ways that are within the capabilities of one of skill in the art, for example, using publicly available computer software such as BLAST, BLAST-2, or Megalign software. Those skilled in the art can determine appropriate parameters for aligning sequences, including any algorithms needed to achieve maximal alignment over the full length of the sequences being compared. For example, percent sequence identity values may be generated using the sequence comparison computer program BLAST. As an illustration, the percent sequence identity of a given nucleic acid or amino acid sequence, A, to, with, or against a given nucleic acid or amino acid sequence, B, (which can alternatively be phrased as a given nucleic acid or amino acid sequence, A that has a certain percent sequence identity to, with, or against a given nucleic acid or amino acid sequence, B) is calculated as follows:

100 multiplied by (the fraction $X/Y$)

where X is the number of nucleotides or amino acids scored as identical matches by a sequence alignment program (e.g., BLAST) in that program's alignment of A and B, and where Y is the total number of nucleic acids in B. It will be appreciated that where the length of nucleic acid or amino acid sequence A is not equal to the length of nucleic acid or amino acid sequence B, the percent sequence identity of A to B will not equal the percent sequence identity of B to A.

A "pharmaceutically acceptable excipient," as used herein, refers to any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration.

As used herein, the term "pharmaceutically acceptable salt" means any pharmaceutically acceptable salt of the compound of any of the compounds described herein. For example, pharmaceutically acceptable salts of any of the compounds described herein include those that are within the scope of sound medical judgment, suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., J. Pharmaceutical Sciences 66:1-19, 1977 and in Pharmaceutical Salts: Properties, Selection, and Use, (Eds. P. H. Stahl and C. G. Wermuth), Wiley-VCH, 2008. The salts can be prepared in situ during the final isolation and purification of the compounds described herein or separately by reacting a free base group with a suitable organic acid. The compounds described herein may have ionizable groups so as to be capable of preparation as pharmaceutically acceptable salts. These salts may be acid addition salts involving inorganic or organic acids or the salts may, in the case of acidic forms of the compounds described herein, be prepared from inorganic or organic bases. Frequently, the compounds are prepared or used as pharmaceutically acceptable salts prepared as addition products of pharmaceutically acceptable acids or bases. Suitable pharmaceutically acceptable acids and bases and methods for preparation of the appropriate salts are well-known in the art. Salts may be prepared from pharmaceutically acceptable non-toxic acids and bases including inorganic and organic acids and bases.

The term "pharmaceutical composition," as used herein, represents a composition containing a compound described herein formulated with a pharmaceutically acceptable excipient, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other pharmaceutically acceptable formulation.

By "reducing the activity of BRD9," is meant decreasing the level of an activity related to an BRD9, or a related downstream effect. A non-limiting example of inhibition of an activity of BRD9 is decreasing the level of a BAF complex (e.g., GBAF) in a cell. The activity level of BRD9 may be measured using any method known in the art. In some embodiments, an agent which reduces the activity of BRD9 is a small molecule BRD9 inhibitor. In some embodiments, an agent which reduces the activity of BRD9 is a small molecule BRD9 degrader.

By "reducing the level of BRD9," is meant decreasing the level of BRD9 in a cell or subject. The level of BRD9 may be measured using any method known in the art.

By a "reference" is meant any useful reference used to compare protein or mRNA levels. The reference can be any sample, standard, standard curve, or level that is used for comparison purposes. The reference can be a normal reference sample or a reference standard or level. A "reference sample" can be, for example, a control, e.g., a predetermined negative control value such as a "normal control" or a prior sample taken from the same subject; a sample from a normal healthy subject, such as a normal cell or normal tissue; a sample (e.g., a cell or tissue) from a subject not having a disease; a sample from a subject that is diagnosed with a disease, but not yet treated with a compound described herein; a sample from a subject that has been treated by a compound described herein; or a sample of a purified protein (e.g., any described herein) at a known normal concentration. By "reference standard or level" is meant a value or number derived from a reference sample. A "normal control value" is a pre-determined value indicative of non-disease state, e.g., a value expected in a healthy control subject. Typically, a normal control value is expressed as a range ("between X and Y"), a high threshold ("no higher than X"), or a low threshold ("no lower than X"). A subject having a measured value within the normal control value for a particular biomarker is typically referred to as "within normal limits" for that biomarker. A normal reference standard or level can be a value or number derived from a normal subject not having a disease or disorder (e.g., cancer); a subject that has been treated with a compound described herein. In preferred embodiments, the reference sample, standard, or level is matched to the sample subject sample by at least one of the following criteria: age, weight, sex, disease stage, and overall health. A standard curve of levels of a purified protein, e.g., any described herein, within the normal reference range can also be used as a reference.

As used herein, the term "subject" refers to any organism to which a composition in accordance with the invention may be administered, e.g., for experimental, diagnostic, prophylactic, and/or therapeutic purposes. Typical subjects include any animal (e.g., mammals such as mice, rats, rabbits, non-human primates, and humans). A subject may seek or be in need of treatment, require treatment, be receiving treatment, be receiving treatment in the future, or be a human or animal who is under care by a trained professional for a particular disease or condition.

As used herein, the term "SS18-SSX fusion protein-related disorder" refers to a disorder that is caused or affected by the level and/or activity of SS18-SSX fusion protein.

As used herein, the terms "treat," "treated," or "treating" mean both therapeutic treatment and prophylactic or preventative measures wherein the object is to prevent or slow down (lessen) an undesired physiological condition, disorder, or disease, or obtain beneficial or desired clinical results. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total), whether detectable or undetectable; an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment.

As used herein, the terms "variant" and "derivative" are used interchangeably and refer to naturally-occurring, synthetic, and semi-synthetic analogues of a compound, peptide, protein, or other substance described herein. A variant or derivative of a compound, peptide, protein, or other substance described herein may retain or improve upon the biological activity of the original material. The details of one or more embodiments of the invention are set forth in the description below. Other features, objects, and advantages of the invention will be apparent from the description and from the claims.

DETAILED DESCRIPTION

Figure 1:
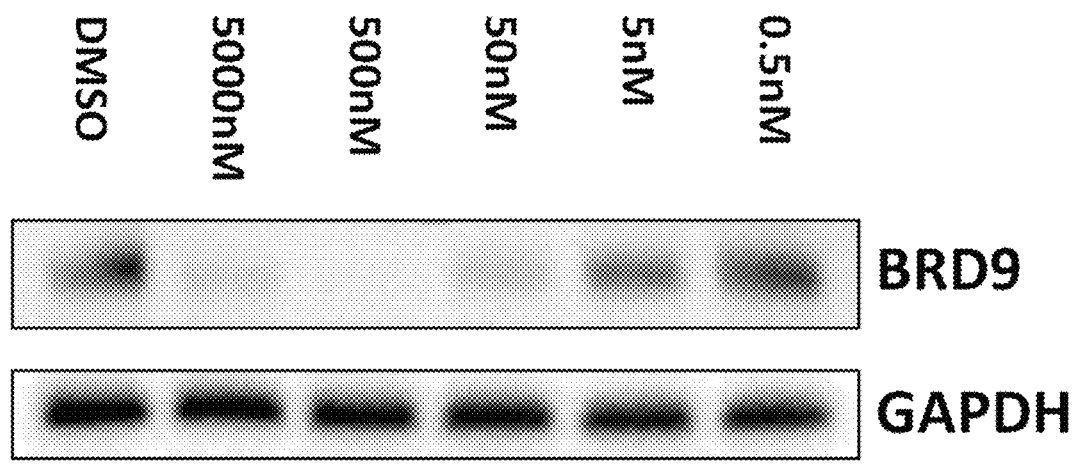
FIG. 1 is an image illustrating dose dependent depletion of BRD9 levels in a synovial sarcoma cell line (SYO1) in the presence of a BRD9 degrader.

The present disclosure features compositions and methods useful for the treatment of BAF-related disorders (e.g., cancer and infection). The disclosure further features compositions and methods useful for inhibition of the level and/or activity of BRD9, e.g., for the treatment of disorders such as cancer (e.g., sarcoma) and infection (e.g., viral infection), e.g., in a subject in need thereof.

Compounds

Compounds described herein reduce the level of an activity related to BRD9, or a related downstream effect, or reduce the level of BRD9 in a cell or subject. Exemplary compounds described herein have the structure of compound D1, S-D1, R-D1, or D2 in Table 1, or a pharmaceutically acceptable salt thereof.

Pharmaceutical Uses

The compounds described herein are useful in the methods of the invention and, while not bound by theory, are believed to exert their desirable effects through their ability to modulate the level, status, and/or activity of a BAF complex, e.g., by inhibiting the activity or level of the BRD9 protein in a cell within the BAF complex in a mammal.

An aspect of the present invention relates to methods of treating disorders related to BRD9 such as cancer in a subject in need thereof. In some embodiments, the compound is administered in an amount and for a time effective to result in one of (or more, e.g., two or more, three or more, four or more of): (a) reduced tumor size, (b) reduced rate of tumor growth, (c) increased tumor cell death (d) reduced tumor progression, (e) reduced number of metastases, (f) reduced rate of metastasis, (g) decreased tumor recurrence (h) increased survival of subject, and (i) increased progression free survival of a subject.

Treating cancer can result in a reduction in size or volume of a tumor. For example, after treatment, tumor size is reduced by 5% or greater (e.g., 10%, 20%, 30%, 40%, 50%, 60%, 70%, 80%, 90%, or greater) relative to its size prior to treatment. Size of a tumor may be measured by any reproducible means of measurement. For example, the size of a tumor may be measured as a diameter of the tumor.

Treating cancer may further result in a decrease in number of tumors. For example, after treatment, tumor number is reduced by 5% or greater (e.g., 10%, 20%, 30%, 40%, 50%, 60%, 70%, 80%, 90%, or greater) relative to number prior to treatment. Number of tumors may be measured by any reproducible means of measurement, e.g., the number of tumors may be measured by counting tumors visible to the naked eye or at a specified magnification (e.g., 2×, 3×, 4×, 5×, 10×, or 50×).

Treating cancer can result in a decrease in number of metastatic nodules in other tissues or organs distant from the primary tumor site. For example, after treatment, the number of metastatic nodules is reduced by 5% or greater (e.g., 10%, 20%, 30%, 40%, 50%, 60%, 70%, 80%, 90% or greater) relative to number prior to treatment. The number of metastatic nodules may be measured by any reproducible means of measurement. For example, the number of metastatic nodules may be measured by counting metastatic nodules visible to the naked eye or at a specified magnification (e.g., 2×, 10×, or 50×).

Treating cancer can result in an increase in average survival time of a population of subjects treated according to the present invention in comparison to a population of untreated subjects. For example, the average survival time is increased by more than 30 days (more than 60 days, 90 days, or 120 days). An increase in average survival time of a population may be measured by any reproducible means. An increase in average survival time of a population may be measured, for example, by calculating fora population the average length of survival following initiation of treatment with the compound described herein. An increase in average survival time of a population may also be measured, for example, by calculating for a population the average length of survival following completion of a first round of treatment with a pharmaceutically acceptable salt of a compound described herein.

Treating cancer can also result in a decrease in the mortality rate of a population of treated subjects in comparison to an untreated population. For example, the mortality rate is decreased by more than 2% (e.g., more than 5%, 10%, or 25%). A decrease in the mortality rate of a population of treated subjects may be measured by any reproducible means, for example, by calculating for a population the average number of disease-related deaths per unit time following initiation of treatment with a pharmaceutically acceptable salt of a compound described herein. A decrease in the mortality rate of a population may also be measured, for example, by calculating for a population the average number of disease-related deaths per unit time following completion of a first round of treatment with a pharmaceutically acceptable salt of a compound described herein.

Combination Therapies

A method of the invention can be used alone or in combination with an additional therapeutic agent, e.g., other agents that treat cancer or symptoms associated therewith, or in combination with other types of therapies to treat cancer. In combination treatments, the dosages of one or more of the therapeutic compounds may be reduced from standard dosages when administered alone. For example, doses may be determined empirically from drug combinations and permutations or may be deduced by isobolographic analysis (e.g., Black et al., *Neurology* 65:S3-S6 (2005)). In this case, dosages of the compounds when combined should provide a therapeutic effect.

In some embodiments, the second therapeutic agent is a chemotherapeutic agent (e.g., a cytotoxic agent or other chemical compound useful in the treatment of cancer). These include alkylating agents, antimetabolites, folic acid analogs, pyrimidine analogs, purine analogs and related inhibitors, vinca alkaloids, epipodopyyllotoxins, antibiotics, L-Asparaginase, topoisomerase inhibitors, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. Also included is 5-fluorouracil (5-FU), leucovorin (LV), irenotecan, oxaliplatin, capecitabine, paclitaxel, and doxetaxel. Non-limiting examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall (see, e.g., *Agnew, Chem. Intl. Ed Engl.* 33:183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin, including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE®, cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; and pharmaceutically acceptable salts, acids or derivatives of any of the above. Two or more chemotherapeutic agents can be used in a cocktail to be administered in combination with the first therapeutic agent described herein. Suitable dosing regimens of combination chemotherapies are known in the art and described in, for example, Saltz et al., *Proc. Am. Soc. Clin. Oncol.* 18:233a (1999), and Douillard et al., *Lancet* 355(9209):1041-1047 (2000).

In some embodiments, the second therapeutic agent is a DNA damaging agent (e.g., a platinum-based antineoplastic agent, topoisomerase inhibitors, PARP inhibitors, alkylating antineoplastic agents, and ionizing radiation).

Examples of platinum-based antineoplastic agent that may be used as a second therapeutic agent in the compositions and methods of the invention are cisplatin, carboplatin, oxaliplatin, dicycloplatin, eptaplatin, lobaplatin, miriplatin, nedaplatin, triplatin tetranitrate, phenanthrilplatin, picoplatin, and satraplatin. In some embodiments, the second therapeutic agent is cisplatin and the treated cancer is a testicular cancer, ovarian cancer, or a bladder cancer (e.g., advanced bladder cancer). In some embodiments, the second therapeutic agent is carboplatin and the treated cancer is an ovarian cancer, lung cancer, head and neck cancer, brain cancer, or neuroblastoma. In some embodiments, the second therapeutic agent is oxaliplatin and the treated cancer is a colorectal cancer. In some embodiments, the second therapeutic agent is dicycloplatin and the treated cancer is a non-small cell ung cancer or prostate cancer. In some embodiments, the second therapeutic agent is eptaplatin and the treated cancer is a gastric cancer. In some embodiments, the second therapeutic agent is lobaplatin and the treated cancer is a breast cancer. In some embodiments, the second therapeutic agent is miriplatin and the treated cancer is a hepatocellular carcinoma. In some embodiments, the second therapeutic agent is nedaplatin and the treated cancer is a nasopharyngeal carcinoma, esophageal cancer, squamous cell carcinoma, or cervical cancer. In some embodiments, the second therapeutic agent is triplatin tetranitrate and the treated cancer is a lung cancer (e.g., small cell lung cancer) or pancreatic cancer. In some embodiments, the second therapeutic agent is picoplatin and the treated cancer is a lung cancer (e.g., small cell lung cancer), prostate cancer, bladder cancer, or colorectal cancer. In some embodiments, the second therapeutic agent is satrapltin and the treated cancer is a prostate cancer, breast cancer, or lung cancer.

Examples of topoisomerase inhibitors that may be used as a second therapeutic agent in the compositions and methods of the invention are etoposide, teniposide, doxorubicin, daunorubicin, mitoxantrone, amsacrine, ellipticine, irinotecan, topotecan, camptothecin, and diflomotecan. In some embodiments, the second therapeutic agent is etoposide and the treated cancer is a lung cancer (e.g., small cell lung cancer) or testicular cancer. In some embodiments, the second therapeutic agent is teniposide and the treated cancer is an acute lymphoblastic leukemia (e.g., childhood acute lymphoblastic leukemia). In some embodiments, the second therapeutic agent is doxorubicin and the treated cancer is an acute lymphoblastic leukemia, acute myeloblastic leukemia, Hodgkin lymphoma, Non-Hodgkin lymphoma, breast cancer, Wilm's tumor, neuroblastoma, soft tissue sarcoma, bone sarcomas, ovarian carcinoma, transitional cell bladder carcinoma, thyroid carcinoma, gastric carcinoma, or bronchogenic carcinoma. In some embodiments, the second therapeutic agent is daunorubicin and the treated cancer is an acute lymphoblastic leukemia or acute myeloid leukemia. In some embodiments, the second therapeutic agent is mitoxantrone and the treated cancer is a prostate cancer or acute nonlymphocytic leukemia. In some embodiments, the second therapeutic agent is amsacrine and the treated cancer is a leukemia (e.g., acute adult leukemia). In some embodiments, the second therapeutic agent is irinotecan and the treated cancer is a colorectal cancer. In some embodiments, the second therapeutic agent is topotecan and the treated cancer is a lung cancer (e.g., small cell lung cancer). In some embodiments, the second therapeutic agent is diflomotecan and the treated cancer is a lung cancer (e.g., small cell lung cancer).

Examples of alkylating antineoplastic agents that may be used as a second therapeutic agent in the compositions and methods of the invention are cyclophosphamide, uramustine, melphalan, chlorambucil, ifosfamide, bendamustine, carmustine, lomustine, chlorozotocin, fotemustine, nimustine, ranimustine, busulfan, improsulfan, piposulfan, chlornaphazine, cholophosphamide, estramustine, mechlorethamine, mechlorethamine oxide hydrochloride, novembichin, phenesterine, prednimustine, trofosfamide, procarbazine, altretamine, dacarbazine, mitozolomide, and temozolomide. In some embodiments, the second therapeutic agent is cyclophosphamide and the treated cancer is a Non-Hodgking lymphoma. In some embodiments, the second therapeutic agent is melphalan and the treated cancer is a multiple myeloma, ovarian cancer, or melanoma. In some embodiments, the second therapeutic agent is chlorambucil and the treated cancer is a chronic lymphatic leukemia, malignant lymphoma (e.g., lymphosarcoma, giant follicular lymphoma, or Hodgkin's lymphoma). In some embodiments, the second therapeutic agent is ifosfamide and the treated cancer is a testicular cancer. In some embodiments, the second therapeutic agent is bendamustine and the treated cancer is a chronic lymphocytic leukemia or non-Hodgkin lymphoma. In some embodiments, the second therapeutic agent is carmustine and the treated cancer is a brain cancer (e.g., glioblastoma, brainstem glioma, medulloblastoma, astrocytoma, ependymoma, or a metastatic brain tumor), multiple myeloma, Hodgkin's disease, or Non-Hodgkin's lymphoma. In some embodiments, the second therapeutic agent is lomustine and the treated cancer is a brain cancer or Hodgkin's lymphoma. In some embodiments, the second therapeutic agent is fotemustine and the treated cancer is a melanoma. In some embodiments, the second therapeutic agent is nimustine and the treated cancer is a brain cancer. In some embodiments, the second therapeutic agent is ranimustine and the treated cancer is a chronic myelogenous leukemia or polycythemia vera. In some embodiments, the second therapeutic agent is busulfan and the treated cancer is a chronic myelogenous leukemia. In some embodiments, the second therapeutic agent is improsulfan and the treated cancer is a sarcoma. In some embodiments, the second therapeutic agent is estramustine and the treated cancer is a prostate cancer (e.g., prostate carcinoma). In some embodiments, the second therapeutic agent is mechlomethamine and the treated cancer is a cutaneous T-cell lymphoma. In some embodiments, the second therapeutic agent is trofosfamide and the treated cancer is a sarcoma (e.g., soft tissue sarcoma). In some embodiments, the second therapeutic agent is procarbazine and the treated cancer is a Hodgkin's disease. In some embodiments, the second therapeutic agent is altretamine and the treated cancer is an ovarian cancer. In some embodiments, the second therapeutic agent is dacarbazine and the treated cancer is a melanoma, Hodgkin's lymphoma, or sarcoma. In some embodiments, the second therapeutic agent is temozolomide and the treated cancer is a brain cancer (e.g., astrocytoma or glioblastoma) or lung cancer (e.g., small cell lung cancer).

Examples of PARP inhibitors that may be used as a second therapeutic agent in the compositions and methods of the invention are niraparib, olaparib, rucaparib, talazoparib, veliparib, pamiparib, CK-102, or E7016. Advantageously, the compounds of the invention and a DNA damaging agent may act synergistically to treat cancer. In some embodiments, the second therapeutic agent is niraparib and the treated cancer is an ovarian cancer (e.g., BRCA mutated ovarian cancer), fallopian tube cancer (e.g., BRCA mutated fallopian tube cancer), or primary peritoneal cancer (e.g., BRCA mutated primary peritoneal cancer). In some embodiments, the second therapeutic agent is olaparib and the treated cancer is a lung cancer (e.g., small cell lung cancer), ovarian cancer (e.g., BRCA mutated ovarian cancer), breast cancer (e.g., BRCA mutated breast cancer), fallopian tube cancer (e.g., BRCA mutated fallopian tube cancer), primary peritoneal cancer (e.g., BRCA mutated primary peritoneal cancer), prostate cancer (e.g., castration-resistant prostate cancer), or pancreatic cancer (e.g., pancreatic adenocarcinoma). In some embodiments, the second therapeutic agent is rucaparib and the treated cancer is an ovarian cancer (e.g., BRCA mutated ovarian cancer), fallopian tube cancer (e.g., BRCA mutated fallopian tube cancer), or primary peritoneal cancer (e.g., BRCA mutated primary peritoneal cancer). In some embodiments, the second therapeutic agent is talazoparib and the treated cancer is a breast cancer (e.g., BRCA mutated breast cancer). In some embodiments, the second therapeutic agent is veliparib and the treated cancer is a lung cancer (e.g., non-small cell lung cancer), malenoma, breast cancer, ovarian cancer, prostate cancer, or brain cancer. In some embodiments, the second therapeutic agent is pamiparib and the treated cancer is an ovarian cancer. In some embodiments, the second therapeutic agent is CK-102 and the treated cancer is a lung cancer (e.g., non-small cell lung cancer). In some embodiments, the second therapeutic agent is E7016 and the treated cancer is a melanoma.

Without wishing to be bound by theory, the synergy between the compounds of the invention and DNA damaging agents may be attributed to the necessity of BRD9 for DNA repair; inhibition of BRD9 may sensitize cancer (e.g., cancer cell or cancer tissue) to DNA damaging agents.

In some embodiments, the second therapeutic agent is a JAK inhibitor (e.g., JAK1 inhibitor). Non-limiting examples of JAK inhibitors that may be used as a second therapeutic agent in the compositions and methods of the invention include tofacitinib, ruxolitinib, oclacitinib, baricitinib, peficitinib, fedratinib, upadacitinib, filgotinib, cerdulatinib, gandotinib, lestaurtinib, momelotinib, pacritinib, abrocitinib, solcitinib, itacitinib, or SHR0302. Without wishing to be bound by theory, the synergy between the compounds of the invention and JAK inhibitors may be inhibitor of SAGA complex to their combined effect of downregulating Foxp3+ Treg cells. In some embodiments, the second therapeutic agent is ruxolitinib and the treated cancer is a myeloproliferative neoplasm (e.g., polycythemia or myelofibrosis), ovarian cancer, breast cancer, pancreatic cancer. In some embodiments, the second therapeutic agent is fedratinib and the treated cancer is a myeloproliferative neoplasm (e.g., myelofibrosis). In some embodiments, the second therapeutic agent is cerdulatinib and the treated cancer is a lymphoma (e.g., peripheral T-cell lymphoma). In some embodiments, the second therapeutic agent is gandotinib and the treated cancer is a myeloproliferative neoplasm (e.g., polycythemia or myelofibrosis). In some embodiments, the second therapeutic agent is lestaurtinib and the treated cancer is a myeloproliferative neoplasm (e.g., polycythemia or myelofibrosis), leukemia (e.g., acute myeloid leukemia), pancreatic cancer, prostate cancer, or neuroblastoma. In some embodiments, the second therapeutic agent is momelotinib and the treated cancer is a myeloproliferative neoplasm (e.g., polycythemia or myelofibrosis) or pancreatic cancer (e.g., pancreatic ductal adenocarcinoma). In some embodiments, the second therapeutic agent is momelotinib and the treated cancer is a myeloproliferative neoplasm (e.g., polycythemia or myelofibrosis). In some embodiments, the second therapeutic agent is momelotinib and the treated cancer is a myeloproliferative neoplasm (e.g., polycythemia or myelofibrosis) or pancreatic cancer (e.g., pancreatic ductal adenocarcinoma).

In some embodiments, the second therapeutic agent is an inhibitor of SAGA complex or a component thereof. A SAGA complex inhibitor may be, e.g., an inhibitory antibody or small molecule inhibitor, of CCDC101, Tada2B, Tada3, Usp22, Tada1, Taf61, Supt5, Supt20, or a combination thereof. Without wishing to be bound by theory, the synergy between the compounds of the invention and inhibitors of SAGA complex may be attributed to their combined effect of downregulating Foxp3+ Treg cells. In some embodiments, the second therapeutic agent is a therapeutic agent which is a biologic such a cytokine (e.g., interferon or an interleukin (e.g., IL-2)) used in cancer treatment. In some embodiments the biologic is an anti-angiogenic agent, such as an anti-VEGF agent, e.g., bevacizumab (AVASTIN®). In some embodiments the biologic is an immunoglobulin-based biologic, e.g., a monoclonal antibody (e.g., a humanized antibody, a fully human antibody, an Fc fusion protein or a functional fragment thereof) that agonizes a target to stimulate an anti-cancer response, or antagonizes an antigen important for cancer. Such agents include RITUXAN® (rituximab); ZENAPAX® (daclizumab); SIMULECT® (basiliximab); SYNAGIS® (palivizumab); REMICADE® (infliximab); HERCEPTIN® (trastuzumab); MYLOTARG® (gemtuzumab ozogamicin); CAMPATH® (alemtuzumab); ZEVALIN® (ibritumomab tiuxetan); HUMIRA® (adalimumab); XOLAIR® (omalizumab); BEXXAR® (tositumomab-I-131); RAPTIVA® (efalizumab); ERBITUX® (cetuximab); AVASTIN® (bevacizumab); TYSABRI® (natalizumab); ACTEMRA® (tocilizumab); VECTIBIX® (panitumumab); LUCENTIS® (ranibizumab); SOLIRIS® (eculizumab); CIMZIA® (certolizumab pegol); SIMPONI® (golimumab); ILARIS® (canakinumab); STELARA® (ustekinumab); ARZERRA® (ofatumumab); PROLIA® (denosumab); NUMAX® (motavizumab); ABTHRAX® (raxibacumab); BENLYSTA® (belimumab); YERVOY® (ipilimumab); ADCETRIS® (brentuximab vedotin); PERJETA® (pertuzumab); KADCYLA® (ado-trastuzumab emtansine); and GAZYVA® (obinutuzumab). Also included are antibody-drug conjugates.

The second agent may be a therapeutic agent which is a non-drug treatment. For example, the second therapeutic agent is radiation therapy, cryotherapy, hyperthermia, and/or surgical excision of tumor tissue.

The second agent may be a checkpoint inhibitor. In one embodiment, the inhibitor of checkpoint is an inhibitory antibody (e.g., a monospecific antibody such as a monoclonal antibody). The antibody may be, e.g., humanized or fully human. In some embodiments, the inhibitor of checkpoint is a fusion protein, e.g., an Fc-receptor fusion protein. In some embodiments, the inhibitor of checkpoint is an agent, such as an antibody, that interacts with a checkpoint protein. In some embodiments, the inhibitor of checkpoint is an agent, such as an antibody, that interacts with the ligand of a checkpoint protein. In some embodiments, the inhibitor of checkpoint is an inhibitor (e.g., an inhibitory antibody or small molecule inhibitor) of CTLA-4 (e.g., an anti-CTLA4 antibody or fusion a protein such as ipilimumab/YERVOY® or tremelimumab). In some embodiments, the inhibitor of checkpoint is an inhibitor (e.g., an inhibitory antibody or small molecule inhibitor) of PD-1 (e.g., nivolumab/OPDIVO®; pembrolizumab/KEYTRUDA®; pidilizumab/CT-011). In some embodiments, the inhibitor of checkpoint is an inhibitor (e.g., an inhibitory antibody or small molecule inhibitor) of PDL1 (e.g., MPDL3280A/RG7446; MED14736; MSB0010718C; BMS 936559). In some embodiments, the inhibitor of checkpoint is an inhibitor (e.g., an inhibitory antibody or Fc fusion or small molecule inhibitor) of PDL2 (e.g., a PDL2/Ig fusion protein such as AMP 224). In some embodiments, the inhibitor of checkpoint is an inhibitor (e.g., an inhibitory antibody or small molecule inhibitor) of B7-H3 (e.g., MGA271), B7-H4, BTLA, HVEM, TIM3, GAL9, LAG3, VISTA, KIR, 2B4, CD160, CGEN-15049, CHK 1, CHK2, A2aR, B-7 family ligands, or a combination thereof. In some embodiments, the second therapeutic agent is ipilimumab and the treated cancer is a melanoma, kidney cancer, lung cancer (e.g., non-small cell lung cancer or small cell lung cancer), or prostate cancer. In some embodiments, the second therapeutic agent is tremelimumab and the treated cancer is a melanoma, mesothelioma, or lung cancer (e.g., non-small cell lung cancer). In some embodiments, the second therapeutic agent is nivolumab and the treated cancer is a melanoma, lung cancer (e.g., non-small cell lung cancer or small cell lung cancer), kidney cancer, Hodgkin lymphoma, head and neck cancer (e.g., squamous cell carcinoma of the head and neck), urothelial carcinoma, hepatocellular carcinoma, or colorectal cancer. In some embodiments, the second therapeutic agent is pembrolizumab and the treated cancer is a melanoma, lung cancer (e.g., non-small cell lung cancer or small cell lung cancer), Hodgkin lymphoma, head and neck cancer (e.g., squamous cell carcinoma of the head and neck), primary mediastinal large B-cell lymphoma, urothelial carcinoma, hepatocellular carcinoma, microsatellite instability-high cancer, gastric cancer, esophageal cancer, cervical cancer, Merkel cell carcinoma, kidney carcinoma, or endometrial carcinoma. In some embodiments, the second therapeutic agent is MPDL3280A and the treated cancer is a lung cancer (e.g., non-small cell lung cancer or small cell lung cancer), urothelial carcinoma, hepatocellular carcinoma, or breast cancer. In some embodiments, the second therapeutic agent is MED14736 and the treated cancer is a lung cancer (e.g., non-small cell lung cancer or small cell lung cancer) or urothelial carcinoma. In some embodiments, the second therapeutic agent is MSB0010718C and the treated cancer is a urothelial carcinoma. In some embodiments, the second therapeutic agent is MSB0010718C and the treated cancer is a melanoma, lung cancer (e.g., non-small cell lung cancer), colorectal cancer, kidney cancer, ovarian cancer, pancreatic cancer, gastric cancer, and breast cancer.

Advantageously, the compounds of the invention and a checkpoint inhibitor may act synergistically to treat cancer. Without wishing to be bound by theory, the synergy between the compounds of the invention and checkpoint inhibitors may be attributed to the checkpoint inhibitor efficacy enhancement associated with the BRD9 inhibition-induced downregulation of Foxp3+ Treg cells.

In some embodiments, the anti-cancer therapy is a T cell adoptive transfer (ACT) therapy. In some embodiments, the T cell is an activated T cell. The T cell may be modified to express a chimeric antigen receptor (CAR). CAR modified T (CAR-T) cells can be generated by any method known in the art. For example, the CAR-T cells can be generated by introducing a suitable expression vector encoding the CAR to a T cell. Prior to expansion and genetic modification of the T cells, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In some embodiments, the T cell is an autologous T cell. Whether prior to or after genetic modification of the T cells to express a desirable protein (e.g., a CAR), the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

In any of the combination embodiments described herein, the first and second therapeutic agents are administered simultaneously or sequentially, in either order. The first therapeutic agent may be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours up to 24 hours or up to 1-7, 1-14, 1-21 or 1-30 days before or after the second therapeutic agent.

Pharmaceutical Compositions

The pharmaceutical compositions described herein are preferably formulated into pharmaceutical compositions for administration to human subjects in a biologically compatible form suitable for administration in vivo.

The compounds described herein may be used in the form of the free base, in the form of salts, solvates, and as prodrugs. All forms are within the methods described herein. In accordance with the methods of the invention, the described compounds or salts, solvates, or prodrugs thereof may be administered to a patient in a variety of forms depending on the selected route of administration, as will be understood by those skilled in the art. The compounds described herein may be administered, for example, by oral, parenteral, buccal, sublingual, nasal, rectal, patch, pump, intratumoral, or transdermal administration and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

A compound described herein may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, a compound described herein may be incorporated with an excipient and used in the form of ingestible tablets, buccal tablets, troches, capsules, elixirs, suspensions, syrups, and wafers. A compound described herein may also be administered parenterally. Solutions of a compound described herein can be prepared in water suitably mixed with a surfactant, such as hydroxypropylcellulose. Dispersions can also be prepared in glycerol, liquid polyethylene glycols, DMSO, and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington's Pharmaceutical Sciences (2012, 22nd ed.) and in The United States Pharmacopeia: The National Formulary (USP 41 NF36), published in 2018. The pharmaceutical forms suitable for injectable use include sterile aqueous solutions or dispersions and sterile powders for the extemporaneous preparation of sterile injectable solutions or dispersions. In all cases the form must be sterile and must be fluid to the extent that may be easily administered via syringe. Compositions for nasal administration may conveniently be formulated as aerosols, drops, gels, and powders. Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, such as a single dose nasal inhaler or an aerosol dispenser fitted with a metering valve which is intended for disposal after use. Where the dosage form includes an aerosol dispenser, it will contain a propellant, which can be a compressed gas, such as compressed air or an organic propellant, such as fluorochlorohydrocarbon. The aerosol dosage forms can also take the form of a pump-atomizer. Compositions suitable for buccal or sublingual administration include tablets, lozenges, and pastilles, where the active ingredient is formulated with a carrier, such as sugar, acacia, tragacanth, gelatin, and glycerine. Compositions for rectal administration are conveniently in the form of suppositories containing a conventional suppository base, such as cocoa butter. A compound described herein may be administered intratumorally, for example, as an intratumoral injection. Intratumoral injection is injection directly into the tumor vasculature and is specifically contemplated for discrete, solid, accessible tumors. Local, regional, or systemic administration also may be appropriate. A compound described herein may advantageously be contacted by administering an injection or multiple injections to the tumor, spaced for example, at approximately, 1 cm intervals. In the case of surgical intervention, the present invention may be used preoperatively, such as to render an inoperable tumor subject to resection. Continuous administration also may be applied where appropriate, for example, by implanting a catheter into a tumor or into tumor vasculature.

The compounds described herein may be administered to an animal, e.g., a human, alone or in combination with pharmaceutically acceptable carriers, as noted herein, the proportion of which is determined by the solubility and chemical nature of the compound, chosen route of administration, and standard pharmaceutical practice.

Dosages

The dosage of the compounds described herein, and/or compositions including a compound described herein, can vary depending on many factors, such as the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. One of skill in the art can determine the appropriate dosage based on the above factors. The compounds described herein may be administered initially in a suitable dosage that may be adjusted as required, depending on the clinical response. In general, satisfactory results may be obtained when the compounds described herein are administered to a human at a daily dosage of, for example, between 0.05 mg and 3000 mg (measured as the solid form). Dose ranges include, for example, between 10-1000 mg (e.g., 50-800 mg). In some embodiments, 50, 100, 150, 200, 250, 300, 350, 400, 450, 500, 550, 600, 650, 700, 750, 800, 850, 900, 950, or 1000 mg of the compound is administered.

Alternatively, the dosage amount can be calculated using the body weight of the patient. For example, the dose of a compound, or pharmaceutical composition thereof, administered to a patient may range from 0.1-100 mg/kg.

Kits

The invention also features kits including (a) a pharmaceutical composition including an agent that reduces the level and/or activity of BRD9 in a cell or subject described herein, and (b) a package insert with instructions to perform any of the methods described herein. In some embodiments, the kit includes (a) a pharmaceutical composition including an agent that reduces the level and/or activity of BRD9 in a cell or subject described herein, (b) an additional therapeutic agent (e.g., an anti-cancer agent), and (c) a package insert with instructions to perform any of the methods described herein.

EXAMPLES

Example 1—BRD9 Degrader Depletes BRD9 Protein

The following example demonstrates the depletion of the BRD9 protein in synovial sarcoma cells treated with a BRD9 degrader.

Procedure: Cells were treated with DMSO or the BRD9 degrader, Compound 1 (also known as dBRD9, see Remillard et al, *Angew. Chem. Int. Ed. Engl.* 56(21):5738-5743 (2017); see structure of compound 1 below), for indicated doses and timepoints.

(Compound 1)

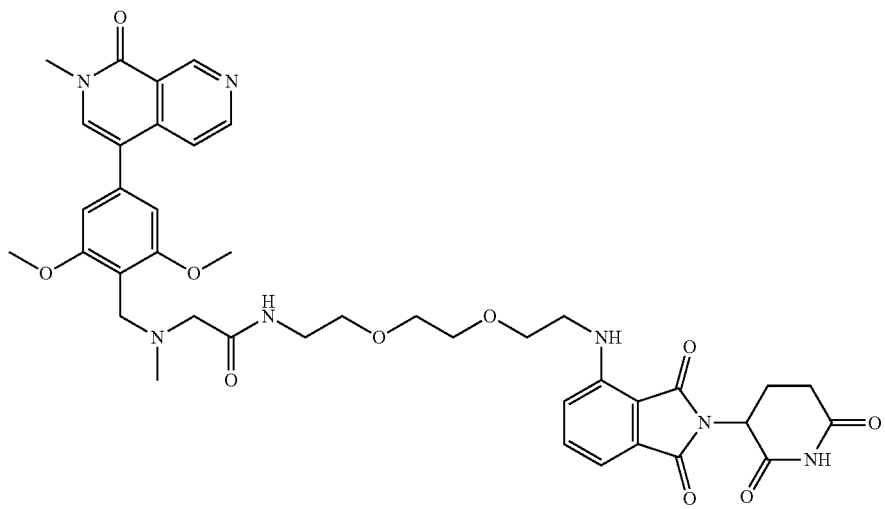

dBRD9

Figure 2:
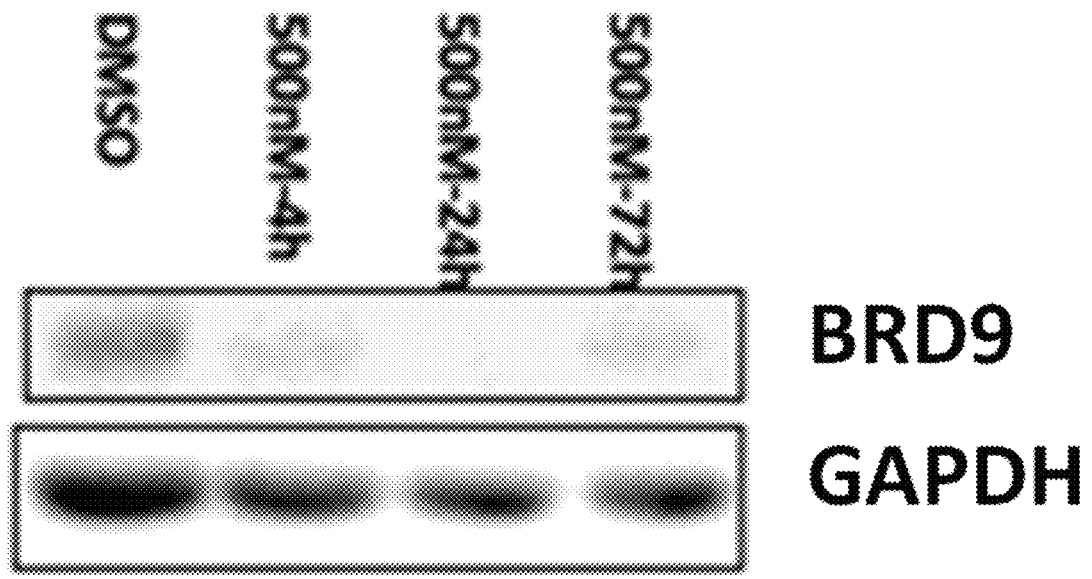
FIG. 2 is an image illustrating sustained suppression of BRD9 levels in a synovial sarcoma cell line (SYO1) in presence of a BRD9 degrader over 72 hours.
Figure 3:
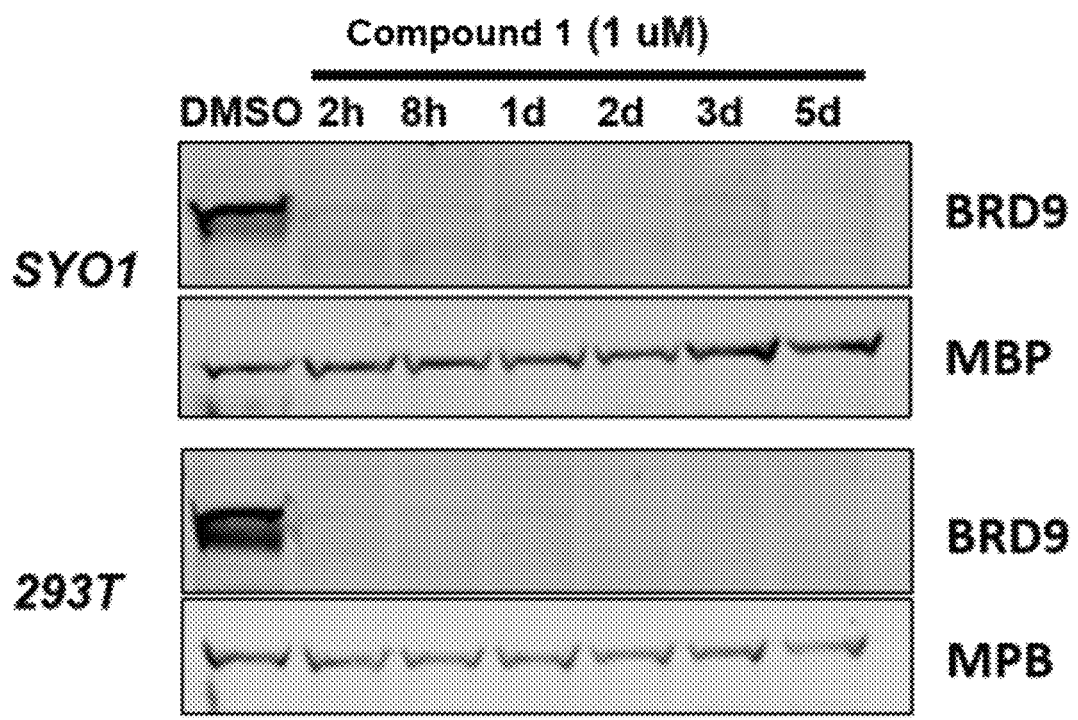
FIG. 3 is an image illustrating sustained suppression of BRD9 levels in two cell lines (293T and SYO1) in the presence of a BRD9 degrader over 5 days.
Figure 4:
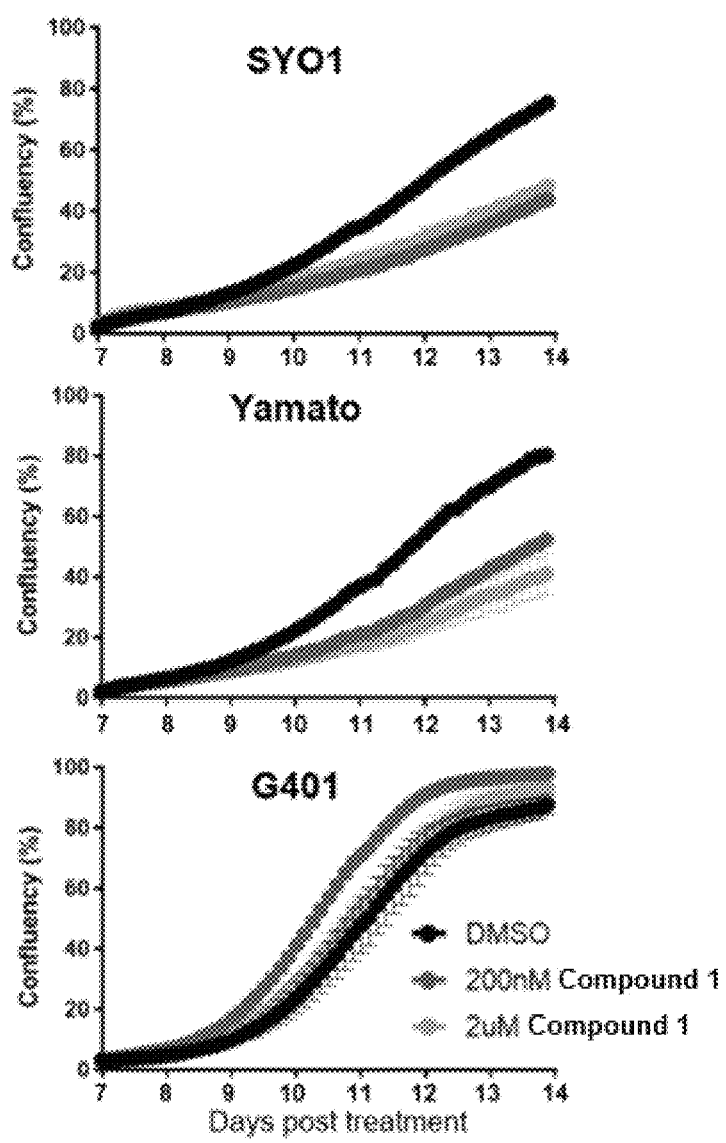
FIG. 4 is an image illustrating sustained suppression of BRD9 levels in synovial sarcoma cell lines (SYO1 and Yamato) in the presence of a BRD9 degrader over 7 days compared to the levels in cells treated with CRISPR reagents.

Whole cell extracts were fractionated by SDS-PAGE and transferred to a polyvinylidene difluoride membrane using a transfer apparatus according to the manufacturer's protocols (Bio-Rad). After incubation with 5% nonfat milk in TBST (10 mM Tris, pH 8.0, 150 mM NaCl, 0.5% Tween 20) for 60 min, the membrane was incubated with antibodies against BRD9 (1:1,000, Bethyl laboratory A303-781A), GAPDH (1:5,000, Cell Signaling Technology), and/or MBP (1:1,000, BioRad) overnight at 4° C. Membranes were washed three times for 10 min and incubated with anti-mouse or anti-rabbit antibodies conjugated with either horseradish peroxidase (HRP, FIGS. 2-3) or IRDye (FIG. 4, 1:20,000, LI-COR) for at least 1 h. Blots were washed with TBST three times and developed with either the ECL system according to the manufacturer's protocols (FIGS. 2-3) or scanned on an Odyssey CLx Imaging system (FIG. 4).

Results: Treatment of SYO1 synovial sarcoma cells with the BRD9 degrader Compound 1 results in dose dependent (FIG. 1) and time dependent (FIG. 2) depletion of BRD9 in the cells. Further, as shown in FIG. 3, the depletion of BRD9 by Compound 1 is replicated in a non-synovial sarcoma cell line (293T) and may be sustained for at least 5 days.

Example 2—Inhibition of Growth of Synovial Cell Lines by BRD9 Inhibitors and BRD9 Degraders The following example demonstrates that BRD9 degraders and inhibitors selectively inhibit growth of synovial sarcoma cells.

Procedures:

Cells were treated with DMSO or the BRD9 degrader, Compound 1, at indicated concentrations, and proliferation was monitored from day 7 to day 14 by measuring confluency over time using an IncuCyte live cell analysis system (FIG. 4). Growth medium and compounds were refreshed every 3-4 days.

Cells were seeded into 12-well plates and treated with DMSO, 1 µM BRD9 inhibitor, Compound 2 (also known as BI-7273, see Martin et al, *J Med Chem.* 59(10):4462-4475 (2016); see structure of compound 2 below), or 1 µM BRD9 degrader, Compound 1.

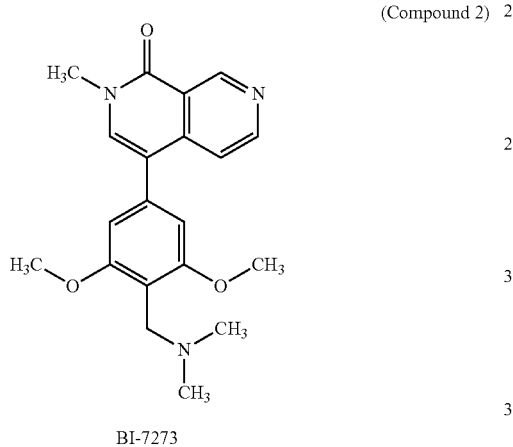

(Compound 2)

BI-7273

Figure 5:
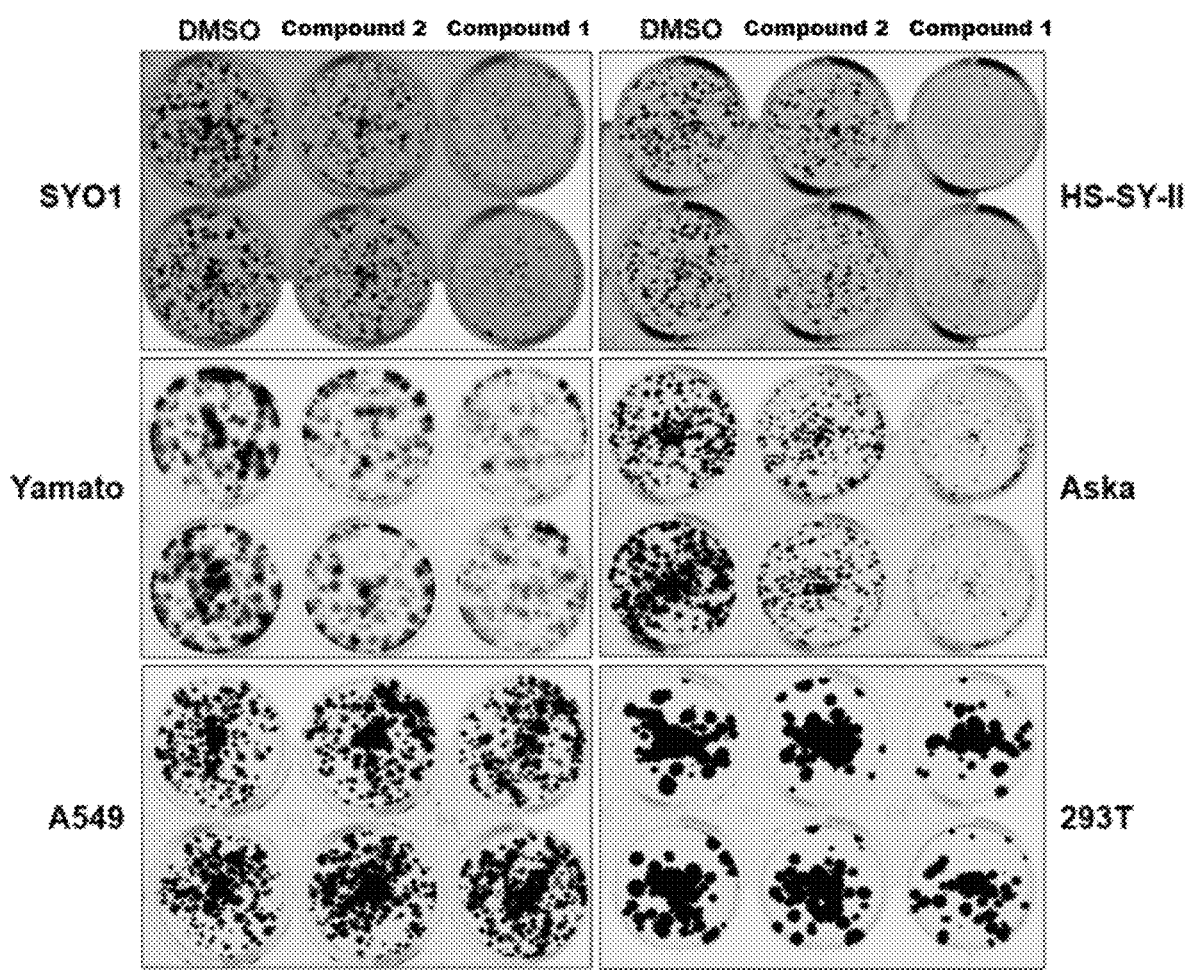
FIG. 5 is an image illustrating the effect on cell growth of six cell lines (SYO1, Yamato, A549, HS-SY-II, ASKA, and 293T) in the presence of a BRD9 degrader and a BRD9 inhibitor.

The number of cells was optimized for each cell line. Growth medium and compounds were refreshed every 3-5 days. SYO1, Yamato, A549, 293T and HS-SY-II cells were fixed and stained at day 11. ASKA cells were fixed and stained at day 23. Staining was done by incubation with crystal violet solution (0.5 g Crystal Violet, 27 ml 37% Formaldehyde, 100 mL 10×PBS, 10 mL Methanol, 863 dH20 to 1 L) for 30 min followed by 3× washes with water and drying the plates for at least 24 h at room temperature. Subsequently plates were scanned on an Odyssey CLx Imaging system (FIG. 5).

Cells were seeded into 96-well ultra-low cluster plate (Costar, #7007) in 200 µL complete media and treated at day 2 with DMSO, Staurosporin, or BRD9 degrader, Compound 1, at indicated doses (FIG. 2C). Media and compounds were changed every 5 d and cell colonies were imaged at day 14.

Figure 6:
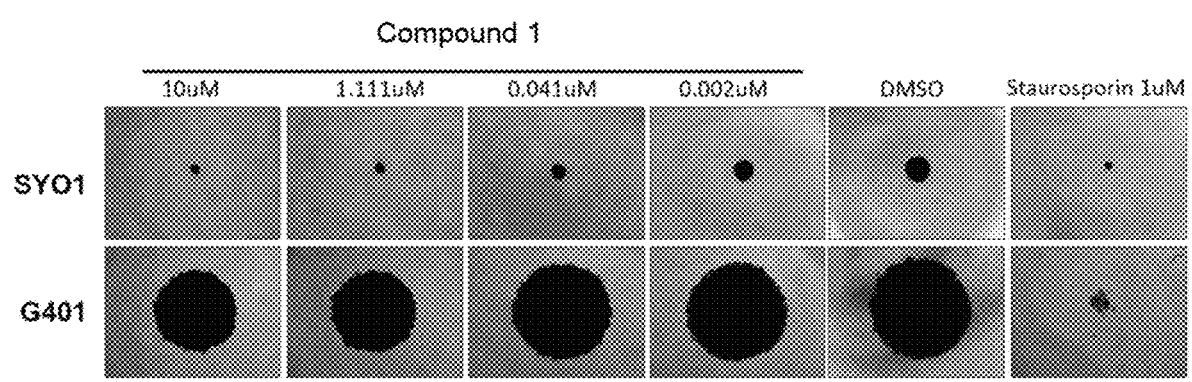
FIG. 6 is an image illustrating the effect on cell growth of two cell lines (SYO1 and G401) in the presence of a BRD9 degrader.

Results: As shown in FIGS. 4, 5, and 6, treatment of synovial sarcoma cell lines (SYO1, Yamato, HS-SY-II, and ASKA) with a BRD9 inhibitor, Compound 2, or a BRD9 degrader, Compound 1, results in inhibition of the growth of the cells, but does not result in inhibition of the growth of non-synovial control cancer cell lines (293T, A549, G401).

Example 3—Selective Inhibition of Growth of Synovial Cell Lines by BRD9 Degraders and BRD9 Binders The following example demonstrates that BRD9 degraders and binders selectively inhibit growth of synovial sarcoma cells.

Procedure: Cells were seeded into 6-well or 12-well plates and were treated daily with a BRD9 degrader (Compound 1), a bromo-domain BRD9 binder (Compound 2), E3 ligase binder (lenalidomide), DMSO, or staurosporin (positive control for cell killing), at indicated concentrations. The number of cells was optimized for each cell line. Growth media was refreshed every 5 days. By day 14, medium was removed, cells were washed with PBS, and stained using 500 µL of 0.005% (w/v) crystal violet solution in 25% (v/v) methanol for at least 1 hour at room temperature. Subsequently plates were scanned on an Odyssey CLx Imaging system.

Figure 7:
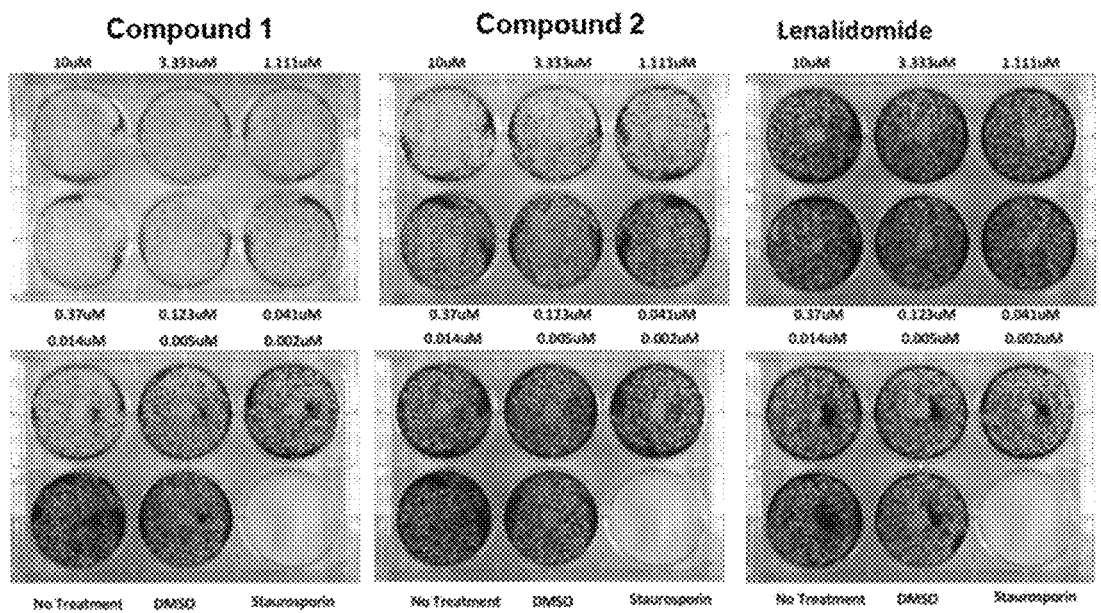
FIG. 7 is an image illustrating the effect on cell growth of three synovial sarcoma cell lines (SYO1, HS-SY-II, and ASKA) in the presence of a BRD9 degrader, BRD9 binder and E3 ligase binder.
Figure 7:
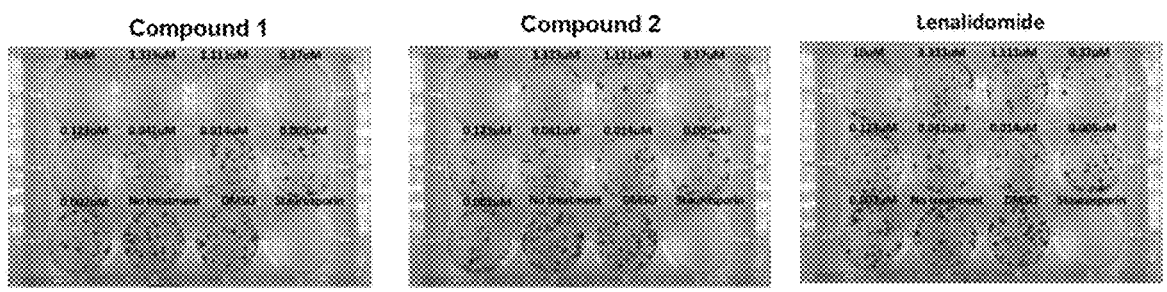
Figure 7:
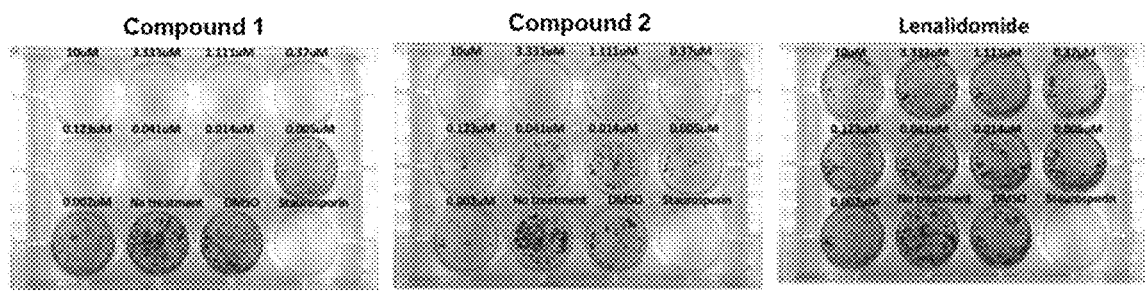
Figure 8:
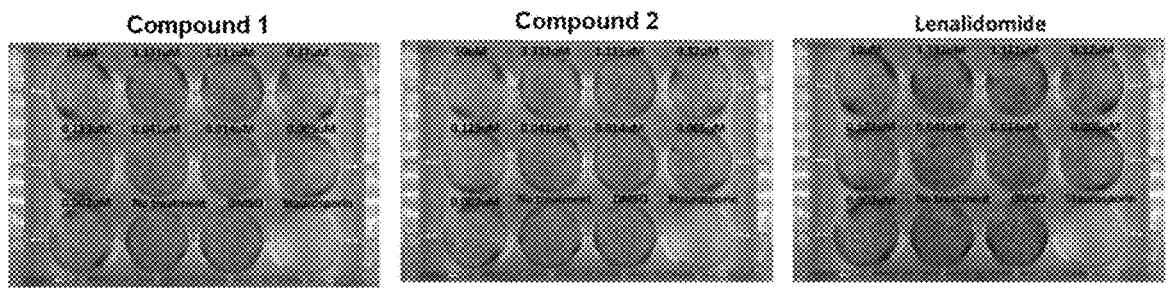
FIG. 8 is an image illustrating the effect on cell growth of three non-synovial sarcoma cell lines (RD, HCT116, and Calu6) in the presence of a BRD9 degrader, BRD9 binder and E3 ligase binder.
Figure 8:
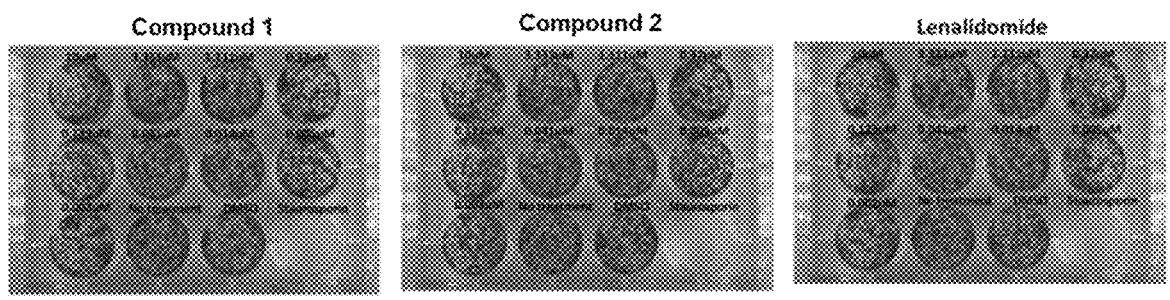
Figure 8:
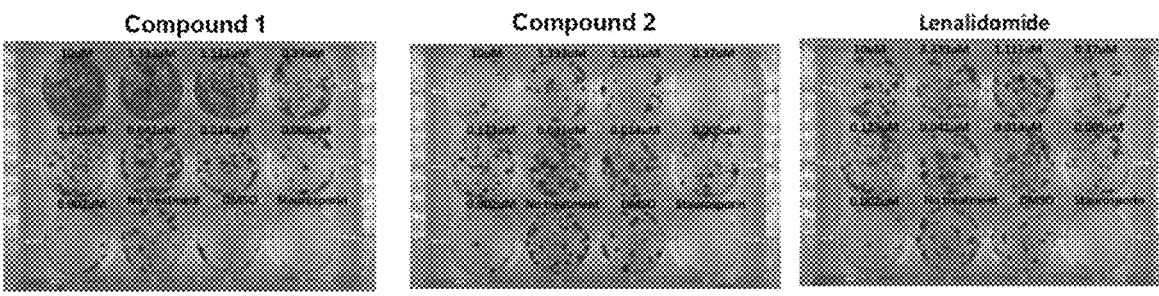
Figure 9:
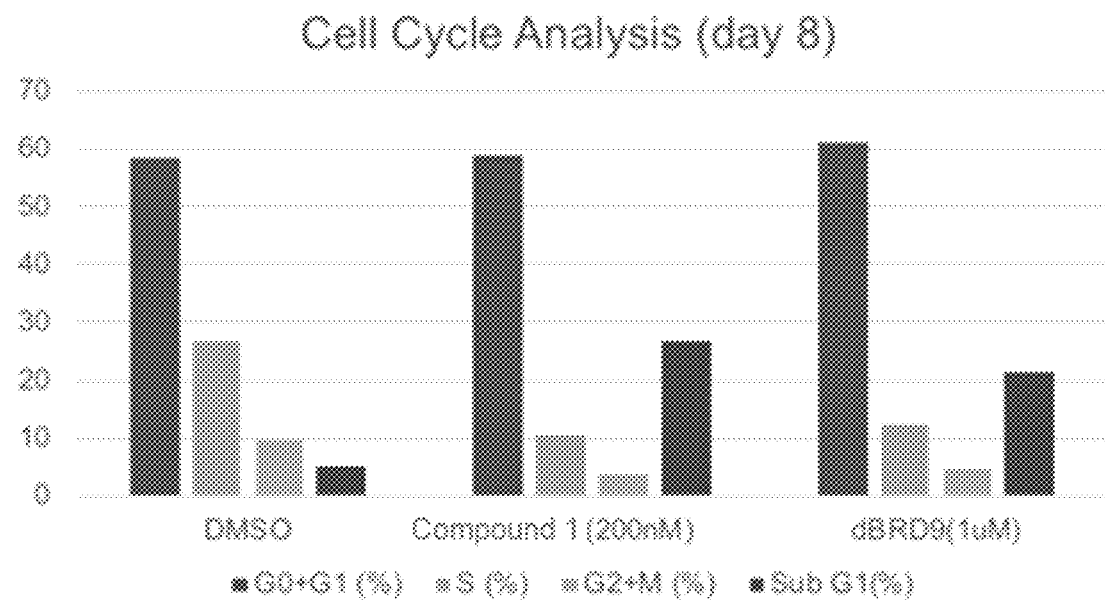
FIG. 9 is a graph illustrating the percentage of SYO1 in various cell cycle phases following treatment with DMSO, Compound 1 at 200 nM, or Compound 1 at 1 µM for 8 or 13 days.
Figure 9:
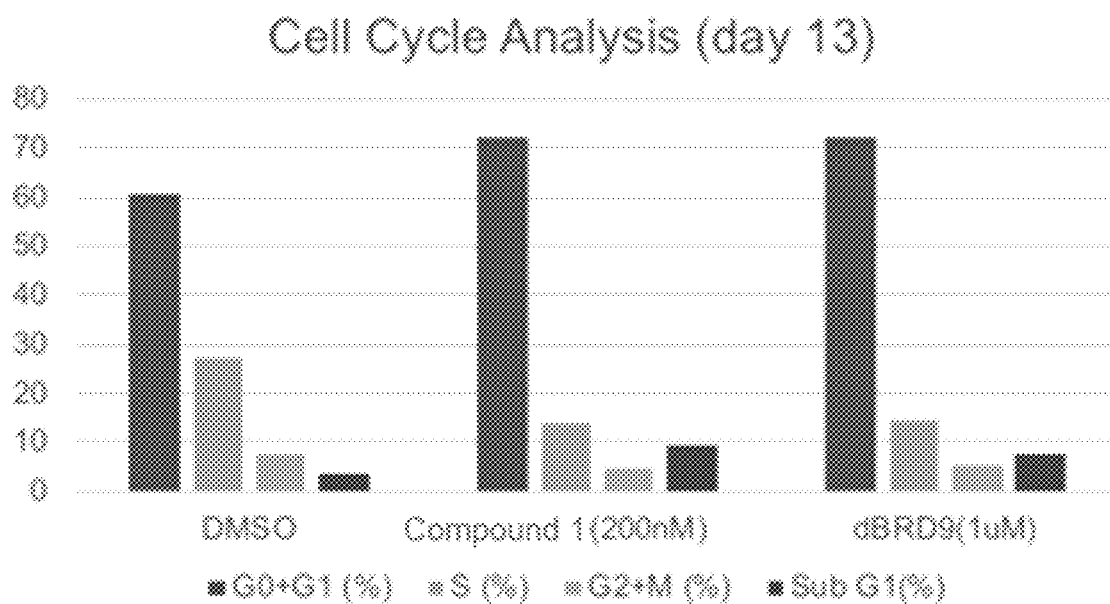
Figure 10:
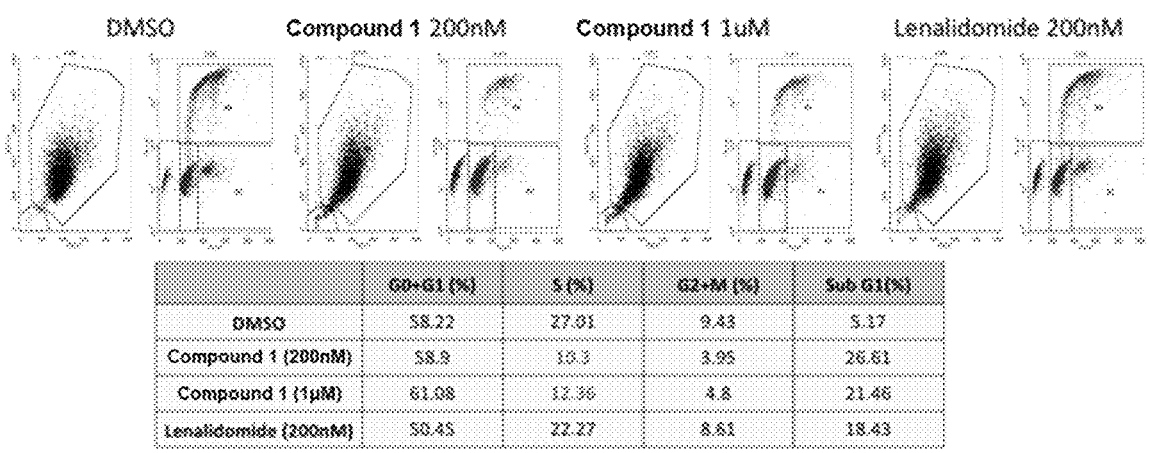
FIG. 10 is a series of contour plots illustrating the percentage of SYO1 cells in various cell cycle phases following treatment with DMSO, Compound 1 at 200 nM, Compound 1 at 1 µM, or lenalidomide at 200 nM for 8 days. Numerical values corresponding to each contour plot are found in the table below.
Figure 11:
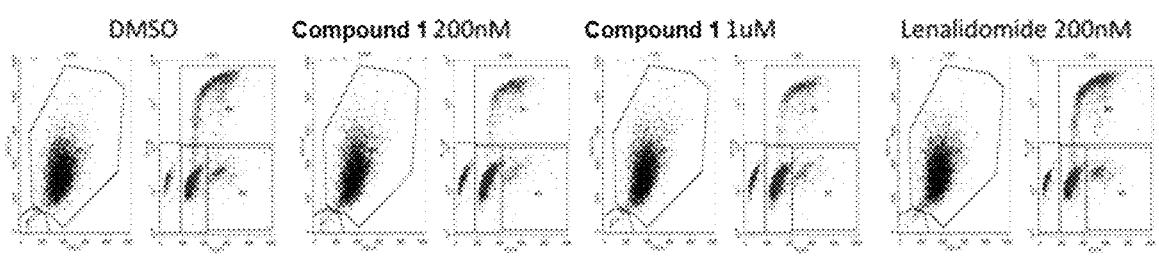
FIG. 11 is a series of contour plots illustrating the percentage of SYO1 cells in various cell cycle phases following treatment with DMSO, Compound 1 at 200 nM, Compound 1 at 1 µM, or lenalidomide at 200 nM for 13 days. Numerical values corresponding to each contour plot are found in the table below.
Figure 12:
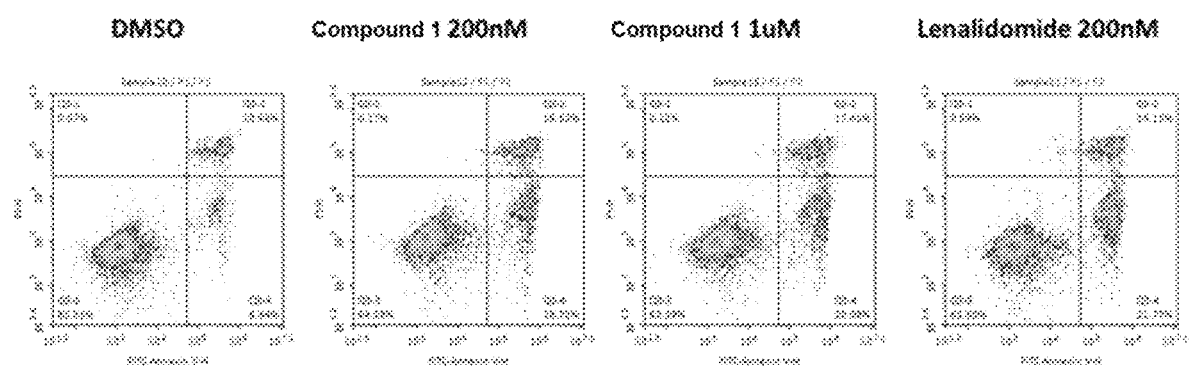
FIG. 12 is a series of contour plots illustrating the percentage of early- and late-apoptotic SYO1 cells following treatment with DMSO, Compound 1 at 200 nM, Compound 1 at 1 µM, or lenalidomide at 200 nM for 8 days. Numerical values corresponding to each contour plot are found in the table below.

Results: As shown in FIGS. 7 and 8, treatment of synovial sarcoma cell lines (SYO1, HS-SY-II, and ASKA) with Compound 1 or Compound 2 resulted in inhibition of the growth of the cells but did not result in inhibition of the growth of non-synovial control cancer cell lines (RD, HCT116, and Calu6). Overall, Compound 1 showed most significant growth inhibition in all synovial cell lines.

Example 4—Inhibition of Cell Growth in Synovial Sarcoma Cells

The following example shows that BRD9 degraders inhibit cell growth and induce apoptosis in synovial sarcoma cells.

Procedure: SYO1 cells were treated for 8 or 13 days with DMSO, a BRD9 degrader (Compound 1) at 200 nM or 1 µM, or an E3 ligase binder (lenalidomide) at 200 nM. Compounds were refreshed every 5 days. Cell cycle analysis was performed using the Click-iT™ Plus EdU Flow Cytometry Assay (Invitrogen). The apoptosis assay was performed using the Annexin V-FITC Apoptosis Detection Kit (Sigma A9210). Assays were performed according to the manufacturer's protocol.

Results: As shown in FIGS. 9-12, treatment with Compound 1 for 8 or 13 days resulted in reduced numbers of cells in the S-phase of the cell cycle as compared to DMSO and lenalidomide.

Treatment with Compound 1 for 8 days also resulted in increased numbers of early- and late-apoptotic cells as compared to DMSO controls.

Example 5—Composition for SS18-SSX1-BAF

The following example shows the identification of BRD9 as a component of SS18-SSX containing BAF complexes.

Procedure: A stable 293T cell line expressing HA-SS18SSX1 was generated using lentiviral integration. SS18-SSX1 containing BAF complexes were subject to affinity purification and subsequent mass spectrometry analysis revealed SS18-SSX1 interacting proteins.

Figure 13:
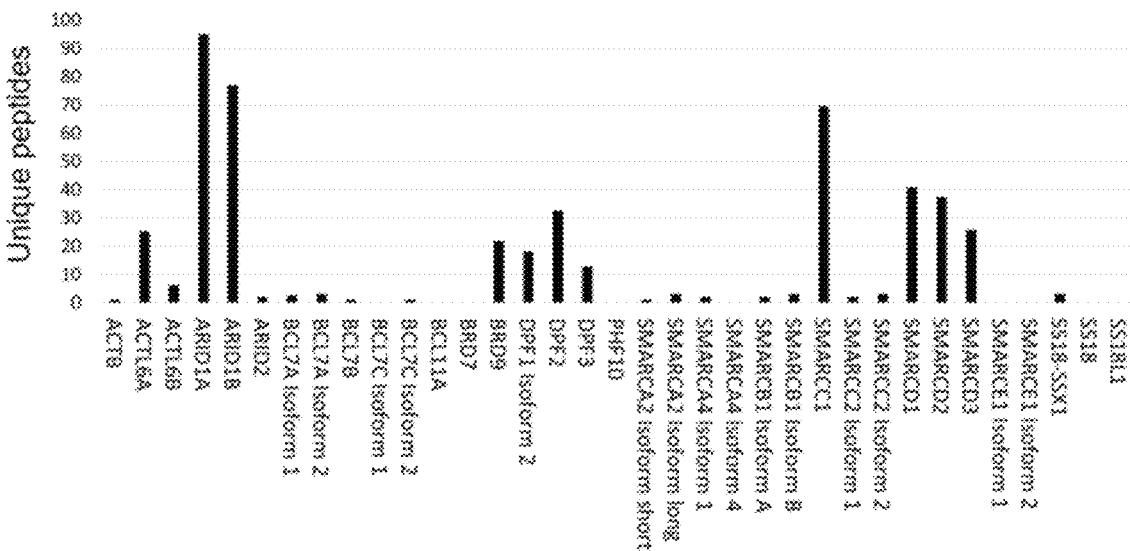
FIG. 13 is a graph illustrating the proteins present in BAF complexes including the SS18-SSX fusion protein.

Results: As shown in FIG. 13, BAF complexes including the SS18-SSX fusion protein also included BRD9. More than 5 unique peptides were identified for ARID1A (95 peptides), ARID1B (77 peptides), SMARCC1 (69 peptides), SMARCD1 (41 peptides), SMARCD2 (37 peptides), DPF2 (32 peptides), SMARCD3 (26 peptides), ACTL6A (25 peptides), BRD9 (22 peptides), DPF1 Isoform 2 (18 peptides), DPF3 (13 peptides), and ACTL6B (6 peptides).

Example 6—Preparation of 4-[6-(azetidin-1-yl)-2-methyl-1-oxo-2,7-naphthyridin-4-yl]-2,6-dimethoxy-benzaldehyde (Intermediate H)

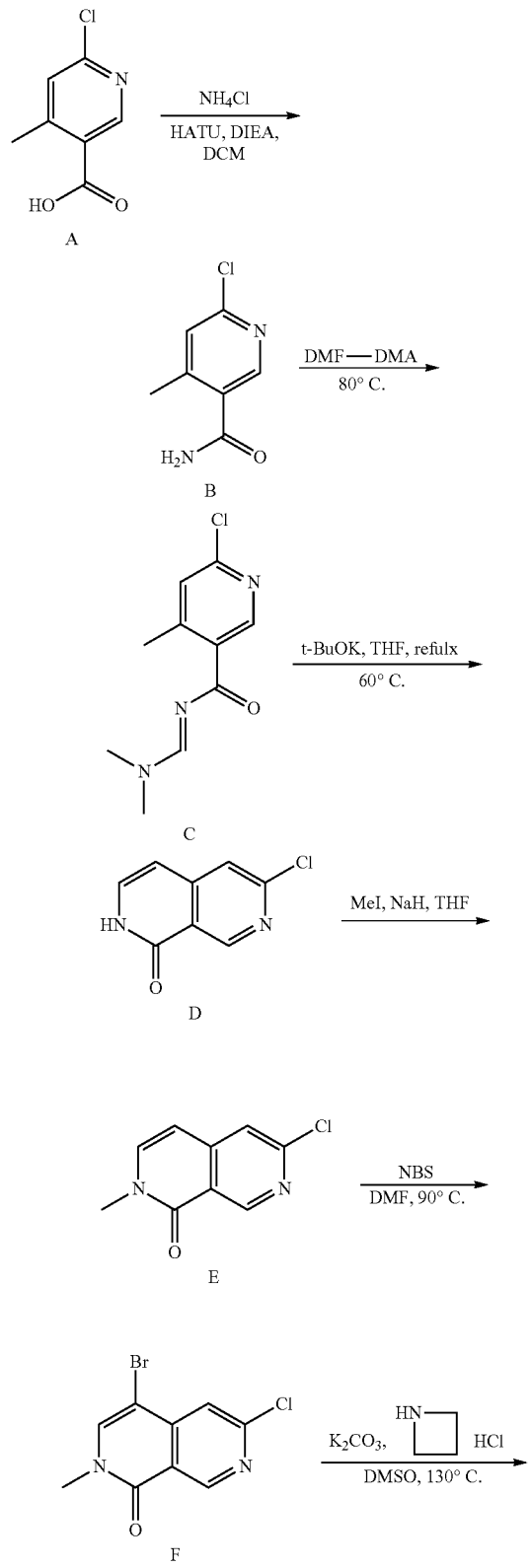

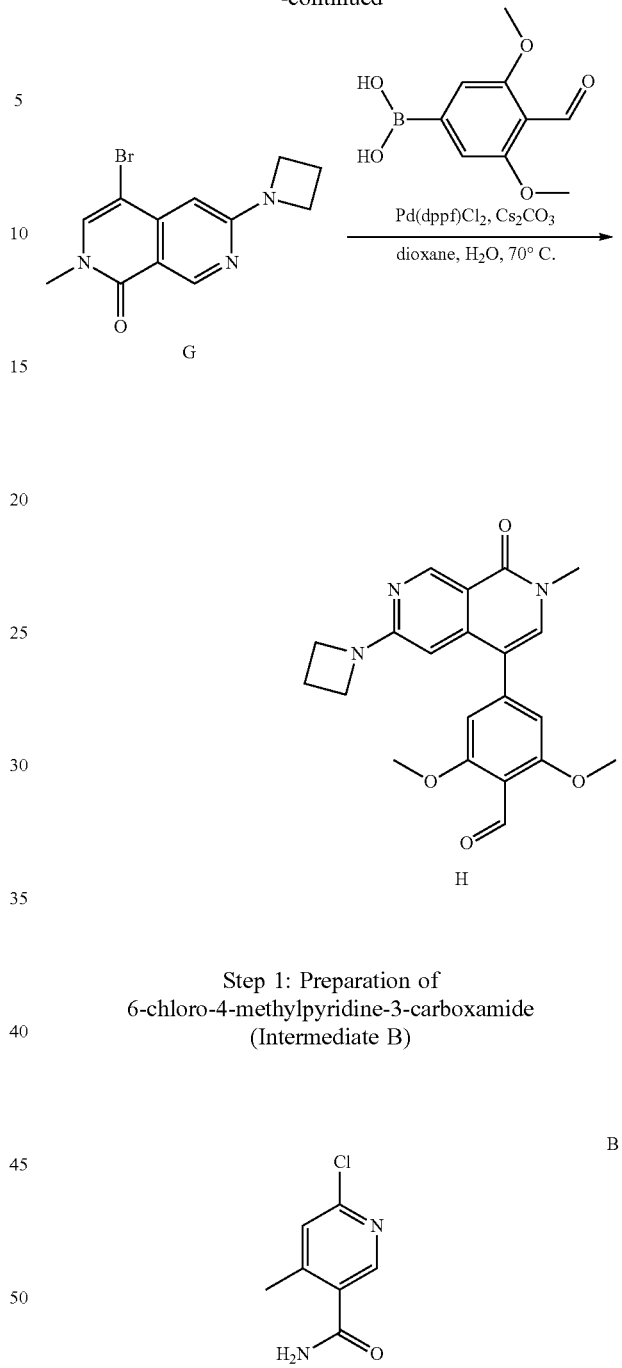

Step 1: Preparation of 6-chloro-4-methylpyridine-3-carboxamide (Intermediate B)

To a stirred mixture of 6-chloro-4-methylpyridine-3-carboxylic acid (20.00 g, 116.564 mmol, 1.00 equiv) and $NH_4Cl$ (62.35 g, 1.17 mol, 10.00 equiv) in dichloromethane (DCM; 400 mL) was added DIEA (22.60 g, 174.846 mmol, 3.00 equiv). After stirring for 5 minutes, HATU (66.48 g, 174.846 mmol, 1.50 equiv) was added in portions. The resulting mixture was stirred for 3 hours at room temperature. The resulting mixture was concentrated under reduced pressure, and the residue was purified by silica gel column chromatography, eluted with petroleum ether/ethyl acetate (PE/EtOAc) from 1/1 to 3/2 to afford 6-chloro-4-methylpyridine-3-carboxamide (18.30 g, 61.3%) as a yellow solid. LCMS (ESI) m/z: $[M+H]^+=171$.

Step 2: Preparation of 6-chloro-N-[(1E)-(dimethyl-amino)methylidene]-4-methylpyridine-3-carboxamide (Intermediate C)

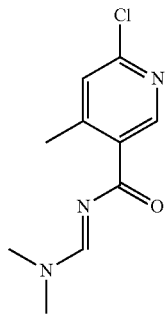

C

To a stirred mixture of 6-chloro-4-methylpyridine-3-carboxamide (18.30 g, 107.268 mmol, 1.00 equiv) and in 2-methyltetrahydrofuran (100 mL) was added DMF-DMA (19.17 g, 160.903 mmol, 1.50 equiv) at 80° C. under nitrogen atmosphere, and stirred for additional 1 hour. Then the mixture was cooled and concentrated to afford 6-chloro-N-[(1E)-(dimethylamino)methylidene]-4-methylpyridine-3-carboxamide (26.3 g, 91.3%) as a yellow crude solid, which was used directly without further purification. LCMS (ESI) m/z: [M+H]$^+$=226.

Step 3: Preparation of 6-chloro-2H-2,7-naphthyridin-1-one (Intermediate D)

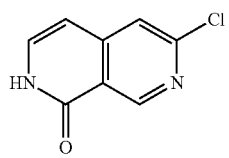

D

To a stirred mixture of 6-chloro-N-[(1E)-(dimethylamino)methylidene]-4-methylpyridine-3-carboxamide (26.30 g) in THF (170.00 mL) was added t-BuOK (174.00 mL, 1 mol/L in THF). The resulting solution was stirred at 60° C. under nitrogen atmosphere for 30 minutes. Then the mixture was cooled and concentrated under reduced pressure. The crude solid was washed with saturated NaHCO$_3$ solution (100 mL) and collected to give 6-chloro-2H-2,7-naphthyridin-1-one (14.1 g, 67.0%) as a pink solid, which was used directly without further purification. LCMS (ESI) m/z: [M+H]$^+$=181.

Step 4: Preparation of 6-chloro-2-methyl-2,7-naphthyridin-1-one (Intermediate E)

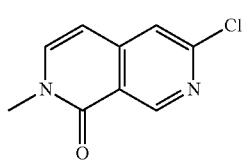

E

To a stirred mixture of 6-chloro-2H-2, 7-naphthyridin-1-one (14.10 g, 78.077 mmol, 1.00 equiv) in anhydrous THF (280.00 mL) was added NaH (9.37 g, 234.232 mmol, 3.00 equiv, 60%) in portions at 0° C. After 10 minutes, MeI (33.25 g, 234.232 mmol, 3.00 equiv) was added at 0° C., and the mixture was allowed to stir for 10 minutes at 0° C., and then the mixture was allowed to stir for 12 hours at room temperature. The resulting mixture was concentrated under reduced pressure. The crude solid was slurried with water (100 mL), and the solid was filtered and collected to give the 6-chloro-2-methyl-2,7-naphthyridin-1-one (14.6 g, 94.1%) as a yellow solid, which was used directly without further purification. LCMS (ESI) m/z: [M+H]$^+$=195.

Step 5: Preparation of 4-bromo-6-chloro-2-methyl-2,7-naphthyridin-1-one (Intermediate F)

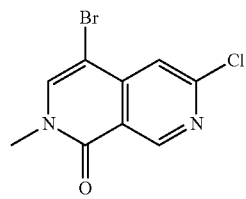

F

To a stirred mixture of 6-chloro-2-methyl-2,7-naphthyridin-1-one (8.00 g, 41.106 mmol, 1.00 equiv) in DMF (160.00 mL) was added NBS (8.78 g, 49.327 mmol, 1.20 equiv), and the resulting mixture was stirred for 2 hours at 90° C. The reaction mixture was cooled and diluted with DCM (150 mL) and washed with water (3×100 mL). The organic layers were dried and concentrated. Then the residue was slurried with EtOAc (20 mL), and the slurry was filtered. The filter cake was washed with EtOAc (20 mL) to give 4-bromo-6-chloro-2-methyl-2,7-naphthyridin-1-one (6.32 g, 55.7%) as a white solid, which was used directly without further purification. LCMS (ESI) m/z: [M-F1-1]+=273.

Step 6: Preparation of 6-(azetidin-1-yl)-4-bromo-2-methyl-2, 7-naphthyridin-1-one (Intermediate G)

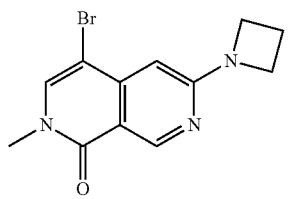

G

To a solution of 4-bromo-6-chloro-2-methyl-2,7-naphthyridin-1-one (5.00 g, 18.281 mmol, 1.00 equiv) and azetidine hydrochloride (3.2 g, 54.843 mmol, 3 equiv) in DMSO (50.00 mL) was added K$_2$CO$_3$ (12.6 g, 91.404 mmol, 5 equiv). The resulting solution was stirred at 130° C. for 2 hours. The reaction mixture was cooled and diluted with water (100 mL), and then extracted with EtOAc (3×100 mL). The combined organic layers were washed with saturated NaCl solution (3×50 mL), dried over anhydrous Na$_2$SO$_4$, and concentrated under reduced pressure to afford 6-(azetidin-1-yl)-4-bromo-2-methyl-2,7-naphthyridin-1-one (3.7 g, 68.8%) as a grey solid, which was used directly without further purification. LCMS (ESI) m/z: [M+H]⁺=294.

Step 7: Preparation of 4-[6-(azetidin-1-yl)-2-methyl-1-oxo-2,7-naphthyridin-4-yl]-2,6-dimethoxybenzaldehyde (Intermediate H)

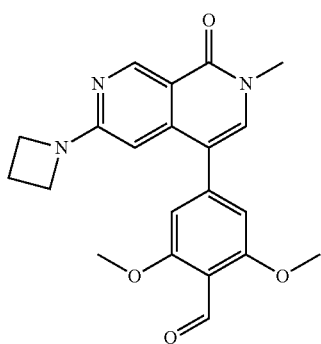

To a solution of 6-(azetidin-1-yl)-4-bromo-2-methyl-2,7-naphthyridin-1-one (1.42 g, 4.827 mmol, 1.00 equiv) and 4-formyl-3,5-dimethoxyphenylboronic acid (1.52 g, 7.241 mmol, 1.5 equiv) in dioxane (16.00 mL) and $H_2O$ (4.00 mL) was added Pd(dppf)Cl$_2$ (353.2 mg, 0.483 mmol, 0.1 equiv) and Cs$_2$CO$_3$ (3.15 g, 9.655 mmol, 2 equiv), and the resulting solution was stirred at 70° C. for 2 hours. The resulting mixture was cooled and concentrated under reduced pressure. The residue was slurried with water (30 mL) and filtered, and the filter cake was collected. This solid was further slurried with MeOH (30 mL) and filtered. The solid was collected to afford 4-[6-(azetidin-1-yl)-2-methyl-1-oxo-2,7-naphthyridin-4-yl]-2,6-dimethoxybenzaldehyde (1.42 g, 77.5%) as a grey solid. LCMS (ESI) m/z: [M+H]⁺=380.

Example 7—Preparation of 3-[1-oxo-6-[7-(piperidin-4-ylmethyl)-2,7-diazaspiro[3.5]nonan-2-yl]-3H-isoindol-2-yl]piperidine-2,6-dione (Intermediate P)

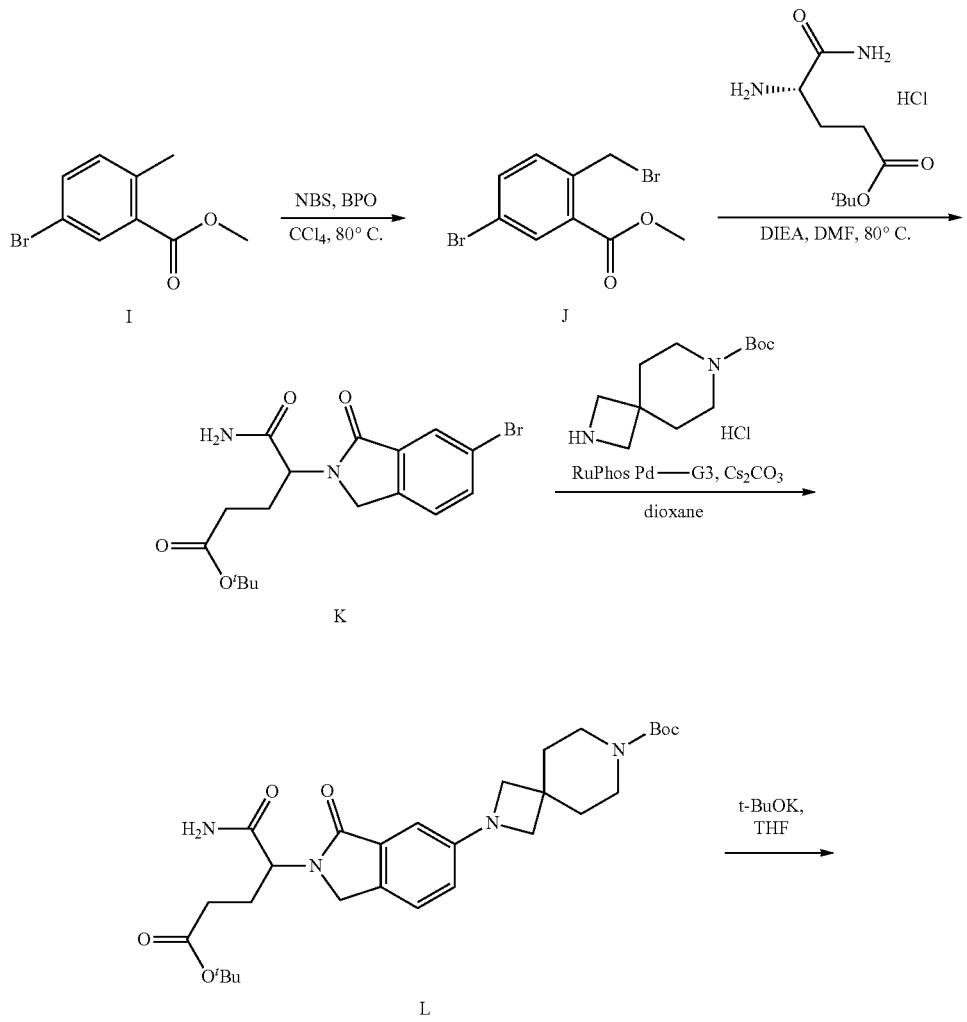

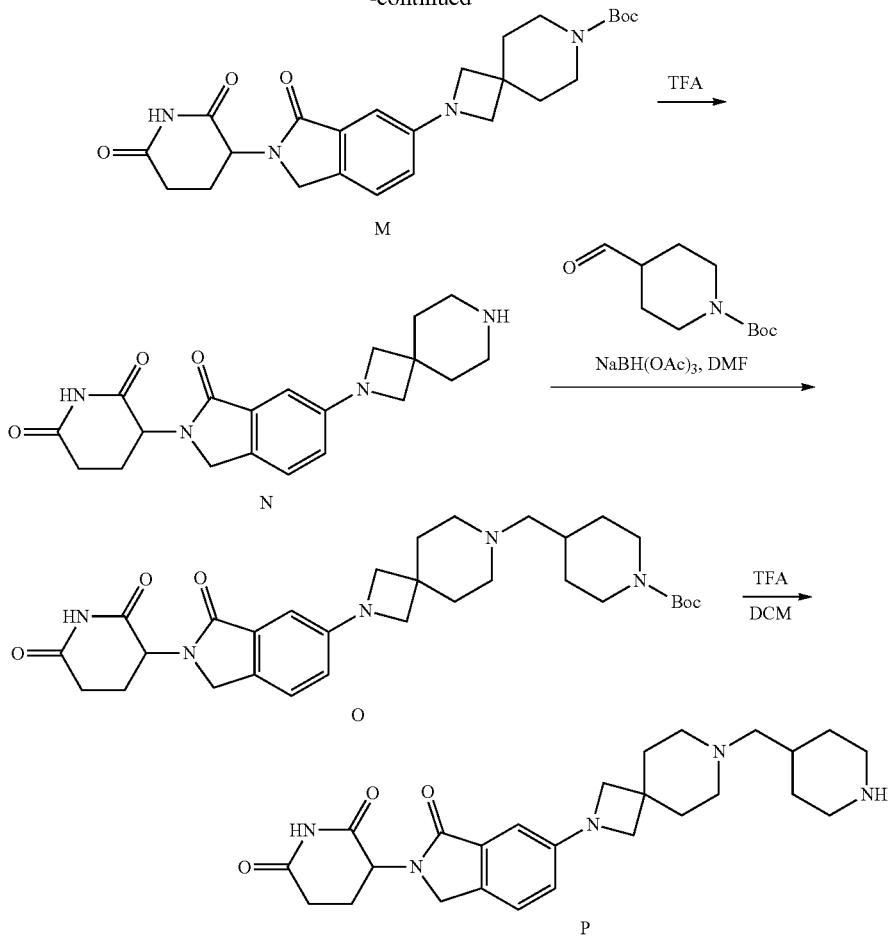

Step 1: Preparation of methyl 5-bromo-2-(bromomethyl)benzoate (Intermediate J)

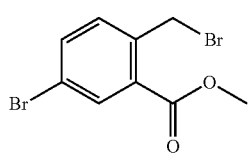

To a stirred mixture of methyl 5-bromo-2-methylbenzoate (50.00 g, 218.271 mmol, 1.00 equiv) in CCl$_4$ (500.00 mL) was added NBS (38.85 g, 218.271 mmol, 1.00 equiv) and BPO (5.59 g, 21.827 mmol, 0.10 equiv). After stirring for overnight at 80° C., the mixture was purified by silica gel column chromatography, eluted with PE/EtOAc (50:1) to afford methyl 5-bromo-2-(bromomethyl)benzoate (67 g, 74.75%) as a yellow oil. LCMS (ESI) m/z: [M+H]$^+$=307.

Step 2: Preparation of tert-butyl 4-(6-bromo-1-oxo-3H-isoindol-2-yl)-4-carbamoylbutanoate (Intermediate K)

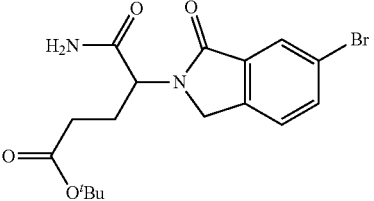

To a stirred mixture of methyl 5-bromo-2-(bromomethyl)benzoate (67.00 g, 217.554 mmol, 1.00 equiv) and tert-butyl (4S)-4-amino-4-carbamoylbutanoate hydrochloride (62.32 g, 261.070 mmol, 1.20 equiv) in DMF (100.00 mL) was added DIEA (112.47 g, 870.217 mmol, 4 equiv). After stirring for overnight at 80° C., the mixture was concentrated under reduced pressure. The residue was added water (200 mL) and stirred for 1 h at room temperature. The resulting mixture was filtered, the filter cake was added water (100 mL) and stirred. The precipitated solids were collected by filtration and washed with water (3×30 mL). This resulted in tert-butyl 4-(6-bromo-1-oxo-3H-isoindol-2-yl)-4-carbamoylbutanoate (55 g, 60.46%) as an off-white solid. LCMS (ESI) m/z: [M+H]⁺=397.

Step 3: Preparation of tert-butyl 2-[2-[4-(tert-butoxy)-1-carbamoyl-4-oxobutyl]-3-oxo-1H-isoindol-5-yl]-2,7-diazaspiro[3.5]nonane-7-carboxylate (Intermediate L)

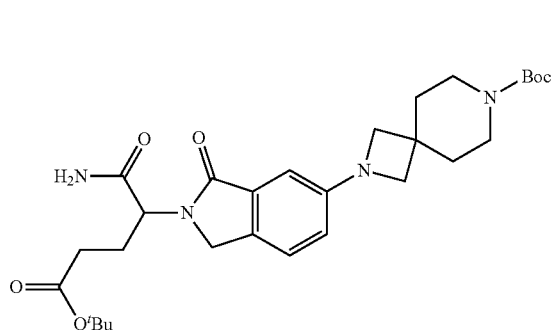

To a stirred solution of tert-butyl 4-(6-bromo-1-oxo-3H-isoindol-2-yl)-4-carbamoylbutanoate (10.00 g, 25.172 mmol, 1.00 equiv) and tert-butyl 2,7-diazaspiro[3.5]nonane-7-carboxylate hydrochloride (8.60 g, 32.723 mmol, 1.30 equiv) in dioxane (200.00 mL) was added Cs₂CO₃ (24.60 g, 75.516 mmol, 3.00 equiv) and RuPhos Palladacycle Gen.3 (2.11 g, 2.517 mmol, 0.10 equiv). After stirring for overnight at 100° C. under nitrogen atmosphere, the resulting mixture was filtered while hot, and the filter cake was washed with 1,4-dioxane (3×50 mL). The filtrate was concentrated under reduced pressure to afford tert-butyl 2-[2-[4-(tert-butoxy)-1-carbamoyl-4-oxobutyl]-3-oxo-1H-isoindol-5-yl]-2,7-diazaspiro[3.5]nonane-7-carboxylate (21 g, crude) as a black solid. LCMS (ESI) m/z: [M+H]⁺=543.

Step 4: Preparation of tert-butyl 2-[2-(2,6-dioxopiperidin-3-yl)-3-oxo-1H-isoindol-5-yl]-2,7-diazaspiro[3.5]nonane-7-carboxylate (Intermediate M)

To a stirred mixture of tert-butyl 2-[2-[(1S)-4-(tert-butoxy)-1-carbamoyl-4-oxobutyl]-3-oxo-1H-isoindol-5-yl]-2,7-diazaspiro[3.5]nonane-7-carboxylate (13.68 g, 25.208 mmol, 1.00 equiv) in THF (100.00 mL) was added t-BuOK in THF (25.00 mL, 25.000 mmol, 0.99 equiv). The resulting mixture was stirred for 2 hours at room temperature. The mixture was acidified to pH 6 with 1 M HCl (aq.) and then neutralized to pH 7 with saturated NaHCO₃ (aq.). The resulting mixture was extracted with EtOAc (3×200 mL). The combined organic layers were concentrated under reduced pressure. This resulted in tert-butyl 2-[2-(2,6-dioxopiperidin-3-yl)-3-oxo-1H-isoindol-5-yl]-2,7-diazaspiro[3.5]nonane-7-carboxylate (7.8 g, 59.43%) as a yellow solid. LCMS (ESI) m/z: [M+H]⁺=469.

Step 5: Preparation of 3-(6-[12,7-diazaspiro[3.5]nonan-2-yl]-1-oxo-3H-isoindol-2-yl)piperidine-2,6-dione (Intermediate N)

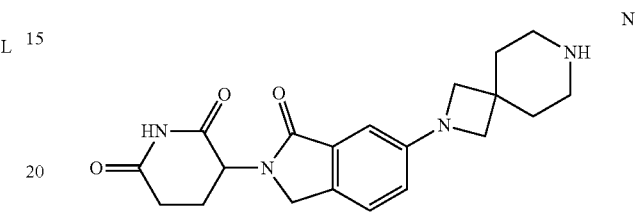

To a stirred mixture of tert-butyl 2-[2-(2,6-dioxopiperidin-3-yl)-3-oxo-1H-isoindol-5-yl]-2,7-diazaspiro[3.5]nonane-7-carboxylate (7.80 g, 16.647 mmol, 1.00 equiv) in DCM (10.00 mL) was added trifluoroacetic acid (TFA; 5.00 mL). After stirring for 2 hours at room temperature, the resulting mixture was concentrated under vacuum. This resulted in 3-(6-[2,7-diazaspiro[3.5]nonan-2-yl]-1-oxo-3H-isoindol-2-yl)piperidine-2,6-dione (6 g, 92.93%) as a light yellow solid. LCMS (ESI) m/z: [M+H]⁺=369.

Step 6: Preparation of tert-butyl 4-([2-[2-(2,6-dioxopiperidin-3-yl)-3-oxo-1H-isoindol-5-yl]-2,7-diazaspiro[3.5]nonan-7-yl]methyl)piperidine-1-carboxylate (Intermediate O)

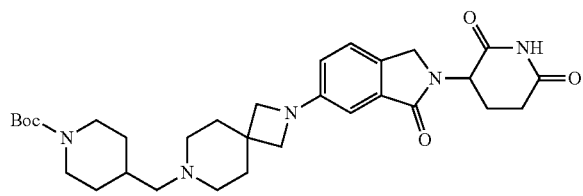

To a stirred solution of 3-(6-[2,7-diazaspiro[3.5]nonan-2-yl]-1-oxo-3H-isoindol-2-yl) piperidine-2,6-dione (4.00 g, 8.685 mmol, 1.00 equiv, 80%) and tert-butyl 4-formylpiperidine-1-carboxylate (1.48 g, 6.939 mmol, 0.80 equiv) in DMF (20.00 mL) was added NaBH(OAc)₃ (3.68 g, 17.363 mmol, 2.00 equiv) at room temperature. The resulting mixture was stirred for 2 hours at room temperature. The reaction was quenched with water at room temperature. The resulting mixture was purified by reverse flash chromatography with the following conditions (column, C18 silica gel; mobile phase, CH₃CN in water (0.1% FA), 0 to 100% gradient in 40 minutes; detector, UV 254 nm). This resulted in tert-butyl 4-([2-[2-(2,6-dioxopiperidin-3-yl)-3-oxo-1H-isoindol-5-yl]-2,7-diazaspiro [3.5]nonan-7-yl]methyl)piperidine-1-carboxylate (2.8 g, 51.29%) as a dark yellow solid. LCMS (ESI) m/z: [M+H]⁺=566.

Step 7: Preparation of 3-[1-oxo-6-[7-(piperidin-4-ylmethyl)-2,7-diazaspiro[3.5]nonan-2-yl]-3H-isoindol-2-yl]piperidine-2,6-dione (Intermediate P)

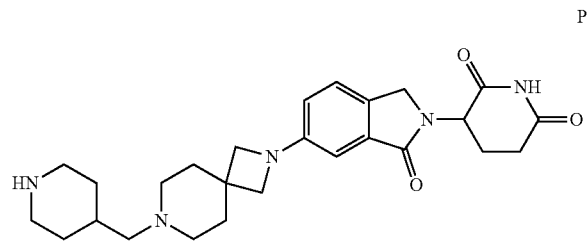 [SMILES: O=C1CCC(N2Cc3ccc(N4CC5(CCN(CC6CCNCC6)CC5)C4)cc3C2=O)C(=O)N1]

To a stirred mixture of tert-butyl 4-([2-[2-(2,6-dioxopiperidin-3-yl)-3-oxo-1H-isoindol-5-yl]-2,7-diazaspiro[3.5]nonan-7-yl]methyl)piperidine-1-carboxylate (2.80 g, 4.949 mmol, 1.00 equiv) in DCM (5.00 mL) was added TFA (2.00 mL). The mixture was stirred for 2 hours at room temperature. The resulting mixture was concentrated under reduced pressure to afford 3-[1-oxo-6-[7-(piperidin-4-ylmethyl)-2,7-diazaspiro[3.5]nonan-2-yl]-3H-isoindol-2-yl]piperidine-2,6-dione (3.9 g, crude) as a yellow solid. LCMS (ESI) m/z: [M+H]$^+$=466.

Example 8—Preparation of 3-[6-(7-[[1-([4-[6-(azetidin-1-yl)-2-methyl-1-oxo-2,7-naphthyridin-4-yl]-2,6-dimethoxyphenyl]methyl)piperidin-4-yl]methyl]-2,7-diazaspiro[3.5]nonan-2-yl)-1-oxo-3H-isoindol-2-yl]piperidine-2,6-dione TFA salt (compound D1 TFA salt)

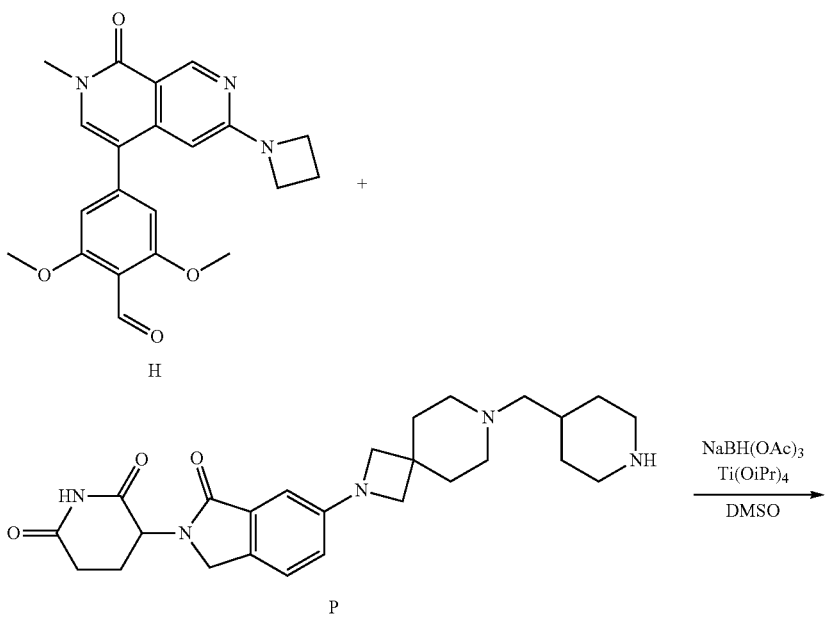

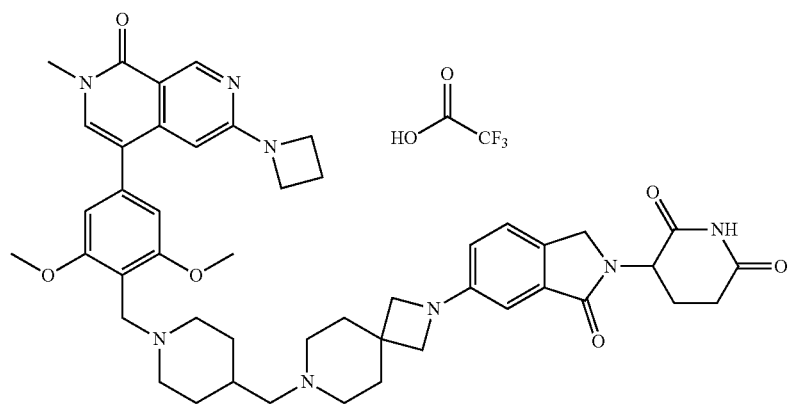

Compound D1 TFA salt

A solution of 3-[1-oxo-6-[7-(piperidin-4-ylmethyl)-2,7-diazaspiro[3.5]nonan-2-yl]-3H-isoindol-2-yl]piperidine-2,6-dione (4.5 g, 10.52 mmol, 1.00 equiv) and 4-[6-(azetidin-1-yl)-2-methyl-1-oxo-2,7-naphthyridin-4-yl]-2,6-dimethoxpenzaldehyde (4.0 g, 10.52 mmol, 1.00 equiv) and titanium(IV) isopropoxide (3.0 g, 10.52 mmol, 1.00 equiv) in DMSO (100 mL) was stirred at room temperature for 3 hours. Then NaBH(OAc)$_3$ (8.92 g, 42.08 mmol, 4.00 equiv) was added in batches to the above resulting solution, and the resulting mixture was stirred at room temperature overnight. The reaction was quenched by the addition of water (30 mL), and then the solution was filtered. The filter cake was wash by water and acetonitrile. Then the filtrate was concentrated in vacuo. The crude product was purified by reverse phase flash chromatography with the following conditions (Column: AQ C18 Column, 50×250 mm 10 μm; Mobile Phase A: Water (TFA 0.1%), Mobile Phase B: ACN; Flow rate:100 mL/minute; Gradient: 5 B to 25 B in 35 minutes; 254/220 nm). Pure fractions were evaporated to dryness to afford 3-[6-(7-[[1-([4-[6-(azetidin-1-yl)-2-methyl-1-oxo-2,7-naphthyridin-4-yl]-2,6-dimethoxyphenyl] methyl)piperidin-4-yl]methyl]-2,7-diazaspiro[3.5] nonan-2-yl]-1-oxo-3H-isoindol-2-yl]piperidine-2,6-dione TFA salt (3.2 g, 32.3%) as a white solid. $^1$H NMR (400 MHz, DMSO-d6) δ 10.96 (s, 1H), 9.01 (s, 1H), 7.59 (s, 1H), 7.36 (d, J=8.0 Hz, 1H), 6.72 (s, 2H), 6.68 (d, J=8.1 Hz, 2H), 6.20 (s, 1H), 5.07 (dd, J=13.3, 5.1 Hz, 1H), 4.35-4.13 (m, 2H), 4.06-3.95 (m, 4H), 3.80 (s, 6H), 3.57 (s, 4H), 3.47 (s, 5H), 2.97-2.75 (m, 3H), 2.70-2.55 (m, 1H), 2.44-2.16 (m, 7H), 2.13-1.88 (m, 5H), 1.80-1.67 (m, 4H), 1.61 (d, J=12.4 Hz, 2H), 1.53-1.33 (m, 1H), 1.13-0.94 (m, 2H). LCMS (ESI) m/z: [M+H]$^+$=829.55.

Enantiomers of compound D1 were separated by supercritical fluid chromatography on chiral support to produce compound S-D1 and compound R-D1.

Example 9—Preparation of Compound D2

In analogy to the procedures described in the examples above, compound D2 was prepared using the appropriate starting materials.

Compound D2: $^1$H NMR (300 MHz, DMSO-d6) δ 10.98 (s, 1H), 9.02 (d, J=0.7 Hz, 1H), 7.63 (d, J=2.3 Hz, 1H), 7.41 (d, J=8.8 Hz, 1H), 6.88 (s, 2H), 6.70 (h, J=2.4 Hz, 2H), 6.24 (d, J=6.0 Hz, 1H), 5.08 (dd, J=13.2, 5.1 Hz, 1H), 4.41-4.14 (m, 4H), 4.04 (t, J=7.4 Hz, 4H), 3.91 (s, 1H), 3.70 (d, J=22.5 Hz, 4H), 3.50 (s, 3H), 3.45 (s, 1H), 3.22 (s, 1H), 3.14-2.82 (m, 6H), 2.60 (d, J=16.2 Hz, 1H), 2.55 (s, 2H), 2.44-2.28 (m, 3H), 2.18-2.05 (m, 3H), 1.97 (t, J=13.9 Hz, 5H), 1.51 (q, J=12.2, 11.1 Hz, 2H). LCMS (ESI) m/z: [M+H]$^+$=835.45.

Example 10—SYO1 BRD9 NanoLuc Degradation Assay

This example demonstrates the ability of the compounds of the disclosure to degrade a Nanoluciferase-BRD9 fusion protein in a cell-based degradation assay.

Procedure: A stable SYO-1 cell line expressing 3×FLAG-NLuc-BRD9 was generated. On day 0 cells were seeded in 30 μL media into each well of 384-well cell culture plates. The seeding density was 8000 cells/well. On day 1, cells were treated with 30 nL DMSO or 30 nL of 3-fold serially DMSO-diluted compounds (10 points in duplicates with 1 μM as final top dose). Subsequently plates were incubated for 6 hours in a standard tissue culture incubator and equilibrated at room temperature for 15 minutes. Nanoluciferase activity was measured by adding 15 μL of freshly prepared Nano-Glo Luciferase Assay Reagent (Promega N1130), shaking the plates for 10 minutes and reading the bioluminescence using an EnVision reader.

Results: The Inhibition % was calculated using the following formula: % Inhibition=100×(Lum$_{HC}$-Lum$_{Sample}$)/(Lum$_{HC}$-Lum$_{LC}$). DMSO treated cells are employed as High Control (HC) and 1 μM of a known BRD9 degrader standard treated cells are employed as Low Control (LC). The data was fit to a four parameter, non-linear curve fit to calculate IC$_{50}$ (μM) values as shown in Table 2. As shown by the results in Table 2, a number of compounds of the present disclosure exhibit an IC$_{50}$ value of <1 μM for the degradation of BRD9, indicating their use as compounds for reducing the levels and/or activity of BRD9 and their potential for treating BRD9-related disorders.

TABLE 2

| SYO1 BRD9-NanoLuc Degradation | |
|---|---|
| Compound No. | SYO1 BRD9-NanoLuc degradation IC$_{50}$ (nM) |
| D1 | 0.13 |
| D2 | 0.18 |

Example 11—Degradation of BRD9 Inhibits the Growth of Synovial Sarcoma Tumor In Vivo Method: NOD SCID mice (Beijing Anikeeper Biotech, Beijing) were inoculated subcutaneously on the right flank with the single cell suspension of SYO-1 human biphasic synovial sarcoma tumor cells (5×106) in 100 μL Dulbecco's Modified Eagle Medium (DMEM) with 10% fetal bovine serum (FBS). The mice were randomized into either control group [10% dimethyl sulfoxide (DMSO), 40% polyethylene glycol (PEG400) and 50% water], or treatment group D1 when the mean tumor size reached about 117 mm$^3$. Mice were dosed daily through intraperitoneal (i.p.) route over the course of 3 weeks. All dose volumes were adjusted by body weights in terms of mg/kg.

Figure 14:
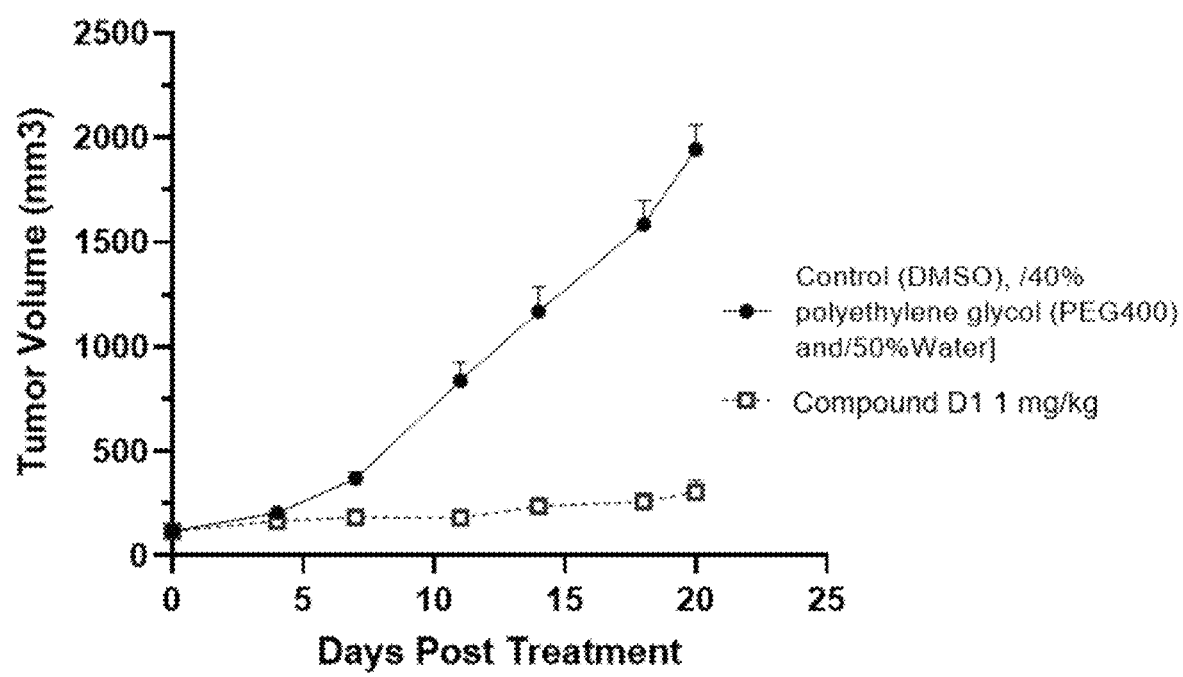
FIG. 14 is a graph showing efficacy of compound D1 in SOY-1 xenograft mouse model. Treatment with compound D1 led to tumor growth inhibition.

Results: As shown in FIG. 14, treatment with compound D1 at 1 mg/kg had led to tumor growth inhibition. All treatments were well tolerated based on % body weight change observed.

Example 12—Compound D1 Causes Degradation of BRD9 in Synovial Sarcoma Tumor In Vivo Method: Mice were treated with D1, 1 mg/kg, i.p. for 4 weeks. Mice were then euthanized, and tumors were collected at 8 hours, 72 hours, and 168 hours post last dose. Tumors were lysed with 1× RIPA lysis buffer (Boston BioProducts, BP-115D) with protease and phosphatase protein inhibitor (Roche Applied Science #04906837001 & 05892791001). Equal amounts of lysate (30 μg) were loaded in in 4-12% Bis-Tris Midi Protein Gels in 1×MOPS buffer; samples ran at 120 V for 120 minutes. Protein was transferred to membrane with TransBlot at 250 mA for 150 minutes, and then membranes were blocked with Odyssey blocking buffer for 1 hour at room temperature. Membranes were hybridized overnight in cold room with primary antibodies. Images acquired using Li-COR imaging system (Li-COR Biotechnology, Lincoln, Nebr.).

Table 3 shows detection antibody information.

TABLE 3

| Antibody | Vendor | Cat# | Species | Dilution |
|---|---|---|---|---|
| BRD9 | Bethyl, (Montgomery, TX) | A303-781A | Rabbit | 1:1000 |
| GAPDH | CST, (Danvers, MA) | 97166 | Mouse | 1:2000 |

Figure 15:
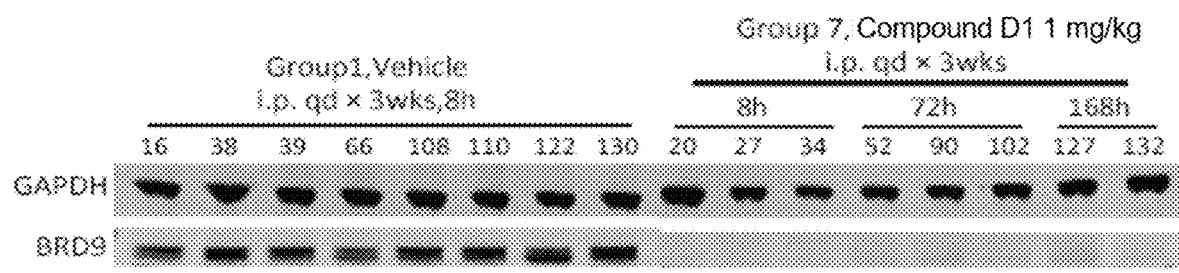
FIG. 15 is an image of a western blot showing BRD9 detection in the control group and the treatment group (compound D1). Treatment with compound D1 led to BRD9 inhibition.

Results: As shown in FIG. 15, treatment with compound D1 at 1 mg/kg led to complete degradation of BRD9 target up to 168 hours after dose.

Example 13—the Effect of Compounds S-D1 and R-D1 on Synovial Sarcoma Cells

Method. Synoial sarcoma cells were plated in 6-well plate at 500-100 k cells/well and treated with serial concentrations of BRD9 degrader (10 nM top concentration, diluted 1:3) the next day for two time points at 37° C. Cells were then harvested, washed with cold PBS, and frozen in cell pellets at −80° C. Lysates were prepared by resuspending thawed pellets in 1×RIPA Lysis and Extraction buffer (Thermo Fisher, Cat #89900) with 1× Halt™ Protease and Phosphatase Inhibitor Cocktail, EDTA-free (Thermo Fisher, Cat #78441) and 1:1000 dilution Pierce™ Universal Nuclease for Cell Lysis 25ku (Thermo Fisher, Cat #88700). Lysates were incubated on ice for 10 minutes and then centrifuged in 4° C. at maximum speed (15,000 rpm) for 10 minutes. Samples were then analyzed for total protein using BCA protein quantification assay and diluted to 1 µg/µL with lysis buffer and 1× NuPAGE™ LDS Sample Buffer (4×) (Thermo Fisher, Cat #NP0007) and 1×DTT from 30× stock (Cell Signaling Technologies, Cat #14265S). Samples with 20-25 ug of total protein were loaded into 4-12% Bis-Tris Mini-Gel with 1×MES Running buffer and run at 150V for 45 minutes. Gels were transferred using Trans-Blot® Turbo™ Transfer System (semi-dry) at 25V for 10 minutes (High MW setting) on nitrocellulose blots. Blots were blocked in 5% milk in TBST for 1 hour and probed with BRD9 antibody (Bethyl Labs, Cat #A303-781A, 1:750 for SYO1, and Cell Signaling Technologies, Cat #71232S for ASKA) and beta-Actin antibody (Cell Signaling Technologies, Cat #3700, 1:2000) overnight at 4° C. The next day, blots were washed in TBST 3× and probed with 1:5000 IRDye® 680LT Goat anti-Rabbit IgG Secondary Antibody (LiCOR, Cat #926-68021) and 1:10000 IRDye® 800CW Goat anti-Mouse IgG Secondary Antibody (LiCOR, Cat #926-32210) in LiCOR Odyssey® Blocking Buffer (TBS) for 1 hour at room temperature. Blots were washed in TBST 3× and scanned at 700 nM and 800 nM wavelength using LiCOR Odyssey® CLx Imaging System. Western blot signal was quantified using same analyses program included in the same machine. BRD9 signal was quantified by normalizing to beta-actin signal and all samples were normalized to DMSO, set as 100% signal.

For the assessment of interconversion between Enantiomer 1 and Enantiomer 2 in cell medium, the following test was performed. Enantiomer 1 and Enantiomer 2 (each was 40 µM in DMSO) was spiked into cell medium (DMEM+Glutamax+10% FBS) at a final concentration of 0.2 µM and incubated at 37° C. and 5% $CO_2$ in duplicate. At designated time point, aliquot (50 µL) was taken and processed by the addition of 150 µL of acetonitrile containing 0.1% formic acid and internal standard for LC/MS-MS analysis. Peak areas of both Enantiomer 1 and Enantiomer 2 were determined for each sample using a chiral specific analytical method. The results are summarized in Table 5 below.

Figure 16:
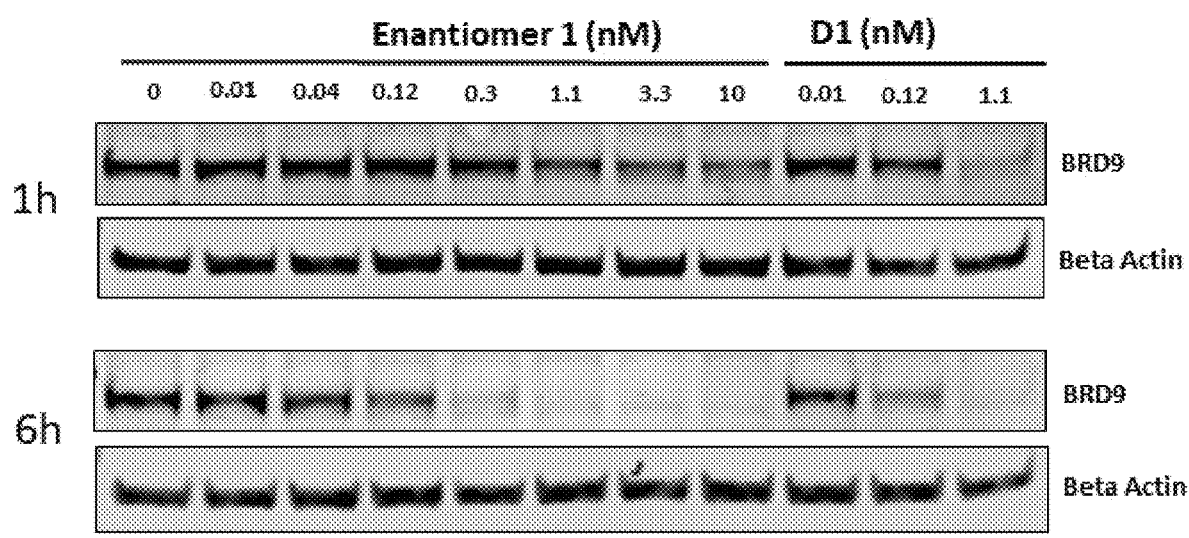
FIG. 16 is an image of western blots showing BRD9 detection in the SYO-1 cells treated with DMSO, Enantiomer 1, or racemic compound D1 for 1 or 6 hours.
Figure 17:
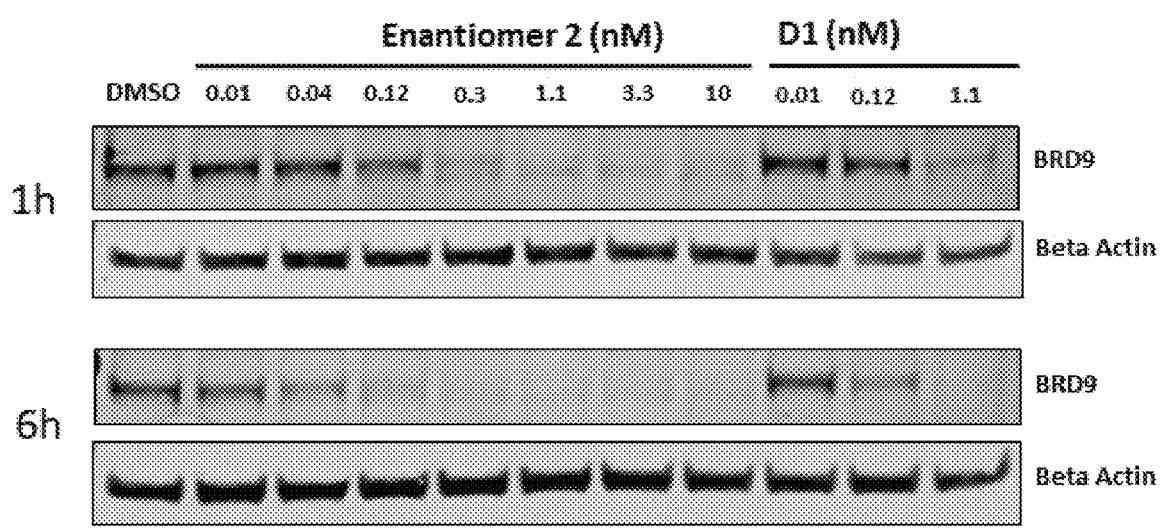
FIG. 17 is an image of western blots showing BRD9 detection in the SYO-1 cells treated with DMSO, Enantiomer 2, or racemic compound D1 for 1 or 6 hours.
Figure 18:
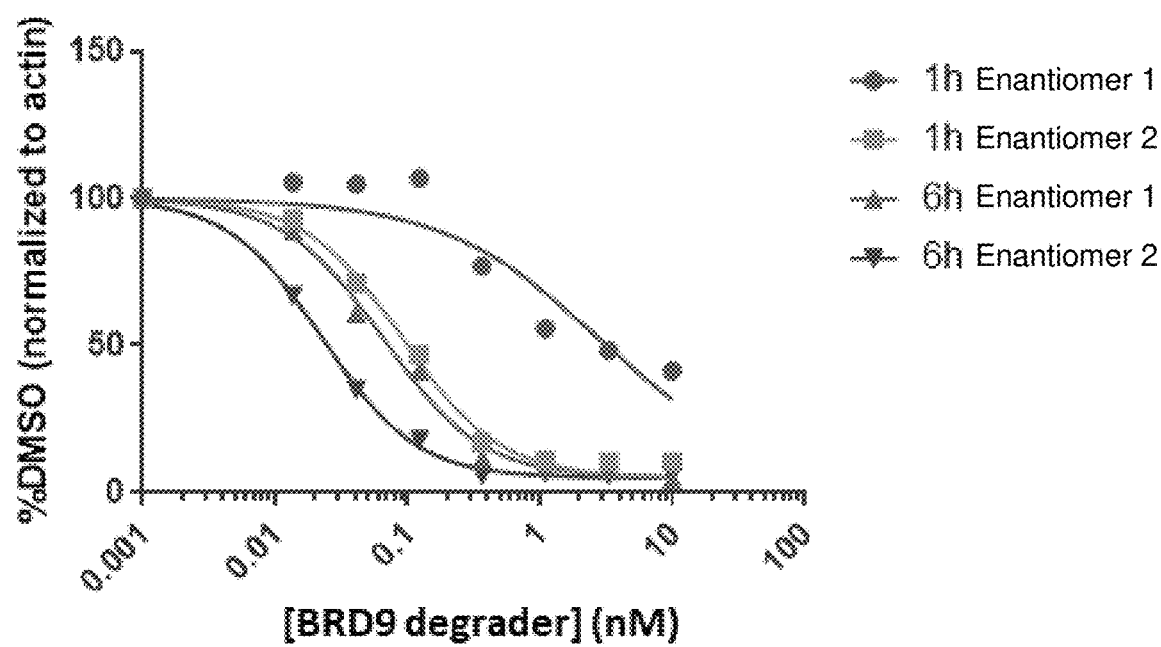
FIG. 18 is a graph showing dose response curves fitted to BRD9 band intensity data points from western blot images illustrated in FIGS. 16 and 17.
Figure 19:
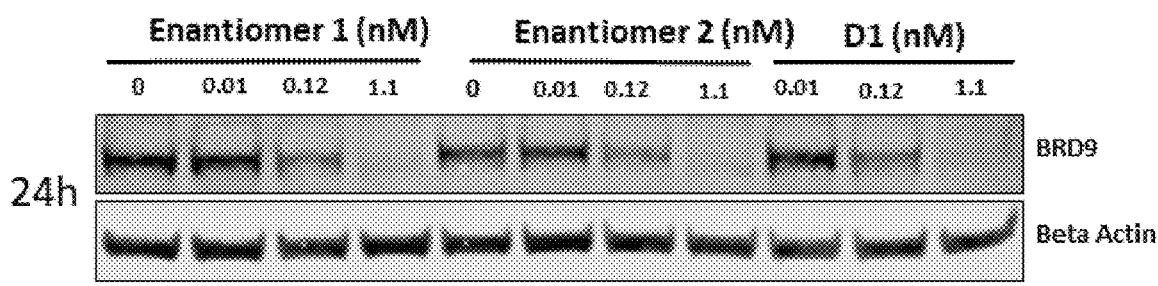
FIG. 19 is an image of western blots showing BRD9 detection in the SYO-1 cells treated with Enantiomer 1, Enantiomer 2, or racemic compound D1 for 24 hours.
Figure 20:
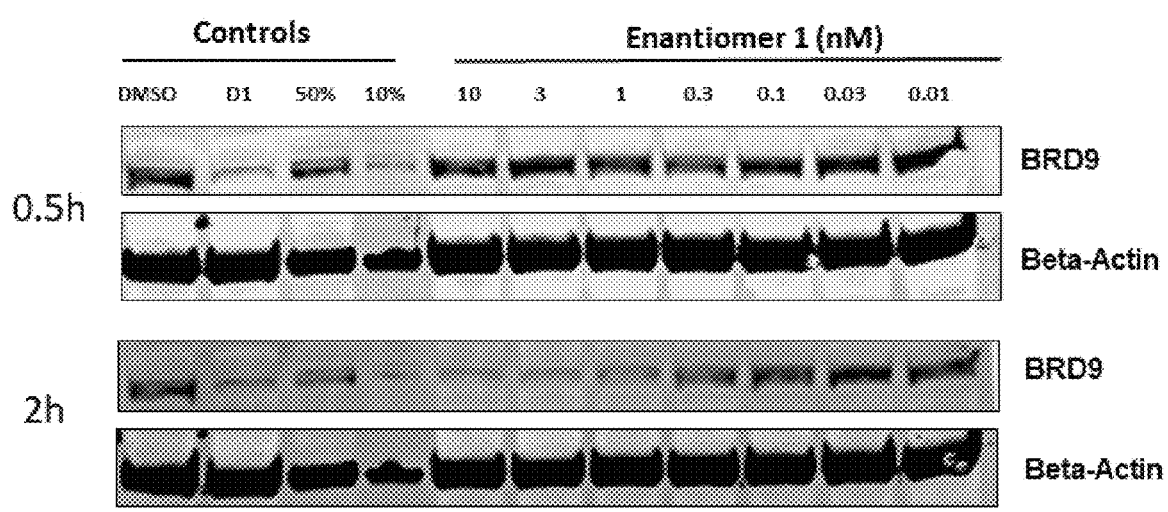
FIG. 20 is an image of western blots showing BRD9 detection in the ASKA cell controls and the ASKA cells treated with Enantiomer 1 or racemic compound D1 for 0.5 or 2 hours.
Figure 21:
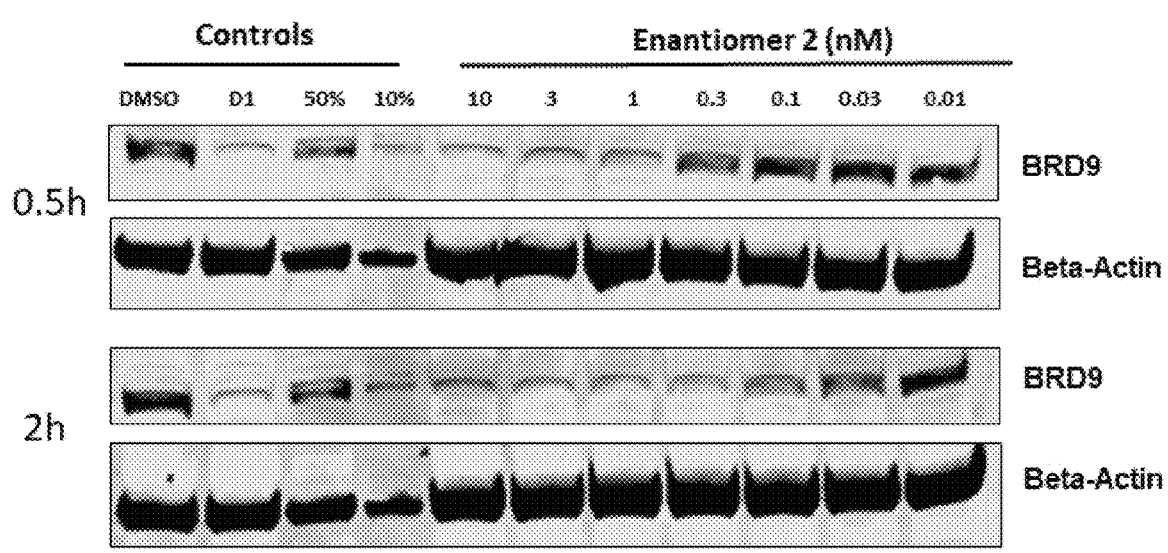
FIG. 21 is an image of western blots showing BRD9 detection in the ASKA cell controls and the ASKA cells treated with Enantiomer 2 or racemic compound D1 for 0.5 or 2 hours.
Figure 22:
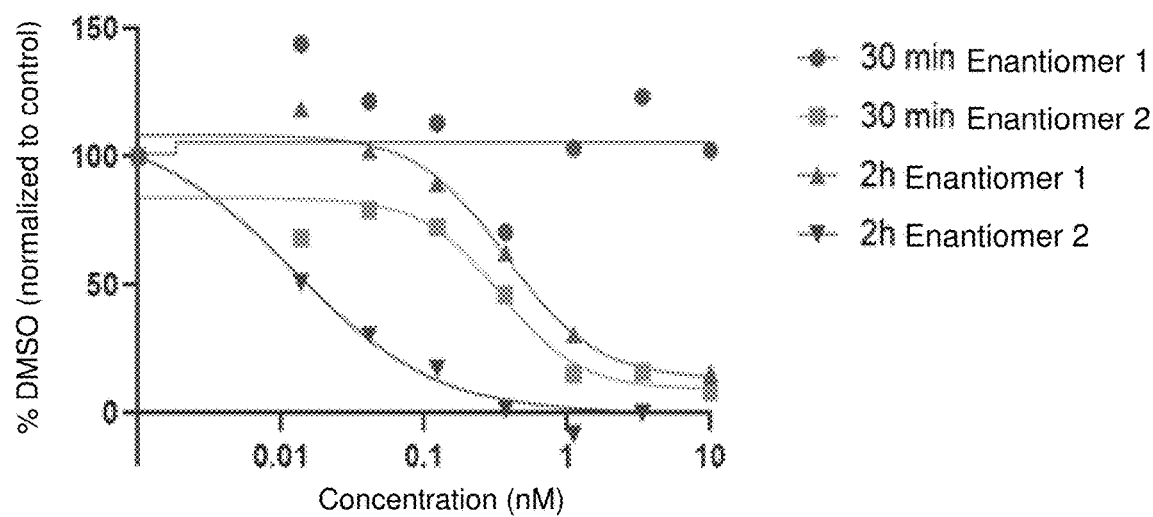
FIG. 22 is a graph showing dose response curves fitted to BRD9 band intensity data points from western blot images illustrated in FIGS. 20 and 21.

Results. To assess BRD9 degradation activity of two enantiomers, degrader treatment and subsequent western-blot experiments were carried out using two synovial sarcoma cell lines (SYO-1 and ASKA). Significant more potent BRD9 degradation activity was observed with Enantiomer 2, with a fitted $DC_{50}$ value of 0.092 nM, comparing to 2.8 nM for Enantiomer 1 in SYO-1 with 1 h treatment time (FIGS. 16, 17, and 18 and Table 4). Even more dramatic difference in ASKA cells is evident with a $DC_{50}$ of 0.34 nM for Enantiomer 2 at 30 minutes, but there is no discernable activity for Enantiomer 1 up to 10 µM at the same time point (FIGS. 20, 21, and 22 and Table 4). The difference is reduced to about 32-fold at 2 h in ASKA, with a fitted $DC_{50}$ value of 0.38 nM and 0.012 nM for Enantiomer 1 and Enantiomer 2, respectively (Table 4). The difference is further reduced to ca. 3-fold by 6 h in SYO1. Enantiomer 2 works slightly better than its racemic parent compound D1 in degrading BRD9 but overall comparable under the same study conditions (FIGS. 16 and 17). BRD9 degradation activity becomes highly similar for all three compounds at 24 h (FIG. 19). Taking together, Enantiomer 2 is much more potent in degradation endogenous BRD9 protein in two synovial sarcoma cell lines at early time point, whereas Enantiomer 1 is largely inactive or with much reduced degradation potency. However, the difference in potency is diminished over time and largely disappeared by 24 h.

TABLE 4

| Cell Line | Fitted $DC_{50}$ (nM) | Enantiomer 1 | Enantiomer 2 |
|---|---|---|---|
| ASKA | 0.5 h | >10 | 0.34 |
| SYO-1 | 1 h | 2.8 | 0.092 |
| ASKA | 2 h | 0.38 | 0.012 |
| SYO-1 | 6 h | 0.066 | 0.023 |

Epimerization of the chiral center in thalidomide or other IMiD drugs and their derivatives is reported. The acidic hydrogen in the chiral center can be scrambled under physical or neutral pH conditions. To investigate the chiral stability under cell assay conditions for these degraders, we performed a time course study for Enantiomer 1 and Enantiomer 2 in cell culture medium at 37° C. There is no detectable Enantiomer 2 in Enantiomer 1 samples at time 0 or 0.5 h. But substantial Enantiomer 2 was detected at later time points, accounting for 12% and 30% of the total at 2 h and 6 h, respectively (Table 5). Similarly, Enantiomer 2 is converted to Enantiomer 1 over time and its effective concentration was reduced to 63% at 6 h (Table 5). These data indicate that epimerization rate is relatively fast under the cell assay conditions, and suggest that the time-dependent BRD9 degradation activity for Enantiomer 1 is likely due to the converted Enantiomer 2. Overall, these data indicate that Enantiomer 2 is the active enantiomer in degrading BRD9 in cells.

TABLE 5

| | Enantiomer 1 Dosing | | Enantiomer 2 Dosing | |
| --- | --- | --- | --- | --- |
| Time (h) | Mean peak area ratio of Enantiomer 2 over Enantiomer 1 peak area ratio | % Enantiomer 2 | Mean peak area ratio of Enantiomer 1 over Enantiomer 2 peak area ratio | % Enantiomer 2 |
| 0 | 0.0 | 0.0 | 0.01 | 99 |
| 0.5 | 0.0 | 0.0 | 0.06 | 95 |
| 2 | 0.13 | 12 | 0.22 | 82 |
| 6 | 0.43 | 30 | 0.60 | 63 |

Example 14—the Effect of Compounds S-D1 and R-D1 on Synovial Sacroma Cells

Method. The SYO-1 tumor cells were maintained in vitro as adherent cells in Dulbecco's Modified Eagle Medium (DMEM) supplemented with 10% fetal bovine serum at 37° C. in an atmosphere of 5% CO2 in air. The cells growing in an exponential growth phase were harvested and counted for tumor inoculation. BALB/c Nude mice (Shanghai Lingchang biological science) were inoculated subcutaneously on the right flank with (5×10$^6$) in 0.1 mL of phosphate buffered saline (PBS). The treatment—(described in the table below)—was started on day 19 after tumor inoculation, when the average tumor size reached 499 mm$^3$.

Treatment Information:

| Antibody | Number of mice |
| --- | --- |
| Vehicle control, sulfobutylether-β-cyclodextrin (SBECD), Single Dose, 10 ul/g | 3 |
| Racemic D1, 0.5 mg/kg i.v., Single Dose, 10 ul/g (20% SBECD) | 12 |
| Enantiomer 1, 0.25 mg/kg i.v., Single Dose, 10 ul/g (20% SBECD) | 18 |
| Enantiomer 2, 0.25 mg/kg i.v., Single Dose, 10 ul/g (20% SBECD) | 18 |
| Enantiomer 2, 1 mg/kg i.v., Single Dose, 10 ul/g (20% SBECD) | 18 |

Mice were treated with racemic D1, 1 mg/kg, i.p. for 4 weeks, mice were euthanized, and tumors collected 1, 4, 8, 24, 48 and 72-hour post last dose. Tumors were lysed with 1×RIPA lysis buffer (Boston BioProducts, BP-115D) with protease and phosphatase protein inhibitor (Roche Applied Science #04906837001 & 05892791001). Equal amount of lysate (30 μg) were loaded in in 4-12% Bis-Tris Midi Protein Gels in 1×MOPS buffer; samples ran at 120 V for 120 min. Proteins was transferred to membrane (NC) with TransBlot at 250 mA for 150 minute, then membranes were blocked with Odyssey Blocking buffer for 1 hour at room temperature. Membranes were hybridized overnight in cold room with primary antibodies. Images acquired using Li-COR imaging system (Li-COR Biotechnology, Lincoln, Nebr.)

Detection Antibody Information:

| Antibody | Vendor | Cat# | Species | Dilution |
| --- | --- | --- | --- | --- |
| BRD9 | Bethyl, (Montgomery, TX) | A303-781A | Rabbit | 1:1000 |
| GAPDH | CST, (Danvers, MA) | 97166 | Mouse | 1:2000 |

Figure 23:
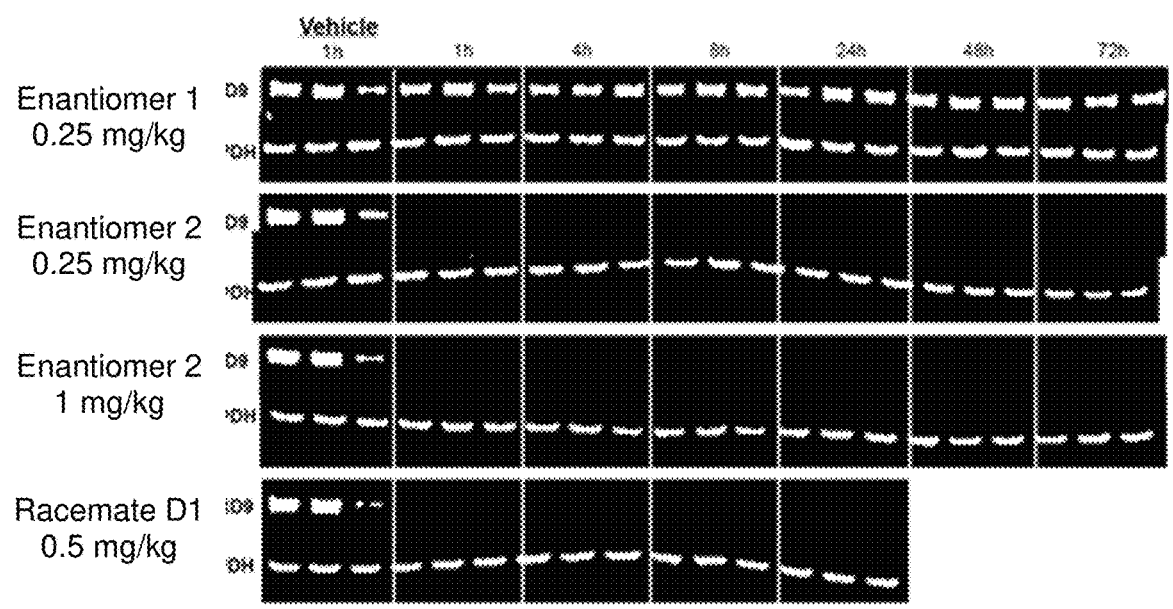
FIG. 23 are images showing a series of western blots for BRD9 detection in SYO-1 Zenograft model treated with Enantiomer 1, Enantiomer 2, or racemic compound D1.
Figure 24:
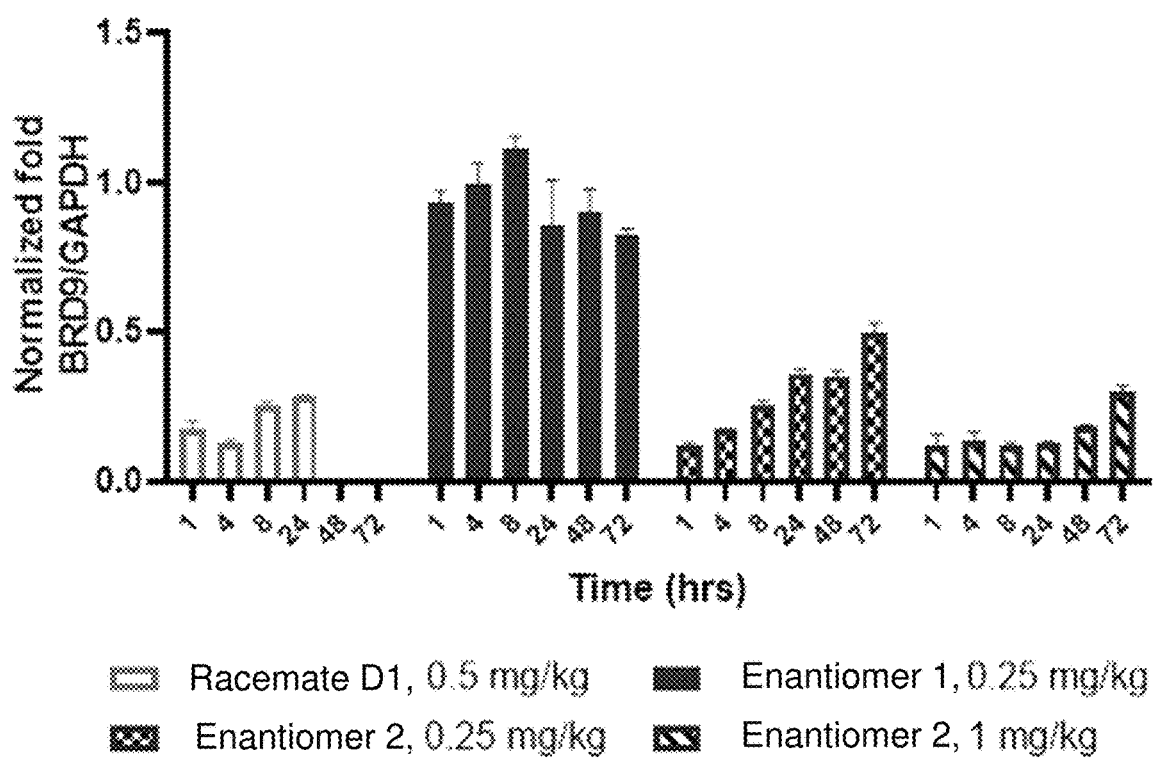
FIG. 24 is a bar graph quantifying the BRD9 level changes observed in western blots illustrated in FIG. 23.

Results. Pharmacodynamic activities of Enantiomer 1, Enantiomer 2, and racemic compound D1 were evaluated in SYO-1 Xenograft model. Enantiomer 2 demonstrated significant activity which was assessed by BRD9 protein level using western blot assay FIG. 23. Enantiomer 2 degraded BRD9 up to 72 hours after a single dose. Enantiomer 1 was inactive and did not degrade BRD9 protein. These results suggested Enantiomer 2 is equipotent to racemic compound D1.

OTHER EMBODIMENTS

All publications, patents, and patent applications mentioned in this specification are incorporated herein by reference in their entirety to the same extent as if each individual publication, patent, or patent application was specifically and individually indicated to be incorporated by reference in its entirety. Where a term in the present application is found to be defined differently in a document incorporated herein by reference, the definition provided herein is to serve as the definition for the term.

While the invention has been described in connection with specific embodiments thereof, it will be understood that invention is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are in the claims.

The invention claimed is:

1. A compound having the structure:

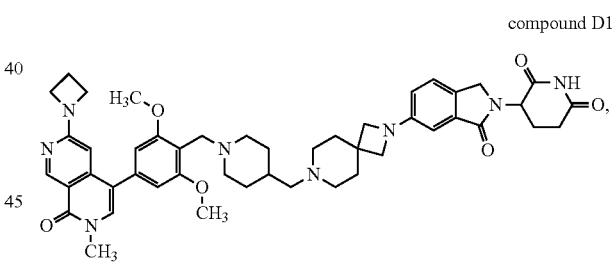

compound D1 or

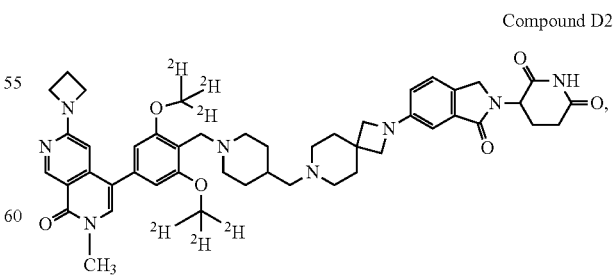

Compound D2 or a pharmaceutically acceptable salt thereof.

2. The compound of claim 1, wherein the compound has the structure:

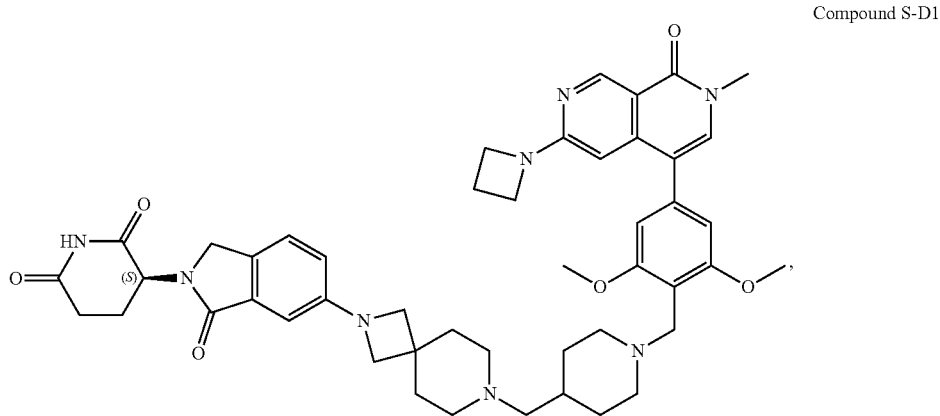

Compound S-D1 or a pharmaceutically acceptable salt thereof.

3. The compound of claim 1, wherein the compound has the structure:

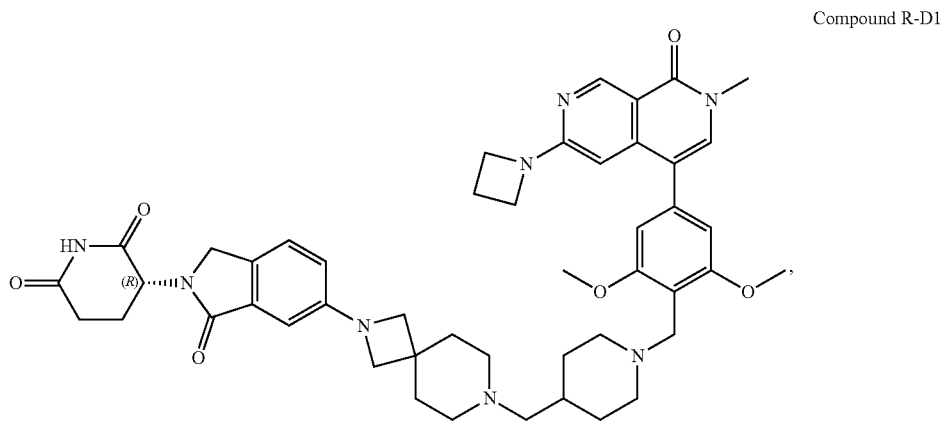

Compound R-D1 or a pharmaceutically acceptable salt thereof.

4. A pharmaceutical composition comprising a compound having the structure:

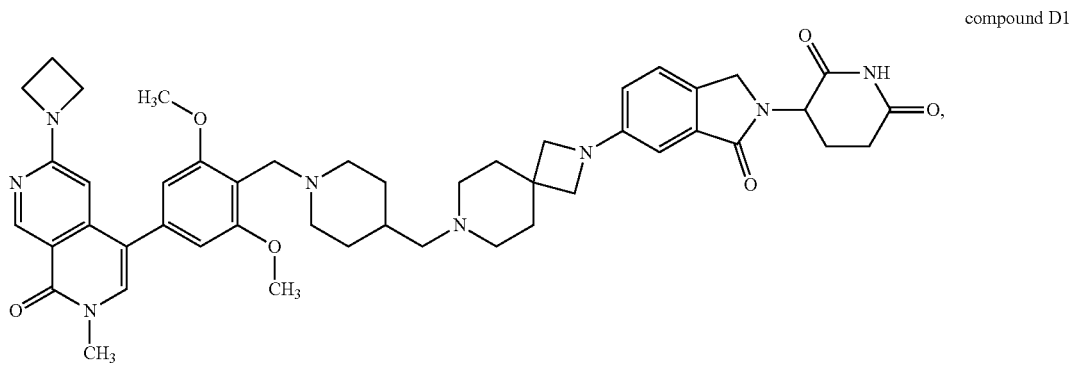 [SMILES: COc1cc(-c2cn(C)c(=O)c3cnc(N4CCC4)cc23)cc(OC)c1CN1CCC(CN2CCC3(CC2)CN(c2ccc4c(c2)C(=O)N(C2CCC(=O)NC2=O)C4)C3)CC1]

compound D1 or a pharmaceutically acceptable salt thereof and a pharmaceutically acceptable excipient.

5. The pharmaceutical composition of claim 4, wherein the pharmaceutical composition comprises a compound having the structure:

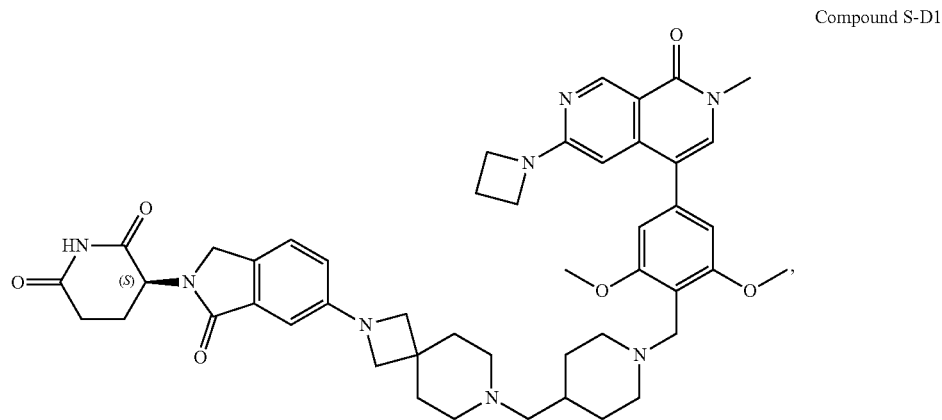
Compound S-D1
or a pharmaceutically acceptable salt thereof and a pharmaceutically acceptable excipient.
6. The pharmaceutical composition of claim 4, wherein the pharmaceutical composition comprises a compound having the structure:
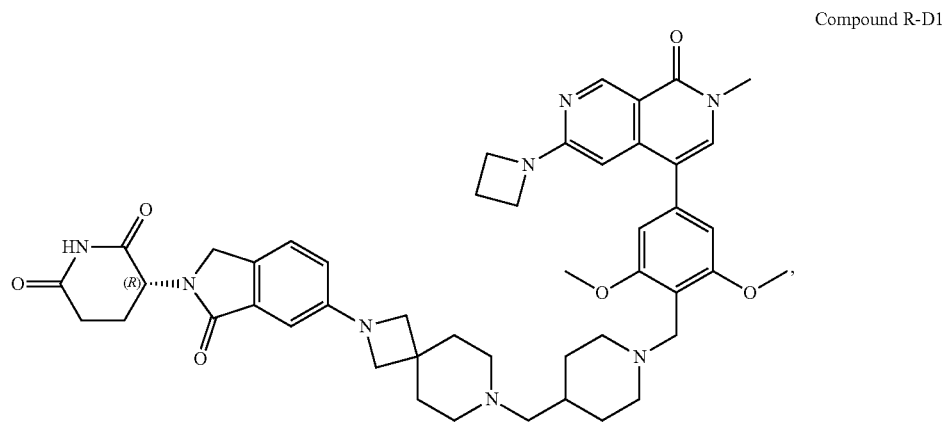
Compound R-D1
or a pharmaceutically acceptable salt thereof and a pharmaceutically acceptable excipient.
* * * * *